(12) United States Patent
Ott et al.

(10) Patent No.: US 8,034,350 B2
(45) Date of Patent: Oct. 11, 2011

(54) METHYLATED TAT POLYPEPTIDES AND METHODS OF USE THEREOF

(75) Inventors: Melanie Ott, San Francisco, CA (US); Sara Pagans Lista, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 260 days.

(21) Appl. No.: 12/190,414

(22) Filed: Aug. 12, 2008

(65) Prior Publication Data
US 2009/0233267 A1    Sep. 17, 2009

Related U.S. Application Data

(60) Provisional application No. 60/965,132, filed on Aug. 17, 2007.

(51) Int. Cl.
*A61K 39/21*    (2006.01)
*A61K 38/00*    (2006.01)

(52) U.S. Cl. .................. 424/188.1; 424/208.1; 530/345

(58) Field of Classification Search ........................ None
See application file for complete search history.

(56) References Cited

U.S. PATENT DOCUMENTS 7,589,167 B2 *    9/2009  Zhou et al. ..................... 530/300
2004/0247614 A1    12/2004  Dorr et al.

OTHER PUBLICATIONS

Boulanger, M.-C., et al., 2005, Methylation of Tat by PRMT6 regulates human immunodeficiency virus type 1 gene expression, J. Virol. 79(1):124-131.*

Wolfsberg, T. G. and T. L. Madden. 1999. Sequence similarity searching using the Blast family of programs. Curr. Prot. Prot. Sci. 2.5.1-2.5.29.*

Dorr et al. "Transcriptional synergy between Tat and PCAF is dependent on the binding of acetylated Tat to the PCAF bromodomain." EMBO J. Jun. 3, 2002;21(11):2715-23.

Nishioka et al. "Set9, a novel histone H3 methyltransferase that facilitates transcription by precluding histone tail modifications required for heterochromatin formation." Genes Dev. Feb. 15, 2002;16(4):479-89.

* cited by examiner

*Primary Examiner* — Jeffrey S. Parkin
(74) *Attorney, Agent, or Firm* — Paula A. Borden; Bozicevic Field & Francis LLP

(57) ABSTRACT

The present invention provides isolated methylated Tat peptides; and compositions comprising the peptides. The present invention further provides isolated antibodies specific for a Lys-51-methylated Tat polypeptide. Also provided are methods of identifying agents that inhibit Lys-51 methylation of a Tat polypeptide. The present invention further provides methods of treating an immunodeficiency virus infection in a mammalian subject.

14 Claims, 18 Drawing Sheets

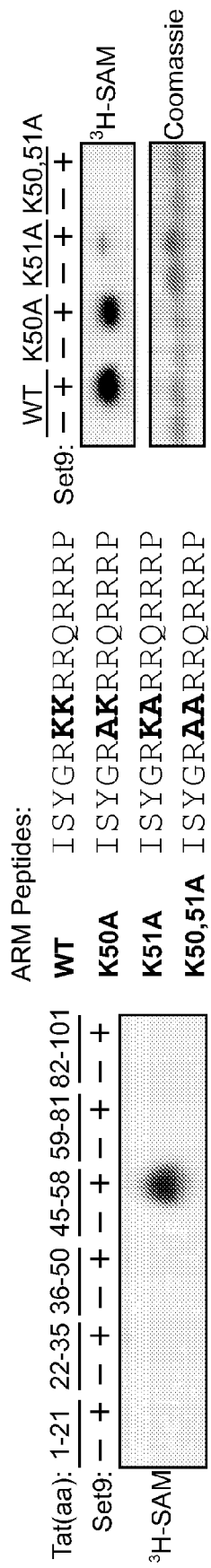
FIG. 2A
FIG. 2B
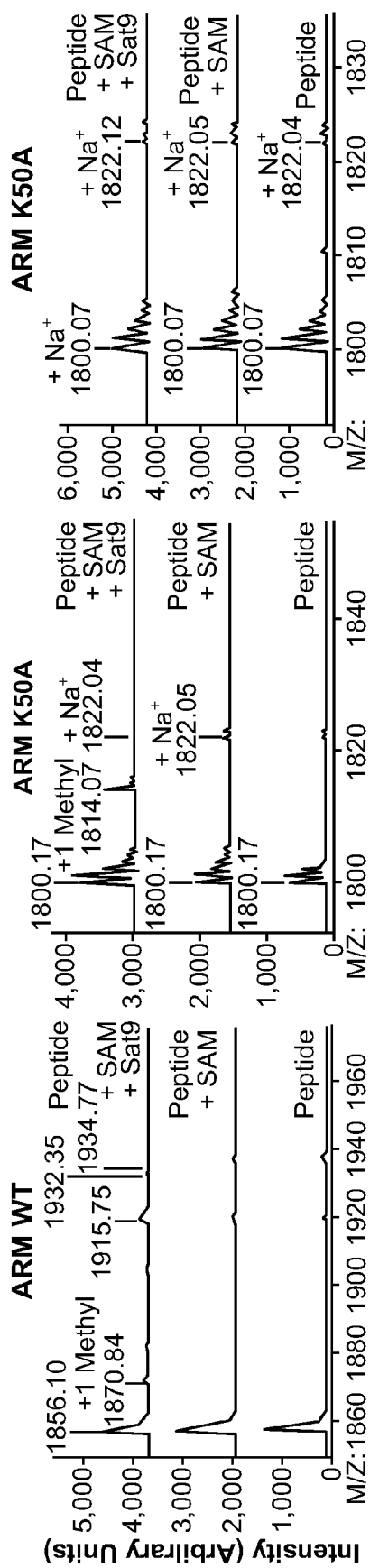
FIG. 2C

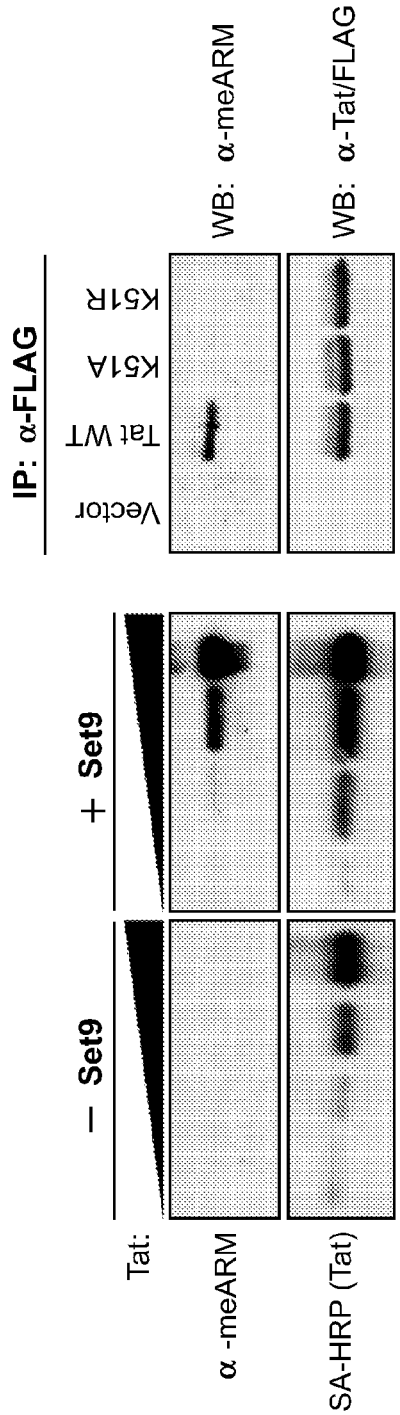
FIG. 7A
FIG. 7B
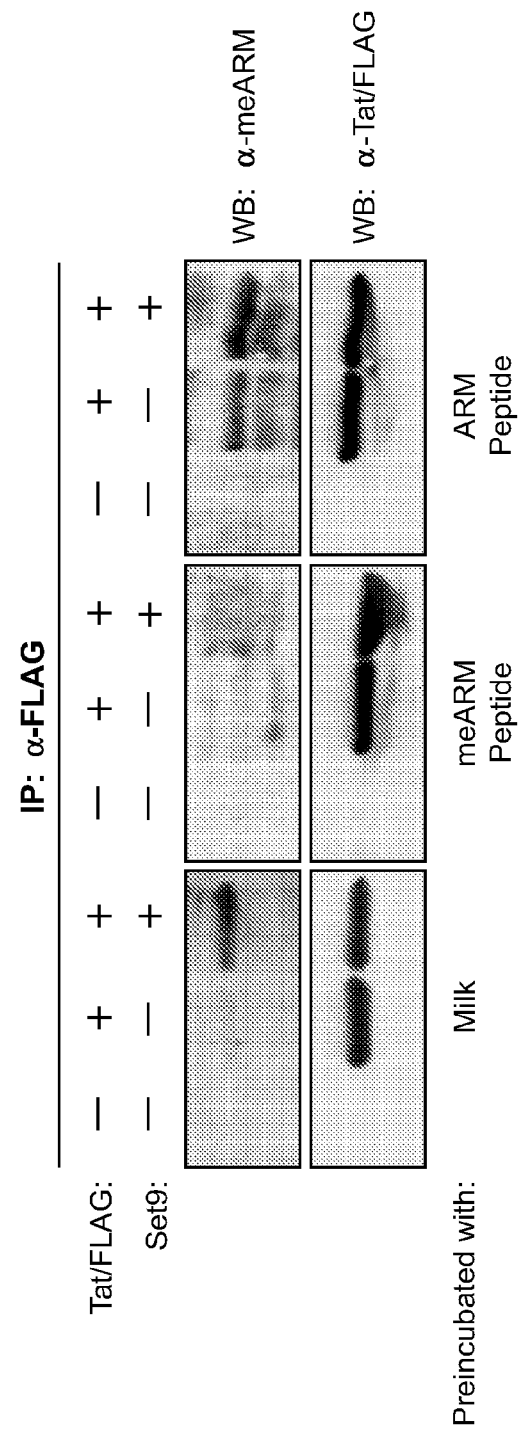
FIG. 7C

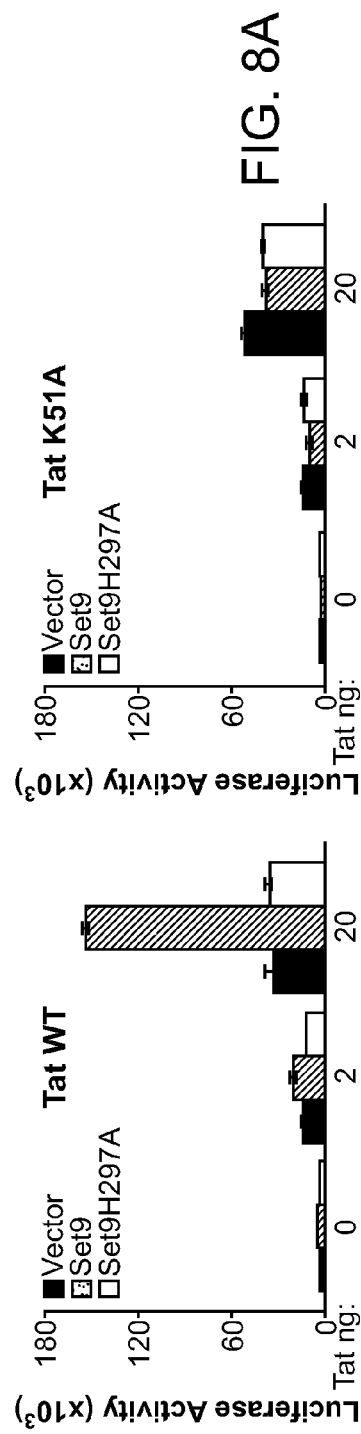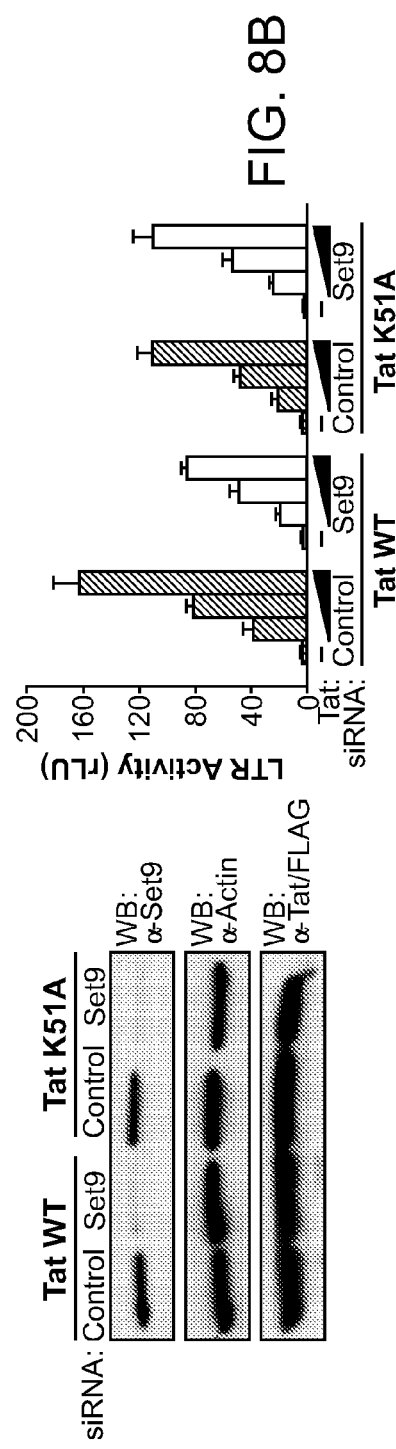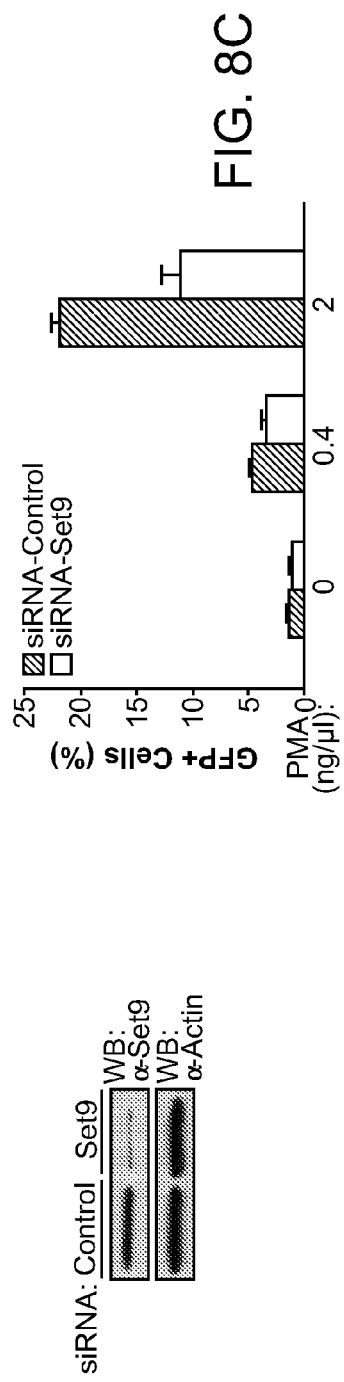
FIG. 8A
FIG. 8B
FIG. 8C

Consensus Tat polypeptide sequence

```
Met Glu Pro Val Asp Pro Arg Leu Glu Pro Trp Lys His Pro Gly Ser
 1           5                  10                 15

Gln Pro Lys Thr Ala Cys Thr Asn Cys Tyr Cys Lys Lys Cys Cys Phe
            20                  25                 30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
        50                  55                  60

His Gln Val Ser Leu Ser Lys Gln Pro Thr Ser Gln Ser Arg Gly Asp
65                  70                  75                  80

Pro Thr Gly Pro Lys Glu Ser Lys Lys Lys Val Glu Arg Glu Thr Glu
            85                  90                  95

Thr Asp Pro Phe Asp  (SEQ ID NO:1)
            100
```

FIG. 10

| 60 | 70 | 83 84 | 90 | 103 | |
|---|---|---|---|---|---|
| KRRQRRRPPQGSQTHQVSLSKQPTSQSRG | -DPT | GPKESKKKVERETETDPFD | - | (SEQ ID NO: 44) |
| KRRQRRRPPQGSQTHQVSLSKQPTSQSRG | -DPT | GPKE | - | (SEQ ID NO: 45) |
| KRRQRRRAPQGSQTHQVSLSKQPTSQSRG | -DPT | GPKE | - | (SEQ ID NO: 46) |
| KRRQRRRPPQGSQTHQVSLSKQPTSQPRG | -DPT | GPKE | - | (SEQ ID NO: 47) |
| KRRQRRRPPQGSQTHQVSLSKQPTSQPRG | -DPT | GPKE | - | (SEQ ID NO: 48) |
| KRRQRRRGPPQGSQTHQVSLSKQPTSQPRG | -DPT | GPKE | - | (SEQ ID NO: 49) |
| KRRQRRRGPPQGSQTHQVSLSKQPTSQPRG | -DPT | GPKESKEKVERETETDPAVQ | | (SEQ ID NO: 50) |
| KRRQRRRAHQNSQTHQASLSKQPTSQPRG | -DPT | GPKE | - | (SEQ ID NO: 51) |
| KRRQRRRAHQDSQNHQASLSKQPSSQTRG | -DPT | GPKEPKKEVEREAETDPLD | - | (SEQ ID NO: 52) |
| KRRQRQRAPDSSQNHQDSLSKQPSSQPRG | -DPT | GPKESKKEVERETETDPLD | - | (SEQ ID NO: 53) |
| KRRQRRRPSQGGQTHQDPIPKQPSSQPRG | -NPT | GPKE | - | (SEQ ID NO: 54) |
| KRRQRRRPSQGGQTHQDPIPKQPSSQPRG | -DPT | GPKE | - | (SEQ ID NO: 55) |
| KRRQRRRGPPQGGQAHQVPIPKQPSSQPRG | -DPT | GPKEQKKKVESEAETDP | - | (SEQ ID NO: 56) |
| KRRKPRRKPPQGDQAHQVPIPEQPSSQPRG | -DPT | GPKK | - | (SEQ ID NO: 57) |
| KRRQRRRPPQGNQAHQDPLPEQPSSQHRGDHPT | GPKE | - | (SEQ ID NO: 58) |
| KRRPRRRGPPQGSKDHQTLIPKQPLPQSQR | -VSA | GQEESKKKVESKAKTDRFA | - | (SEQ ID NO: 59) |
| KRRQRRRAPQDSQTHQASLSKQPASQSRG | -DPT | GPTESKKKVERETETDPFD | - | (SEQ ID NO: 60) |
| KRRQRRRPPQDSQTHQSSLSKQPTSQLRG | -DPT | GPTESKKKVERETETDPVH | - | (SEQ ID NO: 61) |
| KRRQRRRAPQDSKTHQVSLSKQPASQPRG | -DPT | GPKESKKKVERETETDPED | - | (SEQ ID NO: 62) |
| KRRQRRRA | - | - | - | (SEQ ID NO: 63) |
| KRRQRRRAPEDSQTHQVSLPKQPAPQFRG | -DPT | GPKESKKKVERETETHPVD | - | (SEQ ID NO: 64) |
| KRRQRRRAPQDSQTHQVSLPKQPASQARG | -DPT | GPKESKKKVERETETDPVD | - | (SEQ ID NO: 65) |
| KRRQRRRAPPDSEVHQVSLPKQPASQPQG | -DPT | GPKESKKKVERETETDPVH | - | (SEQ ID NO: 66) |
| KRRQRRRPPQDSQTHQVSLPKQPSSQQRG | -DPT | GPKESKKKVERETETDPDN | - | (SEQ ID NO: 67) |
| KRRQRRRPPQGSQTHQVSLSKQPTSQSRG | -DPT | GPKESKKKVERETETDPFD | - | (SEQ ID NO: 1) |

FIG. 11B

GenBank NP_085151
*Homo sapiens* Set9

```
  1 mdsddenvee aveghldddg lphgfctvty sstdrfegnf vhgekngrgk ffffdgstle
 61 gyyvddalqg qgvytyedgg vlqgtyvdge lngpaqeydt dgrlifkgqy kdnirhgvcw
121 iyypdggslv gevnedgemt gekiayvypd ertalygkfi dgemiegkla tlmsteegrp
181 hfelmpgnsv yhfdkstssc istnallpdp yeservyvae slissagegl fskvavgpnt
241 vmsfyngvri thqevdsrdw alngntlsld eetvidvpep ynhvskycas lghkanhsft
301 pnciydnfvh prfgpikcir tlraveadee ltvaygydhs ppgksgpeap ewyqvelkaf
361 qatqqk (SEQ ID NO:31)
```

FIG. 12A

GenBank NM_030648
*Homo sapiens* Set9

```
   1 atggatagcg acgacgagat ggtggaggag gcggtggaag ggcacctgga cgatgacgga
  61 ttaccgcacg ggttctgcac agtcacctac tcctccacag acagatttga ggggaacttt
 121 gttcacggag aaaagaacgg acgggggaag ttcttcttct ttgatggcag caccctggag
 181 gggtattatg tggatgatgc cttgcagggc cagggagttt acacttacga agatggggga
 241 gttctccagg gcacgtatgt agacggagag ctgaacggtc cagcccagga atatgacaca
 301 gatgggagac tgatcttcaa ggggcagtat aaagataaca ttcgtcatgg agtgtgctgg
 361 atatattacc cagatggagg aagccttgta ggagaagtaa atgaagatgg ggagatgact
 421 ggagagaaga tagcctatgt gtaccctgat gagaggaccg cactttatgg gaaatttatt
 481 gatggagaga tgatagaagg caaactggct acccttatgt ccactgaaga agggaggcct
 541 cactttgaac tgatgcctgg aaattcagtg taccactttg ataagtcgac ttcatcttgc
 601 atttctacca atgctcttct tccagatcct tatgaatcag aaagggttta tgttgctgaa
 661 tctcttattt ccagtgctgg agaaggactt ttttcaaagg tagctgtggg acctaatact
 721 gttatgtctt tttataatgg agttcgaatt acacaccaag aggttgacag cagggactgg
 781 gcccttaatg ggaacacccct ctcccttgat gaagaaacgg tcattgatgt gcctgagccc
 841 tataaccacg tatccaagta ctgtgcctcc ttgggacaca aggcaaatca ctccttcact
 901 ccaaactgca tctacgatat gtttgtccac cccgttttg ggcccatcaa atgcatccgc
 961 accctgagag cagtggaggc cgatgaagag ctcaccgttg cctatggcta tgaccacagc
1021 ccccccggga gagtgggcc tgaagcccct gagtggtacc aggtggagct gaaggccttc
1081 caggccaccc agcaaaagtg a
```

(SEQ ID NO:32)

FIG. 12B

GenBank AF430344 Tat

```
  1 atggagccag tagatcctag actagagccc tggaagcatc caggaagtca gcctaaaact
 61 gcttgtacca attgctattg taaaaagtgt tgctttcatt gccaagtttg tttcataaca
121 aaagccttag gcatctccta tggcaggaag aagcggagac agcgacgaag acctcctcaa
181 ggcagtcaga ctcatcaagt ttctctatca aagcaaccca cctcccaatc ccgaggggac
241 ccgacaggcc cgaaggaatc gaagaagaag gtggagagag agacagagac agatccattc
301 gattag
```

SEQ ID NO:29

FIG. 13

GenBank AF462150
Homo sapiens histone H3 lysine 4 specific methyltransferase mRNA

```
   1 atggatagcg acgacgagat ggtggaggag gcggtggaag ggcacctgga cgatgacgga
  61 ttaccgcacg ggttctgcac agtcacctac tcctccacag acagatttga ggggaacttt
 121 gttcacggag aaaagaacgg acggggaag ttcttcttct ttgatggcag caccctggag
 181 gggtattatg tggatgatgc cttgcaggc cagggagttt acacttacga agatggggga
 241 gttctccagg gcacgtatgt agacggagag ctgaacggtc cagcccagga atatgacaca
 301 gatgggagac tgatcttcaa ggggcagtat aaagataaca ttcgtcatgg agtgtgctgg
 361 atatattacc cagatggagg aagccttgta ggagaagtaa atgaagatgg ggagatgact
 421 ggagagaaga tagcctatgt gtaccctgat gagaggaccg cactttatgg gaaatttatt
 481 gatggagaga tgataagg caaactggct accttatgt ccactgaaga agggaggcct
 541 cactttgaac tgatgcctgg aaattcagtg taccactttg ataagtcgac ttcatcttgc
 601 atttctacca atgctcttct tccagatcct tatgaatcag aaagggttta tgttgctgaa
 661 tctcttattt ccagtgctgg agaaggactt ttttcaaagg tagctgtggg acctaatact
 721 gttatgtctt tttataatgg agttcgaatt acacaccaag aggttgacag cagggactgg
 781 gcccttaatg ggaacaccct ctcccttgat gaagaaacgg tcattgatgt gcctgagccc
 841 tataaccacg tatccaagta ctgtgcctcc ttgggacaca aggcaaatca ctccttcact
 901 ccaaactgca tctacgatat gtttgtccac cccgttttg ggcccatcaa atgcatccgc
 961 accctgagag cagtggaggc cgatgaagag ctcaccgttg cctatggcta tgaccacagc
1021 ccccccggga agagtgggcc tgaagcccct gagtggtacc aggtggagct gaaggccttc
1081 caggccaccc agcaaaagtg a
```

FIG. 14

GenBank NM_030648
Homo sapiens SET domain containing (lysine methyltransferase) 7 (SETD7), mRNA

```
   1 ggagaaagtt gcagcagcgg cagcggccaa ggcggcacac cggagcctcc gaggcgaggg
  61 gcaagtgggc gaagggaggg gggacgacgg ctgctgccgc agcagctgaa ggccaaggaa
 121 ttgaaagggc tgtaggggga ggcagtgcga gccagccccg actgctcctc ctcttcctcc
 181 tcctcctcca aactcgcgag ccccagagct cgctcagccg ccgggagcac ccagagggac
 241 gggaggcagc cgcgcagccc cgagctgggc agtgtcccca gccgccatgg atagcgacga
 301 cgagatggtg gaggaggcgg tggaagggca cctggacgat gacggattac cgcacgggtt
 361 ctgcacagtc acctactcct ccacagacag atttgagggg aacttcgttc acggagaaaa
 421 gaacggacgg gggaagttct tcttcttcga tggcagcacc ctggagggtt attatgtgga
 481 tgatgccttg cagggccagg gagtttacac ttacgaagat ggggagtttc tccagggcac
 541 gtatgtagac ggagagctga acgtccagc ccagaatat gacacagatg ggagactgat
 601 cttcaagggg cagtataaag ataacattcg tcatgagtg tgctggatat attacccaga
 661 tggaggaagc cttgtaggag aagtaaatga agatggggag atgactgag agaagatagc
 721 ctatgtgtac cctgatgaga ggaccgcact ttatgggaaa tttattgatg gagagatgat
 781 agaaggcaaa ctggctaccc ttatgtccac tgaagaaggg aggcctcact ttgaactgat
 841 gcctggaaat tcagtgtacc actttgataa gtcgacttca tcttgcattt ctaccaatgc
 901 tcttcttcca gatccttatg aatcagaaag ggtttatgtt gctgaatctc ttatttccag
 961 tgctggagaa ggactttttt caaaggtagc tgtgggacct aatactgtta tgtcttttta
1021 taatggagtt cgaattacac accaagaggt tgacagcagg gactgggccc ttaatgggaa
1081 caccctctcc cttgatgaag aaacggtcat tgatgtgcct gagccctata ccacgtatc
1141 caagtactgt gcctccttgg acacaaggc aaatcactcc ttcactccaa actgcatcta
1201 cgatatgttt gtccaccccc gttttgggcc catcaaatgc atccgcaccc tgagagcagt
1261 ggaggccgat gaagagctca ccgttgccta tggctatgac acagccccc ccgggaagag
1321 tgggcctgaa gcccctgagt ggtaccaggt ggagctgaag gccttccagg ccacccagca
1381 aaagtgaaag gcctggcttc gggggttcaga gacctggaat agaaacttgg atctatgcac
1441 tacgtttatc tgacaatggg acaaccaggg actgctcatg ctgtgacgtc acatcctctc
1501 accatgcgtt agcaacgact ttctcgcata ctaactaggt ttgactgtat tactcatacc
1561 agatttaaaa ttagctagcc ttgcaacaac gtcctactga gaggtattgt cgagcatttg
1621 acataagaca gcgtgatgtt cttggtggt tcaagtctaa atctgtacca cattcggaga
1681 tgccaaatga ttagactgaa acaggaaaac ggggttttc agtcattttt agtcagtggt
1741 ttttccatag tgctttttc ctatggccag tgcaaattgt gttagcacac ttgcatatgt
1801 gccgtattaa gggttgacaa ttactacatc tttattctct aaatgtagta taatttgcct
1861 tttaacctt gatctgtatc ttgcaataga atggctttgg tttttcctt agtaaatagg
1921 agcccacttc taaagtcatt tcaccctca gcctattct ctttcttaga tacccttac
1981 aagagaaaac ttccaaatgg attttgcat caatagcagt gtgtaggtct ctctggttct
2041 ttctatatca tcatttatt attatgtcct aatataaagt actggctcat agggccaggg
2101 tattattata gaatattatt ctcgcatgt aacaaagata tctttgcttt aagatgtgag
2161 aagaaatgaa tttactttgt ttgcattaag ttatggaaga gttgtaatat atacttaag
2221 aaagaagaga agaaaactag tatctctaag cggtaactat ggcaattttg caatattttc
2281 agtagtgcta gtaattttt cctccttgag tacacattaa atgtacataa catagcgcgg
2341 tcaggcttgt ggcacagtgc attgaattca aaagtcaaac agcaaatttg aattctaaca
2401 gaattcaaaa aaaaatttt ttagtcagta ctactaaggc agacacactg attactaggt
2461 acaaatcaaa ccttgatgct aaaactcttc atcattgtaa tttcaaagca cttacctgct
2521 tcaaaacatt gtaaactaag actgaacacc tgtatagttt aaaagcaaca ctatcaatag
2581 catttcagcc attttgccag ccatgtgtaa tcacaactgc agaaataagg agaaaccccc
2641 tgtttttta gtttagctaa ttagatctgt aacatcactg ggattgctct gaatgaatcc
2701 tgagagtttt gttttttata agcaccctca ccacatgcca tagcttgtc tcttttagac
2761 acctcgatgc agcggctgga aggactggag agcagctgtt gtgctgatct gtagctgtca
2821 gctgtgattc ctgtcacctg agtcagttg gtctggaaag cgaaggcctt ccaagctgta
2881 gcagatagtg agctccagct gatgagagaa ggcttcagtg aagaagagt gaggacatag
2941 gcagaaggaa gtttgctatt tcttgtcagt tgcacattgc tttatgaaga ctacaacaaa
3001 agtgcttaat cccaggctgc tcatgacttt catttcaggt ggccttggg cacattgaca
3061 gagttgcct tccttctttt gcaacaccg gcttcctaga gcacccggtt gcatgctttg
3121 cagctaggtt gcagtggttt cagggagatc cagttggatc cctgcttgaa agcttaagcc
3181 aatggttcac ccatgagagg aagttgtcag tgcttccagg aagattgccc accaaaggaa
3241 ctgaatagtt tttagattta aaggcaccag gataggtca ctcttactct gtagaaagag
3301 accgttctat acactgtgac ggatgggcca gggcctctgg acttgcattc tgataggtgc
3361 tttaatttaa atgtgcccaa agggagtgac tgtcttcagg agaaagatgg cttgcattaa
3421 cctcgatcaa gtgggttgtg cagccaggtc agggaatgcg gtcaggagaa ggatagtgct
```

FIG. 15A

```
3481 ggtcatgccc ccgatgcagc tatgctctga atgatttcat tcctgagagt gatagcattc
3541 tggtcctggc tgcagtgggg tacaatttac gtcctaagtg ggggctactc taattatccc
3601 attcaaatgg aattttttc aaaattggat agaaggaatt gaagagttgt aagtagtgat
3661 tagtctgcta atcagttctt cagatgagat attgaatggt aacactctga gcttaaaact
3721 cagcagtgtg tctgtgacct ccacgcaaat cagaggaagc aatgcatcca cgctgagcct
3781 caccatgtct tcctcccaac tctcttcata ctctctgtgt cttccagctc ttctttctct
3841 ggccggctct cttttcctctt ctctctgcat atgtgagaac gcctgggcat cctgggtaac
3901 agcagcccca gctgccctct cctgttccct gttccaagtc ccctgcactg acctttcttg
3961 agtctctctg gtctgtgca tgtctttggg actctgctca tctggctttt cctctgtgtg
4021 tgcctctctg tttgcttatg tctctggctc tgtcttcccc accctcccc tcacacacac
4081 acatactccc aaatgtaagg ctctgtggca ggttggaatc ggagtaaggc ttgagattca
4141 ctgagttctg taggtaggga agaagtcaa gggagtggag gttctataag gaattaacag
4201 ctgaggacgg aagggtttgt ttcccgtttg aacctaaacg caagtggaaa agaatactca
4261 gaatgtattt ttctacttta catctgctgg ggaaggaaat gtgtcaggaa gccgctgcat
4321 ctggtcattt catcgcatca gaatcacagc agacgtggaa gattccatgt ggtggggaat
4381 aaagaaataa ctttatgctc tcctgaaaaa cagcgggagc ctatgtgtgt gtgcgacact
4441 gtaatctcaa ggagattcac tcagagctgt ctcagtccaa ctcctgcatg accagatctt
4501 cccttagcat cttttctgtg atgaaatatt atcttgtgtt agagttagga ataggaacta
4561 acctgtagga gcatgtcccc aaatggacat ttgaatggac taacaaaaac aactggaaag
4621 actgaatttc cgacacaaag gaatgatggg atcaaaaaga aagcagtgag gagttcttga
4681 gtcttgtagt acctattctt attttaactt gcttcatcct tgatctacct gagacactaa
4741 gaaggaaatt agttttccaa gagctctttg aacctgtcta ggactgtagt taaacctatt
4801 tgccctatgg gggttcttca cactcgaaaa actatttcct tatcaccaac gacccaccca
4861 gaaaggccaa tgaggccaaa tgtaacaatt tttaacattt aaatataact attaaaattg
4921 cattaattgt gaacagtgaa ttaaagggtt gtcttctcca ggagacagta tgtggcactt
4981 ttcgtaaatt tcatttaata tataaaaatt taaatcactc actgcaacat gcatttaaaa
5041 tcttccaaga aggtagaggt atcatttttct gttttgctttt gttttaaaac agttgcctca
5101 agcttctgtc ttaagagtag tgacttagaa tccagatatc ttttgttta gaaaaacaag
5161 caaaactatg ttgcaagact gacagttgta atgtttattt gccacagatc aaaggttcac
5221 aaagtatatc aaatttacat ctacttgggg taccttgata gattattatt gttttctttt
5281 tatctttccc ttcaggaatt tggaaactcg ttgtcacttt ttttaatttt aaaatacta
5341 aattgtaata gttttctttt gccaaatgtg tgcgtacata ttcaaagcaa tgaaactatt
5401 tcaagccata caaccacagg ggtgggaacc cttttcacaa attttaatgt gtttgtatgt
5461 aaatagatgt ttgtatgaaa tattttcatg atagaatgaa tatatttaaa tgaagttgaa
5521 ttattccagt gctacttaaa cacattacaa aaattttggt gagaattatc tgagtctatt
5581 gagatgtaat gcagatcaat tttgattttt aaaaatcaaa agcctacaat aactctgact
5641 ctcagcaact tcctcggcgt tgttgcacct gacgtggaga gagctcgtag gcttccccag
5701 tgcctcagcc gcttcctggt ggaagttagg tgctaatgga ggtgtgttca cctttttagtg
5761 atatcactgc aggcctttga ggggcctgag agtgaatcag aggcattaga gacaccggtg
5821 cagttatctg gagcacaatt tctttgcagg gcagcagaat cagaagccag acttggccat
5881 gtgaacctcg aaactcggtt tcccggccgc catcaaccgc cacccttact gcctagtcac
5941 acacgtcagg gaggctgccc tcagtggagt tggggttgag accccagggt gggacttcac
6001 agttttgcca gcaatctcta ccttctgact tctgcctcgc agagaggaag gagaggggag
6061 catctggcaa ggggcccatt tctcagcaca gtacatttcc tgtctcagct ctggaagact
6121 atgcacccaa gcaccaaact tccaaccaga gagagagacg tcctccgata acaaaaatcc
6181 ttgcttcctc tgtctgtgac tttacacaca gttgttcaaa gttgttaaat gtcaagagtc
6241 aatcacatcc ctaggacata cctcccaact ctcctgactc ttatgttatt gaaaaaacaa
6301 acaaacaaaa actcctttat gatgatattc aacttgagtg gggtttttt tccactttgg
6361 tcctggatat aatgaaatga tacatattag gataaattt cactgtgtat agtagcaata
6421 cgaacacaca tgccaatgta tcaacatatc tacttggtta cattttggtt tatgataatt
6481 aaccttgatt catgtattgg gaagctacag ggactacgta atacctgctt atcacatagg
6541 aaaattatgt ccatgattct gagctccctt cttcaaaagt tcctcctgg gtgttctatg
6601 ttctctcttt atcctgaaat acatttatta ggttgtgagg tatgttgaag aagtagaagc
6661 caggggtatg ctttcagcat ttattgcaac caaaagttaa ccccatcacg gttaacgagc
6721 atctttggtc tcttgtggaa tttgaactaa aactatgagc cttattcaat atctataatt
6781 ctatgatttt tttaaattat gggaaattaa tgaaagatgt ttacatgaat aatgtttgcc
6841 cttactgtgt tatgaatgag ttttttgtag tgtgtctggg tgcatgatgc aagagagtag
6901 gaaaaatgtt tctgaaacaa aacttgacaa atatttgtaa tgaaagtaaa tttaaagatt
6961 gctataattg cgctatagaa acaatgcaag tattaaacaa aatatacaat ca
```

FIG. 15B

METHYLATED TAT POLYPEPTIDES AND METHODS OF USE THEREOF

CROSS-REFERENCE

This application claims the benefit of U.S. Provisional Patent Application No. 60/965,132, filed Aug. 17, 2007, which application is incorporated herein by reference in its entirety.

STATEMENT REGARDING FEDERALLY SPONSORED RESEARCH

This invention was made with Government support under Grant No. AI027763, awarded by the National Institutes of Health. The Government has certain rights in this invention.

BACKGROUND

The Tat protein of HIV-1 human immunodeficiency virus 1 (HIV-1) plays an essential role in HIV gene expression by promoting efficient transcriptional elongation of viral transcripts. Tat binds to TAR, a conserved RNA stem-loop structure present in the nascent viral transcripts. Tat binding to TAR involves a highly conserved arginine-rich motif (ARM) in Tat and recruits the positive transcription elongation factor (pTEFb) to elongating HIV transcripts. Tat and the cyclinT1 component of pTEFb bind TAR RNA cooperatively and induce phosphorylation of the C-terminal domain of RNA polymerase II by the cyclinT1-associated kinase CDK9.

Tat is subject to several posttranslational modifications, including acetylation, ubiquitination and arginine methylation. The modification that is best studied in Tat is acetylation of lysine 50 (K50). This residue located in the Tat ARM is recognized by the HAT activities of p300 and human GCN5. Tat acetylation at K50 activates Tat function and coordinates the functions of Tat in polymerase phosphorylation and chromatin reorganization. Acetylated Tat cannot interact with cyclinT1 and TAR RNA but binds instead to the PCAF HAT via the PCAF bromodomain. Acetylated Tat also interacts with the Brg-1 subunit of the SWI/SNF chromatin-remodeling complex. It has also demonstrated that K50 acetylation is reversed by the nicotinamide adenine dinucleotide (NAD+)-dependent human sirtuin 1 (SIRT1).

LITERATURE

Dorr et al. (2002) *EMBO J.* 21:2715-2723; Nishioka et al. (2002) *Genes Dev.* 16:479; U.S. Patent Publication No. 2004/0247614.

SUMMARY OF THE INVENTION

The present invention provides isolated methylated Tat peptides; and compositions comprising the peptides. The present invention further provides isolated antibodies specific for a Lys-51-methylated Tat polypeptide. Also provided are methods of identifying agents that inhibit Lys-51 methylation of a Tat polypeptide. The present invention further provides methods of treating an immunodeficiency virus infection in a mammalian subject.

BRIEF DESCRIPTION OF THE DRAWINGS

FIGS. 2A-C depict monomethylation of Tat at Lys-51 by Set9.

FIGS. 7A-C depict generation of polyclonal antibodies specific for K51-monomethylated Tat.

FIGS. 8A-C depict the role of Set9 as a positive cofactor for Tat transactivation.

FIG. 10 depicts a consensus Tat amino acid sequence (SEQ ID NO:1).

FIGS. 11A and 11B depict an alignment of Tat amino acid sequences.

FIGS. 12A and 12B depict an amino acid sequence (SEQ ID NO:31) and a nucleotide sequence (SEQ ID NO:32), respectively, of a human Set9.

FIG. 13 depicts an exemplary Tat-encoding nucleotide sequence (SEQ ID NO:29).

FIG. 14 depicts a nucleotide sequence of a Set9-encoding nucleic acid (SEQ ID NO:67).

FIGS. 15A and 15B depict a nucleotide sequence of a Set9-encoding nucleic acid (SEQ ID NO:68).

DEFINITIONS

Figures 1A, 1B:
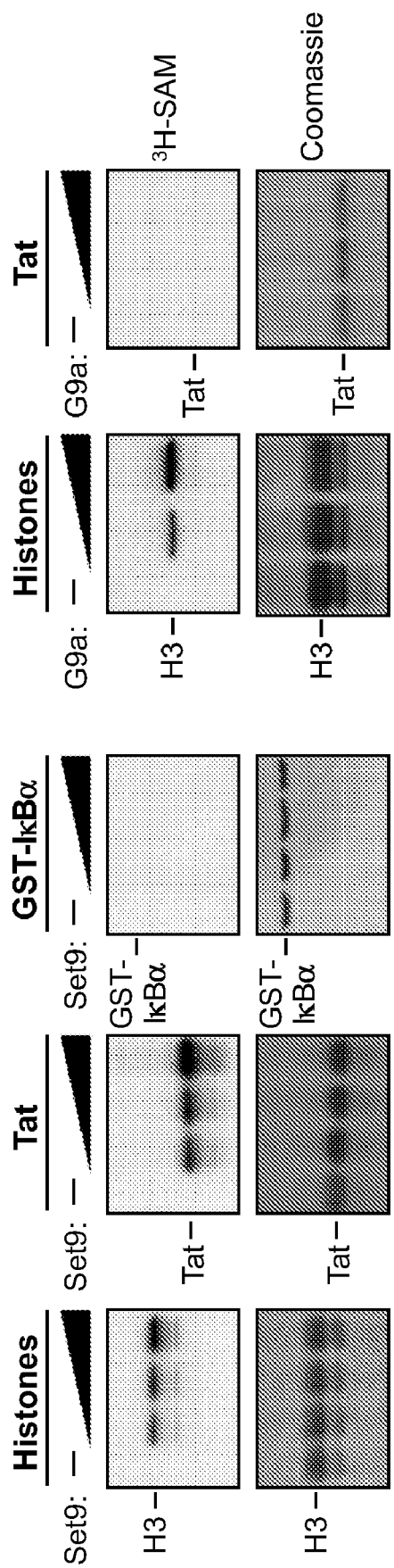
FIGS. 1A and 1B depict in vitro methylation of Tat by Set9.

The terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-59 is used.

A "substantially isolated" or "isolated" polypeptide or antibody is one that is substantially free of the materials with which it is associated in nature. By substantially free is meant at least 50%, at least 70%, at least 80%, or at least 90% free of the materials with which it is associated in nature. As used herein, an "isolated" polypeptide also refers to fusion polypeptides, which, by virtue of origin or manipulation: (1) are not associated with all or a portion of a polypeptide with which it is associated in nature, (2) are linked to a polypeptide other than that to which it is linked in nature, or (3) does not occur in nature. In some embodiments, an isolated polypeptide or an isolated antibody is at least about 70%, at least about 80%, at least about 90%, at least about 95%, or at least about 99%, or more, pure.

The term "binds specifically," in the context of antibody binding, refers to high avidity and/or high affinity binding of an antibody to a specific polypeptide i.e., epitope of a Lys-51-methylated Tat polypeptide. Antibody binding to an epitope on a specific methylated Tat polypeptide (also referred to herein as "a methylated Tat epitope") is stronger than binding of the same antibody to any other epitope, particularly those which may be present in molecules in association with, or in the same sample, as the specific polypeptide of interest, e.g., binds more strongly to a specific methylated Tat epitope than to a different methylated Tat epitope so that by adjusting binding conditions the antibody binds almost exclusively to the specific methylated Tat epitope and not to any other methylated Tat epitope, and not to any other Tat polypeptide which does not comprise the epitope.

Antibodies which bind specifically to a subject polypeptide may be capable of binding other polypeptides at a weak, yet detectable, level (e.g., 10% or less of the binding shown to the polypeptide of interest). Such weak binding, or background binding, is readily discernible from the specific antibody binding to a subject polypeptide, e.g. by use of appropriate controls. In general, antibodies of the invention which bind to a specific methylated Tat polypeptide with a binding affinity of $10^{-7}$ mole/l or more, e.g., $10^{-8}$ mole/l or more are said to bind specifically to the specific methylated Tat polypeptide. In general, an antibody with a binding affinity of $10^{-6}$ mole/liter or less is not useful in that it will not bind an antigen at a detectable level using conventional methodology currently used.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In the context of immunodeficiency virus infection, the term "treatment" encompasses prevention of establishment of a systemic infection following initial contact with the virus; and prophylactic treatment of an individual not yet infected with the virus.

The term "effective amount" or "therapeutically effective amount" means a dosage sufficient to provide for treatment for the disease state being treated or to otherwise provide the desired effect (e.g., induction of an effective immune response, reduction in serum viral load, etc.). The precise dosage will vary according to a variety of factors such as subject-dependent variables (e.g., age, immune system health, etc.), the disease (e.g., the particular immunodeficiency virus), and the treatment being effected. In the case of an immunodeficiency virus, an "effective amount" is that amount necessary to substantially improve the likelihood of treating the infection, in particular that amount which improves the likelihood of successfully preventing infection or eliminating infection when it has occurred.

The terms "individual," "host," "subject," and "patient," used interchangeably herein, refer to a mammal, including, but not limited to, murines, felines, simians, humans, mammalian farm animals, mammalian sport animals, and mammalian pets. The term includes mammals that are susceptible to infection by an immunodeficiency virus.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as CD4+ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like.

The term "immunodeficiency virus" as used herein, refers to human immunodeficiency virus-1 (HIV-1); human immunodeficiency virus-2 (HIV-2); any of a variety of HIV subtypes and quasispecies; simian immunodeficiency virus (SIV); and feline immunodeficiency virus (FIV).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a Lys-51-methylated Tat polypeptide" includes a plurality of such polypeptides and reference to "the Set9 methyltransferase" includes reference to one or more Set9 methyltransferases and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides isolated methylated Tat peptides; and compositions comprising the peptides. The present invention further provides isolated antibodies specific for a Lys-51-methylated Tat polypeptide. Also provided are methods of identifying agents that inhibit Lys-51 methylation of a Tat polypeptide. The present invention further provides methods of treating an immunodeficiency virus infection in a mammalian subject.

The present invention is based in part on the observation that human immunodeficiency virus-1 (HIV-1) transactivating regulatory protein (Tat) can be methylated at lysine-51 of the Tat protein. It was found that Lys-51 methylation activates Tat transactivation activity at the HIV promoter. It was also found that the methyltransferase Set9 methylates Lys-51 of Tat.

Isolated Methylated Tat Polypeptides

The present invention provides isolated, methylated Tat polypeptides comprising amino acid sequences corresponding to a portion of a Tat polypeptide comprising a methylated lysine-51 (Lys-51). A subject isolated methylated Tat polypeptide is useful for various applications, including, e.g., generating antibody to a methylated Tat polypeptide; in methods of identifying agents that inhibit the methyltransferase activity of an enzyme that catalyzes transfer of a methyl group to Lys-51 of a Tat polypeptide; in methods of treating an infection with an immunodeficiency virus; and in methods of detecting, e.g., in a biological sample obtained from an individual, the presence of antibody specific for $Lys^{51}$ methylated Tat polypeptide.

In some embodiments, a subject isolated, methylated Tat polypeptide comprises a methylated lysine at a position corresponding to Lys-51 of the amino acid sequence set forth in SEQ ID NO:1. For example, in some embodiments, a subject isolated, methylated Tat polypeptide comprises the amino acid sequence SYGRK$K^{Me}$RRQR (SEQ ID NO:2), or a variation thereof, where the methylated lysine is monomethylated, dimethylated, or trimethylated. In some embodiments, a subject isolated, methylated Tat polypeptide comprises, in addition to a methylated lysine at a position corresponding to Lys-51 of the amino acid sequence set forth in SEQ ID NO:1, an acetylated lysine at a position corresponding to Lys-50 of the amino acid sequence set forth in SEQ ID NO:1. For example, in some embodiments, a subject isolated, methylated Tat polypeptide comprises the amino acid sequence SYGR$K^{Ac}K^{Me}$RRQR (SEQ ID NO:3), or a variation thereof, where the methylated lysine is monomethylated, dimethylated, or trimethylated.

In some embodiments, a subject isolated, methylated Tat polypeptide does not include a methylated arginine, e.g., in some embodiments, a subject isolated, methylated Tat polypeptide does not include a methylated arginine at a position corresponding to Arg-52 and/or Arg-53 of the amino acid sequence set forth in SEQ ID NO:1. For example, in some embodiments, a subject isolated, methylated Tat polypeptide comprises the amino acid sequence SYGRK$K^{Me}$RRQR (SEQ ID NO:2), or a variation thereof, or the amino acid sequence SYGR$K^{Ac}K^{Me}$RRQR (SEQ ID NO:3), or a variation thereof, where one or both of the arginine residues immediately carboxyl-terminal to the methylated lysine are not methylated.

In other embodiments, a subject isolated, methylated Tat polypeptide includes a methylated arginine, e.g., in some embodiments, a subject isolated, methylated Tat polypeptide includes a methylated arginine at a position corresponding to Arg-52 and/or Arg-53 of the amino acid sequence set forth in SEQ ID NO:1. For example, in some embodiments, a subject isolated, methylated Tat polypeptide comprises: the amino acid sequence SYGRK$K^{Me}R^{Me}$RQR (SEQ ID NO:33), or a variation thereof; the amino acid sequence SYGR$K^{Ac}$ $K^{Me}R^{Me}$RQR (SEQ ID NO:34), or a variation thereof; the amino acid sequence SYGRK$K^{Me}R^{Me}R^{Me}$QR (SEQ ID NO:35), or a variation thereof; or SYGR$K^{Ac}K^{Me}R^{Me}R^{Me}$QR (SEQ ID NO:36), or a variation thereof. In some embodiments, the methylated arginine is monomethylated. In other embodiments, the methylated arginine is dimethylated. In some embodiments, a dimethylated arginine is asymmetric dimethylarginine (ADMA). In other embodiments, a dimethylated arginine is symmetric dimethylarginine (SDMA).

In some embodiments, a subject isolated, methylated Tat polypeptide comprises an amino acid sequence having at least about 75%, at least about 80%, at least about 85%, at least about 90%, at least about 95%, at least about 98%, at least about 99%, or 100% amino acid sequence identity to amino acids 46 to 55 of SEQ ID NO:1 (FIG. 10), where the methylated Tat polypeptide comprises a methylated Lys ($K^{Me}$) at a position corresponding to Lys-51 of SEQ ID NO:1. In some embodiments, a subject isolated, methylated Tat polypeptide comprises an amino acid sequence having at least about 75%, at least about 80%, at least about 85%, at least about 90%, at least about 95%, at least about 98%, at least about 99%, or 100% amino acid sequence identity to amino acids 46 to 55 of SEQ ID NO:1 (FIG. 10), where the methylated Tat polypeptide comprises a methylated lysine ($K^{Me}$) corresponding to Lys-51 of SEQ ID NO:1, and where the methylated Tat polypeptide comprises an acetylated lysine ($K^{Ac}$) at a position corresponding to Lys-50 of SEQ ID NO:1.

As noted above, a subject isolated, methylated Tat polypeptide can be isolated from a naturally-occurring source of Tat polypeptide; or can be synthesized. A subject isolated, methylated Tat polypeptide can comprise amino acid sequences found in any of a variety of Tat polypeptides. The amino acid sequences of HIV Tat polypeptides are known, and any of these sequences can be included in a subject acetylated Tat polypeptide. Numerous HIV Tat protein amino acid sequences are found under GenBank, and any of these publicly available sequences can be used in the present invention. Exemplary, non-limiting, HIV Tat protein amino acid sequences are found under GenBank Accession Nos. AAO26250, AAO26252, AAO26254, AAO26258, AAO26260, AAO26262, AAO26264, AAO26266, AAO26268, AAO26270, AAO26272, AAO26274, AAO26276, AAO26278, AAO26280, AAO26282, AAO26284, AAO26286, AAO26288, AAO26290, AAO26292, AAO26294, AAO26296, AAO26298, AAO26300, AAO26302, AAO26304, AAO26306, AAO26308; AAB50256; AAL12204; AAL12195; AAL12186; AAL12177; AAN47131; AAN47122; AAN47113; AAN47104; AAN03332; AAN03323; AAN03314; AAN03305; AAN03296; AAN03287; AAN03278; AAN31592; AAN64126; AAN64117; AAN64108; AAN64099; AAN64090; AAN64080; K02013; AAL29460; and as shown in FIGS. 11A and 11B (SEQ ID NOs:44-66; and consensus Tat sequence SEQ ID NO:1). Additional HIV Tat amino acid sequences are found in Peloponese et al. (1999) *J. Biol. Chem.* 274:11473-11478; and Goldstein (1996) *Nat. Med.* 2:960-964.

As noted above, the designation "$K^{Me}$" is methylated lysine. The designation "$K^{Me}$" refers to mono-methylated lysine, di-methylated lysine, or tri-methylated lysine. As such, in any of the embodiments described herein, a subject isolated, methylated Tat polypeptide can comprises a lysine corresponding to Lys-51 of a full-length Tat polypeptide (e.g., Lys-51 of SEQ ID NO:1), where the lysine can be mono-methylated, di-methylated, or tri-methylated.

In some embodiments, a subject isolated, methylated Tat polypeptide has a length of from about 10 amino acids to about 50 amino acids, e.g., in some embodiments, a subject isolated, methylated Tat polypeptide has a length of 10 amino acids (aa) to 15 aa (e.g., 10 aa, 11 aa, 12 aa, 13 aa, 14 aa, or 15 aa), 15 aa to 20 aa (e.g., 15 aa, 16 aa, 17 aa, 18 aa, 19 aa, or 20 aa), 20 aa to 25 aa (e.g., 20 aa, 21 aa, 22 aa, 23 aa, 24 aa, or 25 aa), 25 aa to 30 aa, 30 aa to 35 aa, 35 aa to 40 aa, 40 aa to 45 aa, or 45 aa to 50 aa.

For example, in some embodiments, a subject isolated, methylated Tat polypeptide comprises the amino acid sequence SYGRKK$^{Me}$RRQR (SEQ ID NO:2), and has a length of 10 aa to about 50 aa, e.g., from 10 aa to 15 aa, from 15 aa to 20 aa, from 20 aa to 25 aa, from 25 aa to 30 aa, from 30 aa to 40 aa, from 40 aa to 45 aa, or from 45 aa to 50 aa. In some embodiments, a subject isolated, methylated Tat polypeptide comprises the amino acid sequence SYGRK$^{Ac}$K$^{Me}$RRQR (SEQ ID NO:3), and has a length of 10 aa to about 50 aa, e.g., from 10 aa to 15 aa, from 15 aa to 20 aa, from 20 aa to 25 aa, from 25 aa to 30 aa, from 30 aa to 40 aa, from 40 aa to 45 aa, or from 45 aa to 50 aa.

In other embodiments, a subject isolated, methylated Tat polypeptide comprises the amino acid sequence ISYGRKK$^{Me}$RRQR (SEQ ID NO:4), and has a length of 11 aa to about 50 aa, e.g., from 11 aa to 15 aa, from 15 aa to 20 aa, from 20 aa to 25 aa, from 25 aa to 30 aa, from 30 aa to 40 aa, from 40 aa to 45 aa, or from 45 aa to 50 aa. In other embodiments, a subject isolated, methylated Tat polypeptide comprises the amino acid sequence ISYGRK$^{Ac}$K$^{Me}$RRQR (SEQ ID NO:5), and has a length of 11 aa to about 50 aa, e.g., from 11 aa to 15 aa, from 15 aa to 20 aa, from 20 aa to 25 aa, from 25 aa to 30 aa, from 30 aa to 40 aa, from 40 aa to 45 aa, or from 45 aa to 50 aa.

In other embodiments, a subject isolated, methylated Tat polypeptide comprises the amino acid sequence SYGRKK$^{Me}$RRQRR (SEQ ID NO:6), and has a length of 11 aa to about 50 aa, e.g., from 11 aa to 15 aa, from 15 aa to 20 aa, from 20 aa to 25 aa, from 25 aa to 30 aa, from 30 aa to 40 aa, from 40 aa to 45 aa, or from 45 aa to 50 aa. In other embodiments, a subject isolated, methylated Tat polypeptide comprises the amino acid sequence SYGRK$^{Ac}$K$^{Me}$RRQRR (SEQ ID NO:7), and has a length of 11 aa to about 50 aa, e.g., from 11 aa to 15 aa, from 15 aa to 20 aa, from 20 aa to 25 aa, from 25 aa to 30 aa, from 30 aa to 40 aa, from 40 aa to 45 aa, or from 45 aa to 50 aa.

In other embodiments, a subject isolated, methylated Tat polypeptide comprises the amino acid sequence SYGRKK$^{Me}$RRQRQ (SEQ ID NO:8), and has a length of 11 aa to about 50 aa, e.g., from 11 aa to 15 aa, from 15 aa to 20 aa, from 20 aa to 25 aa, from 25 aa to 30 aa, from 30 aa to 40 aa, from 40 aa to 45 aa, or from 45 aa to 50 aa. In other embodiments, a subject isolated, methylated Tat polypeptide comprises the amino acid sequence SYGRK$^{Ac}$K$^{Me}$RRQRQ (SEQ ID NO:9), and has a length of 11 aa to about 50 aa, e.g., from 11 aa to 15 aa, from 15 aa to 20 aa, from 20 aa to 25 aa, from 25 aa to 30 aa, from 30 aa to 40 aa, from 40 aa to 45 aa, or from 45 aa to 50 aa.

In other embodiments, a subject isolated, methylated Tat polypeptide comprises the amino acid sequence ISYGRKK$^{Me}$RRQRR (SEQ ID NO:10), and has a length of 12 aa to about 50 aa, e.g., from 12 aa to 15 aa, from 15 aa to 20 aa, from 20 aa to 25 aa, from 25 aa to 30 aa, from 30 aa to 40 aa, from 40 aa to 45 aa, or from 45 aa to 50 aa. In other embodiments, a subject isolated, methylated Tat polypeptide comprises the amino acid sequence ISYGRK$^{Ac}$K$^{Me}$RRQRR (SEQ ID NO:11), and has a length of 12 aa to about 50 aa, e.g., from 12 aa to 15 aa, from 15 aa to 20 aa, from 20 aa to 25 aa, from 25 aa to 30 aa, from 30 aa to 40 aa, from 40 aa to 45 aa, or from 45 aa to 50 aa.

In other embodiments, a subject isolated, methylated Tat polypeptide comprises the amino acid sequence ISYGRKK$^{Me}$RRQRQ (SEQ ID NO:12), and has a length of 12 aa to about 50 aa, e.g., from 12 aa to 15 aa, from 15 aa to 20 aa, from 20 aa to 25 aa, from 25 aa to 30 aa, from 30 aa to 40 aa, from 40 aa to 45 aa, or from 45 aa to 50 aa. In other embodiments, a subject isolated, methylated Tat polypeptide comprises the amino acid sequence ISYGRK$^{Ac}$K$^{Me}$RRQRQ (SEQ ID NO:13), and has a length of 12 aa to about 50 aa, e.g., from 12 aa to 15 aa, from 15 aa to 20 aa, from 20 aa to 25 aa, from 25 aa to 30 aa, from 30 aa to 40 aa, from 40 aa to 45 aa, or from 45 aa to 50 aa.

In other embodiments, a subject isolated, methylated Tat polypeptide comprises the amino acid sequence ISYGRKK$^{Me}$RRQRRR (SEQ ID NO:14), and has a length of 13 aa to about 50 aa, e.g., from 13 aa to 15 aa, from 15 aa to 20 aa, from 20 aa to 25 aa, from 25 aa to 30 aa, from 30 aa to 40 aa, from 40 aa to 45 aa, or from 45 aa to 50 aa. In other embodiments, a subject isolated, methylated Tat polypeptide comprises the amino acid sequence ISYGRK$^{Ac}$K$^{Me}$RRQRRR (SEQ ID NO:15), and has a length of 13 aa to about 50 aa, e.g., from 13 aa to 15 aa, from 15 aa to 20 aa, from 20 aa to 25 aa, from 25 aa to 30 aa, from 30 aa to 40 aa, from 40 aa to 45 aa, or from 45 aa to 50 aa.

In other embodiments, a subject isolated, methylated Tat polypeptide comprises the amino acid sequence ISYGRKK$^{Me}$RRQRRG (SEQ ID NO:16), and has a length of 13 aa to about 50 aa, e.g., from 13 aa to 15 aa, from 15 aa to 20 aa, from 20 aa to 25 aa, from 25 aa to 30 aa, from 30 aa to 40 aa, from 40 aa to 45 aa, or from 45 aa to 50 aa. In other embodiments, a subject isolated, methylated Tat polypeptide comprises the amino acid sequence ISYGRK$^{Ac}$K$^{Me}$RRQRRG (SEQ ID NO:17), and has a length of 13 aa to about 50 aa, e.g., from 13 aa to 15 aa, from 15 aa to 20 aa, from 20 aa to 25 aa, from 25 aa to 30 aa, from 30 aa to 40 aa, from 40 aa to 45 aa, or from 45 aa to 50 aa.

In other embodiments, a subject isolated, methylated Tat polypeptide comprises the amino acid sequence ISYGRKK$^{Me}$RRQRRK (SEQ ID NO:18), and has a length of 13 aa to about 50 aa, e.g., from 13 aa to 15 aa, from 15 aa to 20 aa, from 20 aa to 25 aa, from 25 aa to 30 aa, from 30 aa to 40 aa, from 40 aa to 45 aa, or from 45 aa to 50 aa. In other embodiments, a subject isolated, methylated Tat polypeptide comprises the amino acid sequence ISYGRK$^{Ac}$K$^{Me}$RRQRRK (SEQ ID NO:19), and has a length of 13 aa to about 50 aa, e.g., from 13 aa to 15 aa, from 15 aa to 20 aa, from 20 aa to 25 aa, from 25 aa to 30 aa, from 30 aa to 40 aa, from 40 aa to 45 aa, or from 45 aa to 50 aa.

In other embodiments, a subject isolated, methylated Tat polypeptide has a length of from about 50 amino acids to about 105 amino acids, e.g., from about 50 aa to about 55 aa, from about 55 aa to about 60 aa, from about 60 aa to about 65 aa, from about 65 aa to about 70 aa, from about 70 aa to about 75 aa, from about 75 aa to about 80 aa, from about 80 aa to about 85 aa, from about 85 aa to about 90 aa, from about 90 aa to about 95 aa, from about 95 aa to about 100 aa, or from about 100 aa to about 105 aa; where the isolated, methylated Tat polypeptide comprises a methylated Lys at a position corresponding to Lys-51 of SEQ ID NO:1; and where the isolated, methylated Tat polypeptide comprises an amino acid sequence having at least about 75%, at least about 80%, at least about 85%, at least about 90%, at least about 95%, at least about 98%, at least about 99%, or 100% amino acid sequence identity to the amino acid sequence set forth in SEQ ID NO:1 (FIG. 10). In some embodiments, a subject isolated, methylated Tat polypeptide has a length of from about 50 amino acids to about 105 amino acids, e.g., from about 50 aa to about 55 aa, from about 55 aa to about 60 aa, from about 60 aa to about 65 aa, from about 65 aa to about 70 aa, from about 70 aa to about 75 aa, from about 75 aa to about 80 aa, from about 80 aa to about 85 aa, from about 85 aa to about 90 aa, from about 90 aa to about 95 aa, from about 95 aa to about 100 aa, or from about 100 aa to about 105 aa; where the isolated, methylated Tat polypeptide comprises a methylated Lys at a position corresponding to Lys-51 of SEQ ID NO:1, and an acetylated Lys at a position corresponding to Lys-50 of SEQ ID NO:1; where the isolated, methylated Tat polypeptide comprises a methylated Lys at a position corresponding to Lys-51 of SEQ ID NO:1; and where the isolated, methylated Tat polypeptide comprises an amino acid sequence having at least about 75%, at least about 80%, at least about 85%, at least about 90%, at least about 95%, at least about 98%, at least about 99%, or 100% amino acid sequence identity to the amino acid sequence set forth in SEQ ID NO:1 (FIG. 10).

In some embodiments, a subject isolated, methylated Tat polypeptide has a length of from about 50 amino acids to about 105 amino acids, e.g., from about 50 aa to about 55 aa, from about 55 aa to about 60 aa, from about 60 aa to about 65 aa, from about 65 aa to about 70 aa, from about 70 aa to about 75 aa, from about 75 aa to about 80 aa, from about 80 aa to about 85 aa, from about 85 aa to about 90 aa, from about 90 aa to about 95 aa, from about 95 aa to about 100 aa, or from about 100 aa to about 105 aa; and comprises an amino acid sequence as set forth in one of SEQ ID NOs:2-19.

In other embodiments, a subject isolated, methylated Tat polypeptide has a length of from about 50 amino acids to about 105 amino acids, e.g., from about 50 aa to about 55 aa, from about 55 aa to about 60 aa, from about 60 aa to about 65 aa, from about 65 aa to about 70 aa, from about 70 aa to about 75 aa, from about 75 aa to about 80 aa, from about 80 aa to about 85 aa, from about 85 aa to about 90 aa, from about 90 aa to about 95 aa, from about 95 aa to about 100 aa, or from about 100 aa to about 105 aa; and comprises the amino acid sequence GISYGRKK$^{Me}$RRQRRRP (SEQ ID NO:20). In other embodiments, a subject isolated, methylated Tat polypeptide has a length of from about 50 amino acids to about 105 amino acids, e.g., from about 50 aa to about 55 aa, from about 55 aa to about 60 aa, from about 60 aa to about 65 aa, from about 65 aa to about 70 aa, from about 70 aa to about 75 aa, from about 75 aa to about 80 aa, from about 80 aa to about 85 aa, from about 85 aa to about 90 aa, from about 90 aa to about 95 aa, from about 95 aa to about 100 aa, or from about 100 aa to about 105 aa; and comprises the amino acid sequence GISYGRK$^{Ac}$K$^{Me}$RRQRRRP (SEQ ID NO:21).

In other embodiments, a subject isolated, methylated Tat polypeptide has a length of from about 50 amino acids to about 105 amino acids, e.g., from about 50 aa to about 55 aa, from about 55 aa to about 60 aa, from about 60 aa to about 65 aa, from about 65 aa to about 70 aa, from about 70 aa to about 75 aa, from about 75 aa to about 80 aa, from about 80 aa to about 85 aa, from about 85 aa to about 90 aa, from about 90 aa to about 95 aa, from about 95 aa to about 100 aa, or from about 100 aa to about 105 aa; and comprises the amino acid sequence KGISYGRKK$^{Me}$RRQRRRPP (SEQ ID NO:22). In other embodiments, a subject isolated, methylated Tat polypeptide has a length of from about 50 amino acids to about 105 amino acids, e.g., from about 50 aa to about 55 aa, from about 55 aa to about 60 aa, from about 60 aa to about 65 aa, from about 65 aa to about 70 aa, from about 70 aa to about 75 aa, from about 75 aa to about 80 aa, from about 80 aa to about 85 aa, from about 85 aa to about 90 aa, from about 90 aa to about 95 aa, from about 95 aa to about 100 aa, or from about 100 aa to about 105 aa; and comprises the amino acid sequence KGISYGRK$^{Ac}$K$^{Me}$RRQRRRPP (SEQ ID NO:23).

In other embodiments, a subject isolated, methylated Tat polypeptide has a length of from about 50 amino acids to about 105 amino acids, e.g., from about 50 aa to about 55 aa, from about 55 aa to about 60 aa, from about 60 aa to about 65 aa, from about 65 aa to about 70 aa, from about 70 aa to about 75 aa, from about 75 aa to about 80 aa, from about 80 aa to about 85 aa, from about 85 aa to about 90 aa, from about 90 aa to about 95 aa, from about 95 aa to about 100 aa, or from about 100 aa to about 105 aa; and comprises the amino acid sequence (A/G)KGISYGRKK$^{Me}$RRQRRRPPQ (SEQ ID NO:24). In other embodiments, a subject isolated, methylated Tat polypeptide has a length of from about 50 amino acids to about 105 amino acids, e.g., from about 50 aa to about 55 aa, from about 55 aa to about 60 aa, from about 60 aa to about 65 aa, from about 65 aa to about 70 aa, from about 70 aa to about 75 aa, from about 75 aa to about 80 aa, from about 80 aa to about 85 aa, from about 85 aa to about 90 aa, from about 90 aa to about 95 aa, from about 95 aa to about 100 aa, or from about 100 aa to about 105 aa; and comprises the amino acid sequence (A/G)KGISYGRK$^{Ac}$K$^{Me}$RRQRRRPPQ (SEQ ID NO:25).

In some embodiments, a subject isolated, methylated Tat polypeptide has a length greater than about 105 amino acids, and where the isolated, methylated Tat polypeptide comprises a methylated Lys at a position corresponding to Lys-51 of SEQ ID NO:1; and where the isolated, methylated Tat polypeptide comprises an amino acid sequence having at least about 75%, at least about 80%, at least about 85%, at least about 90%, at least about 95%, at least about 98%, at least about 99%, or 100% amino acid sequence identity to the amino acid sequence set forth in SEQ ID NO:1 (FIG. 10). In some embodiments, a subject isolated, methylated Tat polypeptide has a length greater than about 105 amino acids, where the isolated, methylated Tat polypeptide comprises a methylated Lys at a position corresponding to Lys-51 of SEQ ID NO:1 and comprises an acetylated Lys at a position corresponding to Lys-50 of SEQ ID NO:1; and where the isolated, methylated Tat polypeptide comprises an amino acid sequence having at least about 75%, at least about 80%, at least about 85%, at least about 90%, at least about 95%, at least about 98%, at least about 99%, or 100% amino acid sequence identity to the amino acid sequence set forth in SEQ ID NO:1 (FIG. 10).

In some embodiments, a subject isolated, methylated Tat polypeptide includes one or more additional amino acids not found in a naturally-occurring Tat polypeptide. Such amino acids include amino acids added to the amino-terminus and/or the carboxyl-terminus of a subject isolated methylated Tat polypeptide. Amino acids added to a subject isolated methylated Tat polypeptide include amino acids that serve as linkers, e.g., to a carrier polypeptide or other polypeptide. Linking can be performed to any amino acid that contains an active group, including, but not limited to, amino acids with a free NH$_2$ group, e.g., lysine, arginine, asparagine, and glutamine; a free NH$_2$ group of an amino terminal amino acid; amino acids with sulfhydryl groups, e.g., cysteine, or an amino acid to which an SH$_2$ group has been chemically added; amino acids with carboxyl groups, e.g., aspartic acid, glutamic acid; and a COOH group of a carboxyl-terminal amino acid.

In some embodiments, a subject isolated methylated Tat polypeptide includes one or more additional cysteine residue appended to the C-terminus. A cysteine residue serves as a linkage site for linking to a carrier. For example, a subject isolated methylated Tat polypeptide includes any one of SEQ ID NOs:2-25 with one, two, three, or more additional cysteines on the C-terminus.

Fusion Proteins

In some embodiments, a subject isolated, methylated Tat polypeptide includes heterologous amino acid sequences, e.g., a subject isolated, methylated Tat polypeptide may be a fusion protein that comprises a methylated Tat polypeptide and a fusion partner, where the fusion partner is a heterologous polypeptide (e.g., a polypeptide other than Tat). Heterologous polypeptides are polypeptides other than Tat, and include, but are not limited to, polypeptide carriers (discussed in more detail below); immunological tags such as epitope tags, including, but not limited to, hemagglutinin (e.g., CYPYDVPDYA; SEQ ID NO:37), FLAG (e.g., DYKDDDDK; SEQ ID NO:38), c-myc (EQKLISEEDL; SEQ ID NO:39) and the like; proteins that provide for a detectable signal, including, but not limited to, fluorescent proteins, enzymes (e.g., β-galactosidase, alkaline phosphatase, luciferase, horse radish peroxidase, etc.), and the like; polypeptides that facilitate purification or isolation of the fusion protein, e.g., metal ion binding polypeptides such as 6H is tags (e.g., acetylated Tat/6His), glutathione-S-transferase; polypeptides that facilitate transport across a eukaryotic cell membrane; and the like.

Suitable fluorescent proteins include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like. Where the fusion partner is an enzyme that yields a detectable product, the product can be detected using an appropriate means, e.g., β-galactosidase can, depending on the substrate, yield colored product, which is detected spectrophotometrically, or a fluorescent product; luciferase can yield a luminescent product detectable with a luminometer; etc.

In some embodiments, a methylated Tat polypeptide is detectably labeled. Various labels include radioisotopes, fluorescers (e.g., fluorescent dyes), chemiluminescers, enzymes, a member of a specific binding pair, particles, e.g. magnetic particles, and the like. Specific binding pairs include, but are not limited to, biotin and streptavidin; digoxin and antidigoxin; lectin and carbohydrate moieties; antibody and hapten; antibody and antigen; etc.

Multimers

In some embodiments, a subject methylated Tat polypeptide is multimerized, e.g., two or more methylated Tat polypeptides are linked in tandem. Multimers include dimers, trimers, tetramers, pentamers, etc. Monomeric methylated Tat polypeptides are linked to one another directly or via a linker. Thus, in some embodiments, a subject methylated Tat polypeptide has the formula X—(Y)$_{0-40}$—X, where X is a methylated Tat polypeptide, and Y is a linker. Where a linker is used, Y is one or more amino acids, or other linking groups.

Where Y is a spacer peptide, it is generally of a flexible nature, although other chemical linkages are not excluded. Suitable linker peptides include peptides of between about 2 and about 40 amino acids in length, e.g., from about 2 amino acids to about 10 amino acids, from about 10 amino acids to about 20 amino acids, or from about 6 amino acids to about 25 amino acids in length. These linkers can be produced by using synthetic, linker-encoding oligonucleotides to couple the proteins. Peptide linkers with a degree of flexibility are suitable for use. The linking peptides may have virtually any amino acid sequence, where in some embodiments the linker peptides will have a sequence that results in a generally flexible peptide. The use of small amino acids, such as glycine and alanine, are of use in creating a flexible peptide. Exemplary peptide linkers include (Gly)$_{2-40}$, (Ser)$_{2-40}$, and (Ala)$_{2-40}$. The creation of such sequences is routine to those of skill in the art. A variety of different linkers are commercially available and are considered suitable for use according to the present invention.

Amino acid sequences rich in alanine and proline residues are known to impart flexibility to multi-domain protein structures. For example, such sequences link the domains of the so-called E2 components of the 2-oxo acid dehydrogenase complexes, such as pyruvate dehydrogenase complex and 2-oxo glutarate dehydrogenase complex. Alanine-proline rich regions are also found in myosin light chains. Exemplary linkers for use in the invention have a combination of serine, glycine, and alanine residues, where an exemplary linker is GGGSGG (SEQ ID NO:40). However, any flexible linker generally between about 2 amino acids and about 40 amino acids, e.g., from about 6 amino acids to about 10 amino acids in length may be used. Linkers may have virtually any sequence that results in a generally flexible peptide.

Linkages for homo- or hetero-polymers or for coupling to carriers can be provided in a variety of ways. For example, cysteine residues can be added at both the amino- and carboxyl-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, Immun. Rev. 62:185 (1982). Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl)cyclohexane-1-carboxylic acid and the like. The carboxyl groups can be activated by combining them with succinimide or 1-hydroxy-2-nitro-4-sulfonic acid, sodium salt. An exemplary coupling agent is succinimidyl 4-(N-maleimidomethyl)cyclohexane-1-carboxylate (SMCC). Of course, it will be understood that linkage should not substantially interfere with either of the linked groups to function as an immunogen.

Carriers

In some embodiments, a subject methylated Tat polypeptide is linked to a carrier. The term "linked," as used herein interchangeably with the term "coupled," refers to proximately associated, e.g., the methylated Tat polypeptide and the carrier are in close spatial proximity. In some embodiments, the linkage is a covalent linkage. In other embodiments, the linkage is a non-covalent linkage. In some embodiments, the methylated Tat polypeptide is linked directly to the carrier. In other embodiments, the methylated Tat polypeptide is linked indirectly, e.g., via a linker molecule.

Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactivated virus particles; inactivated bacterial toxins such as toxoid from diphtheria, tetanus, cholera, leukotoxin molecules; liposomes; inactivated bacteria; dendritic cells; and the like. Carriers are described in further detail below.

Suitable carriers are well known in the art, and include, e.g., thyroglobulin, albumins such as human serum albumin, tetanus toxoid; Diphtheria toxoid; polyamino acids such as poly(D-lysine:D-glutamic acid); VP6 polypeptides of rotaviruses; influenza virus hemagglutinin, influenza virus nucleoprotein; hepatitis B virus core protein, hepatitis B virus surface antigen; purified protein derivative (PPD) of tuberculin from *Mycobacterium tuberculosis*; inactivated *Pseudomonas aeruginosa* exotoxin A (toxin A); Keyhole Limpet Hemocyanin (KLH); filamentous hemagglutinin (FHA) of *Bordetella pertussis*; T helper cell (Th) epitopes of tetanus toxoid (TT) and *Bacillus* Calmette-Guerin (BCG) cell wall; recombinant 10 kDa, 19 kDa and 30-32 kDa proteins from *M. leprae* or from *M. tuberculosis*, or any combination of these proteins; and the like. See, e.g., U.S. Pat. No. 6,447,778 for a discussion of carriers and methods of conjugating peptides to carriers.

*Pseudomonas aeruginosa* exotoxin A (toxin A) has been used effectively as a carrier in conjugate vaccines. *Pseudomonas aeruginosa* exotoxin A may be purified from the supernatant of fermentor-grown cultures of *Pseudomonas aeruginosa* PA 103. Toxin A has been classified as a superantigen based upon results in animals. Toxin A can be completely and irreversibly detoxified by covalent coupling to adipic acid dihydrazide (ADH), a 4 carbon spacer molecule. This step destroys the ADPR-transferase activity of the toxin molecule, hence rendering it nontoxic. The non-reacted hydrazide group can be used to covalently couple a polypeptide to toxin A. Toxin A may also be coupled to a polypeptide using a carbodiimide reagent.

PPD-peptide conjugates are conveniently prepared with glutaraldehyde as coupling agent. See, e.g., Rubinstein et al. (1995) *AIDS* 9:243-51.

The methods by which a subject polypeptide is conjugated with a carrier include disulfide linkages through a C terminal peptide cysteine linkage, coupling with glutaraldehyde solution for two hours, coupling with tyrosine, or coupling with water soluble carbodiimide.

In some embodiments, a subject methylated Tat polypeptide is lipidated. Lipidation increases a cytotoxic T cell (CTL) response to the peptide that is linked to the lipid. The lipid residue, such as palmitic acid or the like, is attached to the amino terminus of the peptide. The lipid can be attached directly to the peptide, or, indirectly via a linkage, such as a Ser-Ser, Gly, Gly-Gly, Ser linkage or the like. As another example, *E. coli* lipoprotein, such as tripalmitoyl-S-glyceryl-cysteinyl-seryl-serine ($P_3$ CSS), can be used to prime specific CTL when covalently attached to the peptide. See, Deres et al., *Nature* 342:561-564 (1989). A subject methylated Tat polypeptide can be conjugated with uncharged fatty acid residues of different chain lengths and degrees of unsaturation, ranging from acetic to stearic acid as well as to negatively charged succinyl residues via the appropriate carboxylic acid anhydrides. See, e.g., U.S. Pat. No. 6,419,931.

A subject Tat polypeptide may be conjugated directly or indirectly, e.g., via a linker molecule, to a carrier. A wide variety of linker molecules are known in the art and can be used in the conjugates. The linkage from the peptide to the carrier may be through a peptide reactive side chain, or the N- or C-terminus of the peptide. A linker may be an organic, inorganic, or semi-organic molecule, and may be a polymer of an organic molecule, an inorganic molecule, or a co-polymer comprising both inorganic and organic molecules.

If present, the linker molecules are generally of sufficient length to permit the methylated Tat polypeptide and a linked carrier to allow some flexible movement between the methylated Tat polypeptide and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Preparation of a Subject Methylated Tat Polypeptide

A subject methylated Tat polypeptide may be synthesized chemically or enzymatically, may be produced recombinantly, may be isolated from a natural source, or a combination of the foregoing. A subject methylated Tat polypeptide may be isolated from natural sources using standard methods of protein purification known in the art, including, but not limited to, high performance liquid chromatography, exclusion chromatography, gel electrophoresis, affinity chromatography, or other purification technique. One may employ solid phase peptide synthesis techniques, where such techniques are known to those of skill in the art. See Jones, *The Chemical Synthesis of Peptides* (Clarendon Press, Oxford) (1994). Generally, in such methods a peptide is produced through the sequential additional of activated monomeric units to a solid phase bound growing peptide chain. Peptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co. (1984); Tam et al., J. Am. Chem. Soc. 105:6442 (1983); Merrifield, Science 232:341-347 (1986); and Barany and Merrifield, The Peptides, Gross and Meienhofer, eds., Academic Press, New York, pp. 1-284 (1979), each of which is incorporated herein by reference. Well-established recombinant DNA techniques can be employed for production of a subject polypeptide.

For production of a subject methylated Tat polypeptide by recombinant means, the polynucleotide comprising a nucleotide sequence encoding Tat ("a Tat polynucleotide") is expressed in any convenient expression system, including, for example, bacterial, yeast, insect, amphibian and mammalian systems. Suitable vectors and host cells are described in U.S. Pat. No. 5,654,173. In the expression vector, a Tat polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present.

Expression cassettes may be prepared comprising a transcription initiation region, the gene or fragment thereof, and a transcriptional termination region. After introduction of the expression cassette containing a Tat polynucleotide, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, e.g. COS 7 cells, HEK 293, CHO, Xenopus oocytes, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function. Specific expression systems of interest include bacterial, yeast, insect cell and mammalian cell derived expression systems, which expression systems are well known in the art.

In some embodiments, the Tat polypeptide is methylated in a cell-free reaction in vitro, either after synthesis or during synthesis, or, e.g., after isolation from a naturally-occurring source of a Tat polypeptide. For example, a Tat polypeptide is contacted with a SET domain-containing polypeptide (e.g., Set9) in a buffer containing 50 mM Tris-HCl (pH 8.5), 5 mM $MgCl_2$, 4 mM dithiothreitol (DTT) and S-adenosyl methionine (SAM).

The SET domain-containing polypeptide that is used need only be capable of methylating lysine at a position corresponding to Lys-51 of a Tat polypeptide, e.g., a Tat polypeptide comprising the amino acid sequence set forth in SEQ ID NO:1. For example, in some embodiments, a suitable SET domain-containing polypeptide is capable of methylating a peptide of the sequence ISYGRKKRRQRRRP (SEQ ID NO:26) to generate the peptide ISYGRKK$^{Me}$RRQRRRP (SEQ ID NO:20). As another example, in some embodiments, a suitable SET domain-containing polypeptide is capable of methylating a peptide of the sequence SYGRKKRRQR (SEQ ID NO:27) to generate SYGRKK$^{Me}$RRQR (SEQ ID NO:2). Suitable SET domain-containing polypeptides include, e.g., a Set9 polypeptide, a SETDB1 polypeptide, and a SETDB2 polypeptide.

Amino acid sequences of Set9 polypeptides are known in the art. For example, a human Set9 amino acid sequence is found in GenBank Accession No. NP_085151 and depicted in FIG. 12A (SEQ ID NO:31). Other Set9 amino acid sequences are provided in GenBank Accession Nos. Q8WTS6, AAL69901, and AA121056. A suitable Set9 polypeptide includes a polypeptide comprising an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 50 amino acids to about 100 amino acids, from about 100 amino acids to about 150 amino acids, from about 150 amino acids to about 200 amino acids, from about 200 amino acids to about 250 amino acids, from about 250 amino acids to about 300 amino acids, from about 300 amino acids to about 365 amino acids, of the amino acid sequence depicted in FIG. 12A (SEQ ID NO:31); where the Set9 polypeptide is enzymatically active, e.g., is capable of methylating a lysine at a position corresponding to Lys-51 of the Tat polypeptide set forth in FIG. 10. In some embodiments, a suitable Set9 polypeptide comprises the catalytic domain, e.g., a suitable Set9 polypeptide comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 50 amino acids to about 75 amino acids, from about 75 amino acids to about 100 amino acids, or from about 100 amino acids to about 113 amino acids, of amino acids 226-338 of the amino acid sequence depicted in FIG. 12A, where the Set9 polypeptide is enzymatically active, e.g., is capable of methylating a lysine at a position corresponding to Lys-51 of the Tat polypeptide set forth in FIG. 10.

Other SET domain-containing polypeptides that are capable of methylating a lysine at a position corresponding to Lys-51 of the Tat polypeptide set forth in FIG. 10 include, for example, a SETDB1 polypeptide and a SETDB2 polypeptide. vanDuyne et al. (2008) Retrovirol. 5:40. See, e.g., GenBank Accession No. AAH09362 for an amino acid sequence of human SETDB1; and GenBank Accession Nos. AAH47434 and AAH17078 for amino acid sequences of human SETDB2. For example, a suitable Tat Lys-51 methylating polypeptide includes a polypeptide comprising an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 50 amino acids to about 100 amino acids, from about 100 amino acids to about 150 amino acids, from about 150 amino acids to about 200 amino acids, from about 200 amino acids to about 250 amino acids, from about 250 amino acids to about 300 amino acids, from about 300 amino acids to about 350 amino acids, or from about 350 amino acids to about 395 amino acids of the amino acid sequence set forth in SEQ ID NO:79 (human SETDB1). As another example, a suitable Tat Lys-51 methylating polypeptide includes a polypeptide comprising an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 50 amino acids to about 100 amino acids, from about 100 amino acids to 250 amino acids, from about 250 amino acids to about 500 amino acids, or from about 500 amino acids to about 700 amino acids, of the amino acid sequence set forth in SEQ ID NO:80 (human SETDB2). As another example, a suitable Tat Lys-51 methylating polypeptide includes a polypeptide comprising an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 50 amino acids to about 100 amino acids, from about 100 amino acids to about 150 amino acids, from about 150 amino acids to about 200 amino acids, from about 200 amino acids to about 250 amino acids, from about 250 amino acids to about 285 amino acids of the amino acid sequence set forth in SEQ ID NO:81 (human SETDB2).

As noted above, in some embodiments, a subject methylated Tat polypeptide includes, in addition to a methylated lysine at a position corresponding to Lys-51 of SEQ ID NO:1, an acetylated lysine at a position corresponding to Lys-50 of SEQ ID NO:1. An in vitro synthesized Tat polypeptide can be methylated, as described above, and can be acetylated in a cell-free reaction in vitro. For example, a Tat polypeptide can be acetylated in a solution comprising 50 mM HEPES, pH 8, 10% glycerol, 1 mM DTT, 10 mM sodium butyrate, and 20 nmol acetyl-coenzyme A (AcCoA) in the presence of an acetyl transferase for 2 hours at 30° C. See, e.g., Ott et al. (1999) *Curr. Biol.* 9:1489-1492. An acetylated Tat protein can be generated as described in, e.g., Dorr et al. (2002) *EMBO J.* 21:2715-2723; or Peloponese (1999) *J. Biol. Chem.* 274: 11473-11478. Any acetyltransferase can be used, where the acetyltransferase is capable of acetylating a lysine at a position corresponding to Lys-50 of a Tat polypeptide (e.g., a Tat polypeptide comprising an amino acid sequence set forth in SEQ ID NO:1). For example, a suitable acetyltransferase is capable of acetylating a peptide of the sequence ISYGRKK$^{Me}$ RRQRRRP (SEQ ID NO:20) to generate a peptide of the sequence ISYGRK$^{Ac}$K$^{Me}$RRQRRRP (SEQ ID NO:21).

In other embodiments, a Tat polypeptide is methylated post-translationally in a living cell (e.g., a eukaryotic cell) in vitro, e.g., Lys-51 is methylated post-translationally following synthesis of the Tat polypeptide. For example, the cell can include a Set9 polypeptide, e.g., the cell can include an endogenous Set9 polypeptide, or can be genetically modified with a nucleic acid that comprises a nucleotide sequence encoding a Set9 polypeptide. Alternatively, the cell could include a SETDB1 polypeptide or a SETDB2 polypeptide, e.g., the cell can include an endogenous SETDB1 polypeptide or an endogenous SETDB2 polypeptide, or can be genetically modified with a nucleic acid that comprises a nucleotide sequence encoding a SETDB1 polypeptide or a SETDB2 polypeptide.

In some embodiments, a Tat polypeptide is also acetylated post-translationally by a living cell (e.g., a eukaryotic cell) in vitro, e.g., a lysine is post-translationally acetylated following synthesis of the Tat polypeptide. Tat acetylation in a eukaryotic cell is mediated by intracellular acetyltransferases, e.g., histone acetyl transferase (HAT), which catalyzes the transfer of an acetyl group from AcCoA to the epsilon amino group of lysine. Exemplary HATs include GCN5, MYST, p300/CBP, and nuclear receptors.

Methylated Tat polypeptide synthesized by a living eukaryotic cell is recovered using standard methods for protein purification. In some embodiments, the Tat polypeptide that is acetylated by a living eukaryotic cell is a fusion protein comprising a moiety that facilitates purification (e.g., a binding moiety), e.g., GST, 6His, etc., and the methylated Tat polypeptide is purified using a separation medium appropriate to the binding moiety.

Immobilization

In some embodiments, a subject Lys$^{51}$-methylated Tat polypeptide is bound to a solid support or an insoluble support. Insoluble supports include, but are not limited to, beads (including plastic beads, magnetic beads, and the like); plastic plates (e.g., microtiter plates); membranes (e.g., polyvinyl pyrrolidone, nitrocellulose, and the like); test strips; and the like.

Detectable Labels

In some embodiments, a subject Lys$^{51}$ methylated Tat polypeptide is detectably labeled, directly or indirectly. Suitable labels include radioisotopes; enzymes whose products are detectable (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the polypeptide through metal chelating groups such as EDTA; chemiluminescent compounds, e.g., luminol, isoluminol, acridinium salts, and the like; bioluminescent compounds, e.g., luciferin, a fluorescent protein (e.g., a green fluorescent protein, a yellow fluorescent protein, etc.), and the like. In some embodiments, a Lys$^{51}$ methylated Tat polypeptide is detectably labeled during synthesis of the Tat polypeptide, e.g., using a radioactively labeled methyl donor.

Suitable detectable moieties include, but are not limited to, fluorescent, metallic, enzymatic and radioactive markers such as fluorescent proteins, biotin, gold, ferritin, alkaline phosphatase, β-galactosidase, luciferase, horse radish peroxidase, peroxidase, urease, fluorescein, rhodamine, tritium, $^{14}$C, and iodination. The binding agent, e.g., an antibody, can be used as a fusion protein, where the fusion partner is a fluorescent protein. Fluorescent proteins include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; any of a variety of fluorescent and colored proteins from Anthozoan species, as described in, e.g., Matz et al. (1999) *Nature Biotechnol.* 17:969-973; and the like.

Compositions

The present invention provides compositions comprising a subject methylated Tat polypeptide. Compositions comprising a methylated Tat polypeptide can include one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

The present invention provides compositions comprising a subject methylated Tat polypeptide, which in some embodiments are immunogenic compositions. Compositions comprising a subject methylated Tat polypeptide may include a buffer, which is selected according to the desired use of the methylated Tat polypeptide, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19$^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

Pharmaceutical compositions can be prepared in various forms, such as granules, tablets, pills, suppositories, capsules, suspensions, sprays, suppositories, transdermal applications (e.g., patches, etc.), salves, lotions and the like. Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

In some embodiments, a subject composition is an immunogenic composition. When used as an immunogenic composition, a subject methylated Tat polypeptide can be formulated in a variety of ways. In general, a subject immunogenic composition is formulated according to methods well known in the art using suitable pharmaceutical carrier(s) and/or vehicle(s). A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, an immunogenic composition of the invention may be formulated to contain other components, including, e.g., adjuvants, stabilizers, pH adjusters, preservatives and the like. Such components are well known to those of skill in the vaccine art. Adjuvants include, but are not limited to, aluminum salt adjuvants (Nicklas (1992) *Res. Immunol.* 143: 489-493); saponin adjuvants; Ribi's adjuvants (Ribi ImmunoChem Research Inc., Hamilton, Mont.); Montanide ISA adjuvants (Seppic, Paris, France); Hunter's TiterMax adjuvants (CytRx Corp., Norcross, Ga.); Gerbu adjuvants (Gerbu Biotechnik GmbH, Gaiberg, Germany); ISCOM® adjuvants (CSL Ltd.); and nitrocellulose (Nilsson and Larsson (1992) *Res. Immunol.* 143:553-557). In addition, other components that may modulate an immune response may be included in the formulation, including, but not limited to, cytokines, such as interleukins; colony-stimulating factors (e.g., GM-CSF, G-CSF, and the like); and tumor necrosis factor.

Therapeutic agents that can be formulated together with one or more additional therapeutic agents. Suitable additional therapeutic agents include, but are not limited to, anti-inflammatory, anti-viral, anti-fungal, anti-mycobacterial, antibiotic, amoebicidal, trichomonocidal, analgesic, anti-neoplastic, anti-hypertensives, anti-microbial and/or steroid drugs, to treat antiviral infections. In some embodiments, a combination of one or more acetylated Tat polypeptides is formulated with one or more of the following; beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), a fusion inhibitor (e.g., a T20 peptide, a T-1249 peptide; Trimeris); an anti-CD4 antibody (e.g., an anti-CD4 antibody from Tanox, Inc.); an anti-CCR5 antibody (e.g., Pro 140); a CXCR4 blocker (e.g., AMD 3100); an HIV entry inhibitor (e.g., Pro-542; Progenics); a CCR5 blocker (e.g., SCH-C, SCH-D; Schering Plough); anti-receptor antibodies (e.g., for rhinoviruses), nevirapine (Viramune®), emiravine (Coactinon®), cidofovir (Vistide™), trisodium phosphonoformate (Foscamet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clarithromycin, erythropoietin, colony stimulating factors (G-CSF and GM-CSF), non-nucleoside reverse transcriptase inhibitors, nucleoside reverse transcriptase inhibitors, HIV protease inhibitors, adriamycin, fluorouracil, methotrexate, asparaginase and combinations thereof.

In some embodiments, a subject composition comprising an methylated Tat polypeptide comprises two or more methylated Tat polypeptides, e.g., the composition is heterogeneous with respect to methylated Tat polypeptides. For example, a subject composition comprises two or more of the polypeptides having amino acid sequences set forth in SEQ ID NO:2-25. Thus, in some embodiments, a subject composition comprises a first methylated Tat polypeptide, and at least a second methylated Tat polypeptide, wherein the first and the second methylated Tat polypeptides differ in amino acid sequence by at least one amino acid.

Antibodies

The present invention further provides antibody reagents specific for a Lys-51 methylated Tat polypeptide. A subject antibody (also referred to as an "antibody reagent") is useful for detecting Lys-51 methylated Tat protein in a sample, e.g., a biological sample, a sample generated in a screening method, etc. A subject antibody is useful in methods of detecting, in a biological sample obtained from an individual, the presence and/or level of a $Lys^{51}$ methylated Tat polypeptide.

Antibodies include naturally-occurring antibodies, artificial antibodies, intrabodies, antibody fragments, polyclonal antibodies, monoclonal antibodies, single-chain antibodies, and the like, that specifically bind a Lys-51 methylated Tat polypeptide.

A subject antibody specifically binds a Lys-51 methylated Tat polypeptide, where a "Lys-51 methylated Tat polypeptide" is a Tat polypeptide comprising a methylated lysine at a position corresponding to Lys-51 of the amino acid sequence set forth in SEQ ID NO:1. For example, a subject antibody specifically binds a Lys-51 methylated Tat polypeptide comprising the amino acid sequence SYGRKK$^{Me}$RRQR (SEQ ID NO:2) or a variant thereof that includes the methylated lysine.

In some embodiments, a subject antibody specifically binds a monomethylated Lys-51 methylated Tat polypeptide. In other embodiments, a subject antibody specifically binds a dimethylated Lys-51 methylated Tat polypeptide. In other embodiments, a subject antibody specifically binds a trimethylated Lys-51 methylated Tat polypeptide.

In some embodiments, a subject antibody specifically binds a Lys-51 methylated Tat polypeptide that further includes an acetylated lysine at a position corresponding to Lys-50 of SEQ ID NO:1. Such a Tat polypeptide is referred to as a "Lys-51 methylated, Lys-50 acetylated Tat polypeptide." In some embodiments, a subject antibody specifically binds a Lys-51 methylated, Lys-50 acetylated Tat polypeptide. For example, in some embodiments, a subject antibody specifically binds a Tat polypeptide comprising the amino acid sequence SYGRK$^{Ac}$K$^{Me}$RRQR (SEQ ID NO:3), or a variant thereof that comprises K$^{Ac}$K$^{Me}$.

In some embodiments, a subject antibody discriminates between a Tat polypeptide comprising the amino acid sequence SYGRKK$^{Me}$RRQR (SEQ ID NO:2) and a Tat polypeptide comprising the amino acid sequence SYGRK$^{Ac}$K$^{Me}$RRQR (SEQ ID NO:3).

In some embodiments, a subject antibody binds specifically to native Lys-51 methylated Tat protein, e.g., to native methylated Tat protein present in vivo in an individual infected with an immunodeficiency virus such as HIV-1.

In many embodiments, a subject antibody is isolated, e.g., is in an environment other than its naturally-occurring environment. In some embodiments, a subject antibody is synthetic. Suitable antibodies are obtained by immunizing a host animal with peptides comprising all or a portion of the subject protein. Suitable host animals include mouse, rat, sheep, goat, hamster, rabbit, etc. The host animal is any mammal that is capable of mounting an immune response to a Lys-51 methylated Tat protein, where representative host animals include, but are not limited to, e.g., rabbits, goats, mice, etc.

The immunogen may comprise the complete protein, or fragments and derivatives thereof. Suitable immunogens comprise all or a part of the protein. Immunogens are produced in a variety of ways known in the art, e.g., expression of cloned genes using conventional recombinant methods, followed by in vitro methylation; methylation of a Tat protein in a cell; preparation of fragments of a methylated Tat protein using well-known methods, etc.

In some embodiments, a subject antibody is bound to a solid support or an insoluble support. Insoluble supports include, but are not limited to, beads (including plastic beads, magnetic beads, and the like); plastic plates (e.g., microtiter plates); membranes (e.g., polyvinyl pyrrolidone, nitrocellulose, and the like); test strips; and the like.

For preparation of polyclonal antibodies, the first step is immunization of the host animal with the target protein (Lys-51 methylated Tat polypeptide), where the target protein can be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil and water emulsions, e.g. Freund's adjuvant, Freund's complete adjuvant, and the like. The target protein may also be conjugated to a carrier, e.g., keyhole limpet hemocyanin (KLH), bovine serum albumin (BSA), a synthetic carrier protein, and the like. A variety of hosts may be immunized to produce the polyclonal antibodies. Such hosts include rabbits, guinea pigs, rodents, e.g. mice, rats, sheep, goats, and the like. The target protein is administered to the host, e.g., intradermally, with an initial dosage followed by one or more, usually at least two, additional booster dosages. Following immunization, the blood from the host will be collected, followed by separation of the serum from the blood cells. The immunoglobulin present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) *J. Biol. Chem.* 269:26267-73, and elsewhere. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also provided are "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516,637; 5,223,409; 5,658,727; 5,667,988; 5,498,538; 5,403,484; 5,571,698; and 5,625,033.

Also of interest are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *Proc. Natl. Acad. Sci. USA.* 84:3439 and (1987) *J. Immunol.* 139: 3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Exemplary isotypes are IgG1, IgG3 and IgG4. Either of the human light chain constant regions, kappa or lambda, may be used. The chimeric, humanized antibody is then expressed by conventional methods. Other methods for preparing chimeric antibodies are described in, e.g., U.S. Pat. No. 5,565,332.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L chain J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, BACs, EBV-derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral long terminal repeats (LTRs) and other promoters, e.g. SV-40 early promoter, (Okayama et al. (1983) Mol. Cell. Bio. 3:280), Rous sarcoma virus LTR (Gorman et al. (1982) Proc. Natl. Acad. Sci. USA 79:6777), and moloney murine leukemia virus LTR (Grosschedl et al. (1985) Cell 41:885); native Ig promoters, etc.

Intrabodies that specifically bind Lys-51 methylated Tat are expressed in a cell in an individual. See, e.g., Marasco et al. (1999) J. Immunol. Methods 231:223-238. Intracellularly expressed antibodies, or intrabodies, are single-chain antibody molecules designed to specifically bind and inactivate target molecules inside cells. See, e.g., Chen et al., Hum. Gen. Ther. (1994) 5:595-601; Hassanzadeh et al., Febs Lett. (1998) 16(1, 2):75-80 and 81-86; Marasco (1997) Gene Ther. 4:11-15; and "Intrabodies: Basic Research and Clinical Gene Therapy Applications" W. A. Marasco, e.g., (1998) Springer-Verlag, NY. Inducible expression vectors can be constructed that encode intrabodies that bind specifically to Lys-51 methylated Tat protein. These vectors are introduced into an individual, and production of the intrabody induced by administration to the individual of the inducer. Alternatively, the expression vector encoding the intrabody provides for constitutive production of the intrabody.

A subject antibody can be labeled, directly or indirectly. Suitable labels include radioisotopes; enzymes whose products are detectable (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, a fluorescent protein (e.g., a green fluorescent protein, a yellow fluorescent protein, etc.), and the like.

Suitable detectable moieties include, but are not limited to, fluorescent, metallic, enzymatic and radioactive markers such as fluorescent proteins, biotin, gold, ferritin, alkaline phosphatase, β-galactosidase, luciferase, horse radish peroxidase, peroxidase, urease, fluorescein, rhodamine, tritium, $^{14}$C, and iodination. The binding agent, e.g., an antibody, can be used as a fusion protein, where the fusion partner is a fluorescent protein. Fluorescent proteins include, but are not limited to, a green fluorescent protein from Aequoria victoria or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; any of a variety of fluorescent and colored proteins from Anthozoan species, as described in, e.g., Matz et al. (1999) Nature Biotechnol. 17:969-973; and the like.

Compositions

The present invention provides compositions comprising a subject antibody. Compositions comprising a subject antibody can include one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

In some instances, a composition comprising a subject antibody can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19$^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

Screening Methods

The present invention further provides methods of identifying agents that inhibit methylation of a Tat polypeptide at Lys-51. The methods generally involve contacting a Tat polypeptide, a SET domain-containing polypeptide (e.g., a Set9 polypeptide, a SETDB1 polypeptide, a SETDB2 polypeptide), and a methyl donor, with a test agent, forming a test sample; and determining the effect, if any, of the test agent on methylation of the Tat polypeptide by the SET domain-containing polypeptide. A suitable methyl donor is S-adenosyl methionine (SAM). In some embodiments, the methyl donor is detectably labeled, such that the methylated Tat is detectably labeled, following reaction with a SET domain-containing polypeptide in the absence of a test agent.

A test agent that inhibits methylation of a Tat polypeptide by a SET domain-containing polypeptide (e.g., a Set9 polypeptide, a SETDB1 polypeptide, a SETDB2 polypeptide) is a candidate agent for treating an immunodeficiency virus infection. A test agent of interest inhibits methylation of a Tat polypeptide by a SET domain-containing polypeptide by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or more, compared to the degree or level of methylation of the Tat polypeptide in the absence of the test agent.

For example, in some embodiments, a test agent of interest reduces the proportion of the total Tat polypeptides present in the test sample that are methylated by the SET domain-containing polypeptide by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more, compared to the proportion of the total Tat polypeptides present in the test sample that are methylated by the SET domain-containing polypeptide in the absence of the test agent.

In other words, in some embodiments, a test agent of interest reduces the percentage of methylated Tat polypeptides (e.g., Lys-51 methylated Tat polypeptides; or Tat polypeptides methylated at a position corresponding to Lys-51 of the amino acid sequence set forth in SEQ ID NO:1) in the test sample by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more, compared to the percentage of methylated Tat polypeptides in the test sample in the absence of the test agent.

In some embodiments, a test agent of interest is one that inhibits Lys-51 methylation of a Tat polypeptide by a SET domain-containing polypeptide with a 50% inhibitory concentration ($IC_{50}$) of from about 100 µM to about 50 µM, from about 50 µM to about 25 µM, from about 25 µM to about 10 µM, from about 10 µM to about 5 µM, from about 5 µM to about 1 µM, from about 1 µM to about 500 nM, from about 500 nM to about 400 nM, from about 400 nM to about 300 nM, from about 300 nM to about 250 nM, from about 250 nM to about 200 nM, from about 200 nM to about 150 nM, from about 150 nM to about 100 nM, from about 100 nM to about 50 nM, from about 50 nM to about 30 nM, from about 30 nM to about 25 nM, from about 25 nM to about 20 nM, from about 20 nM to about 15 nM, from about 15 nM to about 10 nM, from about 10 nM to about 5 nM, or less than about 5 nM.

By "test agent," "candidate agent," and grammatical equivalents thereof, which terms are used interchangeably herein, is meant any molecule (e.g. proteins (which herein includes proteins, polypeptides, and peptides), small (i.e., 5 Da-1000 Da, 100 Da-750 Da, 200 Da-500 Da, or less than 500 Da in size), or organic or inorganic molecules, polysaccharides, polynucleotides, etc.) which are to be tested for activity in inhibiting methylation of a Tat polypeptide by a SET domain-containing polypeptide.

A variety of different test agents may be screened using a subject method. Candidate agents encompass numerous chemical classes, e.g., small organic compounds having a molecular weight of more than 50 daltons and less than about 10,000 daltons, less than about 5,000 daltons, or less than about 2,500 daltons. Test agents can comprise functional groups necessary for structural interaction with proteins, e.g., hydrogen bonding, and can include at least an amine, carbonyl, hydroxyl or carboxyl group, or at least two of the functional chemical groups. The test agents can comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds and chemical analogs thereof, or to new agents with unknown properties such as those created through rational drug design.

In one embodiment, test agents are synthetic compounds. A number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

In another embodiment, the test agents are provided as libraries of natural compounds in the form of bacterial, fungal, plant and animal extracts that are available or readily produced. Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In one embodiment, the test agents are organic moieties. In this embodiment, as is generally described in WO 94/24314, test agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

As used herein, the term "determining" refers to both quantitative and qualitative determinations and as such, the term "determining" is used interchangeably herein with "assaying," "measuring," and the like.

In some embodiments, in addition to determining the effect of a test agent methylation of a Tat polypeptide by a SET domain-containing polypeptide, test agents are assessed for any cytotoxic activity it may exhibit toward a living eukaryotic cell, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

The SET domain-containing polypeptide that is used need only be capable of methylating lysine at a position corresponding to Lys-51 of a Tat polypeptide, e.g., a Tat polypeptide comprising the amino acid sequence set forth in SEQ ID NO:1. Suitable SET domain-containing polypeptides include a Set9 polypeptide, a SETDB1 polypeptide, and a SETDB2 polypeptide.

For example, in some embodiments, a suitable SETDB1 polypeptide is capable of methylating a peptide of the sequence ISYGRKKRRQRRRP (SEQ ID NO:26) to generate the peptide ISYGRKK$^{Me}$RRQRRRP (SEQ ID NO:20). As another example, in some embodiments, a suitable SETDB1 polypeptide is capable of methylating a peptide of the sequence SYGRKKRRQR (SEQ ID NO:27) to generate SYGRKK$^{Me}$RRQR (SEQ ID NO:2).

In some embodiments, the SET domain-containing polypeptide is a Set9 polypeptide. Amino acid sequences of Set9 polypeptides are known in the art. For example, a human Set9 amino acid sequence is found in GenBank Accession No. NP_085151 and depicted in FIG. 12A. Other Set9 amino acid sequences are provided in GenBank Accession Nos. Q8WTS6, AAL69901, and AA121056. A suitable Set9 polypeptide includes a polypeptide comprising an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 50 amino acids to about 100 amino acids, from about 100 amino acids to about 150 amino acids, from about 150 amino acids to about 200 amino acids, from about 200 amino acids to about 250 amino acids, from about 250 amino acids to about 300 amino acids, from about 300 amino acids to about 365 amino acids, of the amino acid sequence depicted in FIG. 12A; where the Set9 polypeptide is enzymatically active, e.g., is capable of methylating a lysine at a position corresponding to Lys-51 of the Tat polypeptide set forth in FIG. 10. In some embodiments, a suitable Set9 polypeptide comprises the catalytic domain, e.g., a suitable Set9 polypeptide comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 50 amino acids to about 75 amino acids, from about 75 amino acids to about 100 amino acids, or from about 100 amino acids to about 113 amino acids, of amino acids 226-338 of the amino acid sequence depicted in FIG. 12A, where the Set9 polypeptide is enzymatically active, e.g., is capable of methylating a lysine at a position corresponding to Lys-51 of the Tat polypeptide set forth in FIG. 10.

In some embodiments, the SET domain-containing polypeptide is a SETDB1 polypeptide. In other embodiments, the SET domain-containing polypeptide is a SETDB2 polypeptide. For example, a suitable Tat Lys-51 methylating polypeptide includes a polypeptide comprising an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 50 amino acids to about 100 amino acids, from about 100 amino acids to about 150 amino acids, from about 150 amino acids to about 200 amino acids, from about 200 amino acids to about 250 amino acids, from about 250 amino acids to about 300 amino acids, from about 300 amino acids to about 350 amino acids, or from about 350 amino acids to about 395 amino acids of the amino acid sequence set forth in SEQ ID NO:79 (human SETDB1). As another example, a suitable Tat Lys-51 methylating polypeptide includes a polypeptide comprising an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 50 amino acids to about 100 amino acids, from about 100 amino acids to 250 amino acids, from about 250 amino acids to about 500 amino acids, or from about 500 amino acids to about 700 amino acids, of the amino acid sequence set forth in SEQ ID NO:80 (human SETDB2). As another example, a suitable Tat Lys-51 methylating polypeptide includes a polypeptide comprising an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 50 amino acids to about 100 amino acids, from about 100 amino acids to about 150 amino acids, from about 150 amino acids to about 200 amino acids, from about 200 amino acids to about 250 amino acids, from about 250 amino acids to about 285 amino acids of the amino acid sequence set forth in SEQ ID NO:81 (human SETDB2)

Suitable Tat polypeptides have a length of from about 10 amino acids to about 50 amino acids (e.g., a length of 10 amino acids (aa) to 15 aa (e.g., 10 aa, 11 aa, 12 aa, 13 aa, 14 aa, or 15 aa), 15 aa to 20 aa (e.g., 15 aa, 16 aa, 17 aa, 18 aa, 19 aa, or 20 aa), 20 aa to 25 aa (e.g., 20 aa, 21 aa, 22 aa, 23 aa, 24 aa, or 25 aa), 25 aa to 30 aa, 30 aa to 35 aa, 35 aa to 40 aa, 40 aa to 45 aa, or 45 aa to 50 aa), from about 50 amino acids to about 60 amino acids, from about 60 amino acids to about 70 amino acids, from about 70 amino acids to about 80 amino acids, from about 80 amino acids to about 90 amino acids, from about 90 amino acids to about 100 amino acids, or longer than 100 amino acids, where the Tat polypeptide comprises a lysine corresponding to Lys-51 of SEQ ID NO:1, e.g., where the Tat polypeptide comprises the amino acid sequence SYGRKKRRQR (SEQ ID NO:27), or a variant thereof.

In some embodiments, a suitable Tat polypeptide comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity with a contiguous stretch of from about 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to about 80 aa, from about 80 aa to about 90 aa, or from about 90 aa to about 100 aa of the amino acid sequence set forth in SEQ ID NO:1; and includes a lysine corresponding to Lys-51 of the amino acid sequence set forth in SEQ ID NO:1. A suitable Tat polypeptide generally includes a lysine at a position corresponding to Lys-50 of the amino acid sequence set forth in SEQ ID NO:1, where the Lys-50 is not acetylated.

In some embodiments, a suitable Tat polypeptide comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity with a contiguous stretch of from about 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to about 80 aa, from about 80 aa to about 90 aa, or from about 90 aa to about 100 aa of the amino acid sequence set forth in SEQ ID NO:1; and includes the amino acid sequence SYGRKKRRQR (SEQ ID NO:27).

In some embodiments, a suitable Tat polypeptide comprises the amino acid sequence SYGRKKRRQR (SEQ ID NO:27) and has a length of from 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to about 80 aa, from about 80 aa to about 90 aa, or from about 90 aa to about 100 aa, or longer than 100 aa.

In some embodiments, a suitable Tat polypeptide comprises the amino acid sequence ISYGRKKRRQRR (SEQ ID NO:28) and has a length of from 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to about 80 aa, from about 80 aa to about 90 aa, or from about 90 aa to about 100 aa, or longer than 100 aa.

In some embodiments, a suitable Tat polypeptide comprises the amino acid sequence ISYGRKKRRQRRRP (SEQ ID NO:26) and has a length of from 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to about 80 aa, from about 80 aa to about 90 aa, or from about 90 aa to about 100 aa, or longer than 100 aa.

In some embodiments, a Tat polypeptide is a fusion protein, e.g., a polypeptide comprising a Tat polypeptide and a heterologous (non-Tat) polypeptide (e.g., a fusion partner), where suitable heterologous polypeptides (fusion partners) include, e.g., an epitope tag; enzymes that act on a substrate to yield a detectable product (e.g., alkaline phosphatase, luciferase, horse radish peroxidase, β-galactosidase, etc.); fluorescent proteins (e.g., a green fluorescent protein, a yellow fluorescent protein, etc.); and the like. The Tat polypeptide can also be detectably labeled, e.g., with a radiolabel. In some embodiments, the Tat polypeptide is biotinylated.

In addition to a Tat polypeptide, a SET domain-containing polypeptide and a test agent, a variety of other reagents may be included in the screening assay. These include reagents like salts, neutral proteins, e.g. albumin, detergents, etc., including agents that are used to facilitate optimal enzyme activity and/or reduce non-specific or background activity. Reagents that improve the efficiency of the assay, such as protease inhibitors, anti-microbial agents, etc. may be used. The components of the assay mixture are added in any order that provides for the requisite activity. Incubations are performed at any suitable temperature, typically between 4° C. and 40° C. Incubation periods are selected for optimum activity, but may also be optimized to facilitate rapid high-throughput screening. In some embodiments, between 0.1 hour and 1 hour, between 1 hour and 2 hours, or between 2 hours and 4 hours, will be sufficient.

Assays of the invention include controls, where suitable controls include a sample (e.g., a sample comprising the Tat polypeptide and the SET domain-containing polypeptide in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

The effect, if any, of the test agent on methylation of the Tat polypeptide by the SET domain-containing polypeptide can be readily determined by assessing the degree of methylation of the Tat polypeptide. Methylation of the Tat polypeptide can be determined using, e.g., an antibody specific for Lys-51 methylated Tat polypeptide. Methylation of the Tat polypeptide can also be determined using MALDI-TOF, as described in the Examples.

In some embodiments, the effect of the test agent on methylation of the Tat polypeptide is determined using an antibody specific for Lys-51 methylated Tat polypeptide. A subject antibody specific for Lys-51 methylated Tat polypeptide is suitable for use. The determination step can be carried out using an immunoprecipitation method; an enzyme-linked immunosorbent assay (ELISA); an immunoblot assay; a radioimmunoassay (RIA); and the like, where an antibody specific for Lys-51 methylated Tat polypeptide is used. In some embodiments, an antibody that specifically recognizes a polypeptide comprising the amino acid sequence SYGRKKRRQR (SEQ ID NO:27), where the lysine corresponding to Lys-51 of the amino acid sequence set forth in SEQ ID NO:1 is not methylated, can be used to assess the amount of Tat polypeptide that is not Lys-51 methylated, e.g., the amount of Tat polypeptide that is not methylated at a lysine corresponding to Lys-51 of the amino acid sequence set forth in SEQ ID NO:1.

In other embodiments, the methyl donor is radioactively labeled, and the determining step comprises detecting the radiolabel in the methylated Tat peptide following reaction with the SET domain-containing polypeptide.

In some embodiments, a subject screening method is a cell-free in vitro screening method. In other embodiments, a subject screening method is a cell-based in vitro screening method.

In carrying out a cell-free in vitro screening method, a Tat polypeptide and a SET domain-containing polypeptide can be present in the test sample in substantially pure form, in cell extracts, or other non-purified form.

Cell-Based Assays

In some embodiments, a subject screening method is a cell-based in vitro screening method. A cell expressing a SET domain-containing polypeptide and Tat polypeptides is contacted with a test agent; and the effect, if any, of the test agent on SET domain-containing polypeptide-mediated methylation of the Tat polypeptide (e.g., methylation at a lysine corresponding to Lys-51 of the amino acid sequence set forth in SEQ ID NO:1) is determined. The effect of the agent on SET domain-containing polypeptide-mediated methylation of the Tat polypeptide can be determined as described above. For example, for the determining step, a cell extract or cell lysate comprising the Tat polypeptide can be analyzed, or the Tat polypeptide can be isolated, e.g., in substantially pure form, from a cell lysate, then analyzed for methylation.

Cell-based in vitro screening methods can be carried out using any of a variety of cells, e.g., primary cells, immortalized cells, and the like. In some embodiments, the cells are eukaryotic cells. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), Jurkat cells (e.g., ATCC TIB-152), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. Derivatives of such cells are also suitable for use. Also suitable for use are human T cell lines with latent immunodeficiency virus, e.g., a cell line as described in U.S. Pat. No. 7,232,685.

In some embodiments, the cell produces an endogenous SET domain-containing polypeptide. In other embodiments, the cell is genetically modified with a nucleic acid comprising a nucleotide sequence that encodes an enzymatically active SET domain-containing polypeptide (e.g., a Set9 polypeptide, a SETDB1 polypeptide, a SETDB2 polypeptide).

Nucleotide sequences encoding Set9 polypeptides are known in the art; see, e.g., GenBank Accession No. BC121055; and FIG. 12B (SEQ ID NO:32). A suitable Set9 nucleic acid comprises a nucleotide sequence having at least about 50%, at least about 60%, at least about 70%, at least about 75%, at least about 80%, at least about 85%, at least about 90%, at least about 95%, at least about 98%, at least about 99%, or 100% nucleotide sequence identity to the nucleotide sequence set forth in FIG. 12B (SEQ ID NO:32), FIG. 14 (SEQ ID NO:67), or 15A and 15B (SEQ ID NO:68).

In some embodiments, a suitable Set9 nucleic acid comprises a nucleotide sequence having at least about 50%, at least about 60%, at least about 70%, at least about 75%, at least about 80%, at least about 85%, at least about 90%, at least about 95%, at least about 98%, at least about 99%, or 100% nucleotide sequence identity to a nucleotide sequence that encodes the catalytic domain of a Set9 polypeptide, e.g., amino acids 226-338 of the amino acid sequence depicted in FIG. 12A. The nucleotide sequence encoding the Set9 polypeptide is operably linked to a transcriptional control element (e.g., a promoter), where suitable promoters include inducible promoters and constitutive promoters. In some embodiments, the Set9 nucleic acid is provided in an expression vector, as described in more detail below.

A suitable SETDB1 nucleic acid comprises a nucleotide sequence having at least about 50%, at least about 60%, at least about 70%, at least about 75%, at least about 80%, at least about 85%, at least about 90%, at least about 95%, at least about 98%, at least about 99%, or 100% nucleotide sequence identity to the nucleotide sequence set forth in SEQ ID NO:82. A suitable SETDB2 nucleic acid comprises a nucleotide sequence having at least about 50%, at least about 60%, at least about 70%, at least about 75%, at least about 80%, at least about 85%, at least about 90%, at least about 95%, at least about 98%, at least about 99%, or 100% nucleotide sequence identity to the nucleotide sequence set forth in SEQ ID NO:83.

The cell can also be genetically modified with a Tat nucleic acid, e.g., a nucleic acid comprising a nucleotide sequence encoding a Tat polypeptide that comprises at least a lysine corresponding to Lys-51 of the amino acid sequence set forth in SEQ ID NO:1. A suitable Tat nucleic acid comprises a nucleotide sequence having at least about 50%, at least about 60%, at least about 70%, at least about 80%, at least about 85%, at least about 90%, at least about 95%, at least about 98%, at least about 99% or 100% nucleotide sequence identity with a contiguous stretch of from about 30 nucleotides to about 45 nucleotides, from about 45 nucleotides to about 60 nucleotides, from about 60 nucleotides to about 75 nucleotides, from about 75 nucleotides to about 90 nucleotides, from about 90 nucleotides to about 105 nucleotides, from about 105 nucleotides to about 120 nucleotides, from about 120 nucleotides to about 135 nucleotides, from about 135 nucleotides to about 150 nucleotides, from about 150 nucleotides to about 165 nucleotides, from about 165 nucleotides to about 180 nucleotides, from about 180 nucleotides to about 195 nucleotides, from about 195 nucleotides to about 210 nucleotides, from about 210 nucleotides to about 225 nucleotides, from about 225 nucleotides to about 240 nucleotides, from about 240 nucleotides to about 255 nucleotides, from about 255 nucleotides to about 270 nucleotides, from about 270 nucleotides to about 285 nucleotides, or from about 285 nucleotides to about 306 nucleotides of the nucleotide sequence depicted in FIG. 13, where the nucleotide sequence comprises a sequence encoding a lysine corresponding to Lys-51 of the amino acid sequence set forth in SEQ ID NO:1, e.g., where the nucleotide sequence comprises a sequence encoding at least SYGRKKRRQR (SEQ ID NO:27), or a variant thereof.

In some embodiments, a Tat nucleic acid comprises a nucleotide sequence encoding a Tat polypeptide comprising at least SYGRKKRRQR (SEQ ID NO:27), or a variant thereof. In some embodiments, a suitable Tat nucleic acid comprises the nucleotide sequence 5'-TCCTATGGCAG-GAAGAAGCGGAGACAGCGA-3' (SEQ ID NO:30). In some embodiments, the nucleotide sequence encoding the Tat polypeptide is operably linked to a transcriptional control element; and is in some embodiments contained within an expression vector, as described below.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, HIV-based lentivirus vectors, and the like), P1-based artificial chromosomes, yeast plasmids, yeast artificial chromosomes, and any other vectors specific for specific hosts of interest (such as E. coli, mammalian cells, or yeast). Suitable vectors include chromosomal, nonchromosomal and synthetic DNA sequences.

Numerous suitable expression vectors are known to those of skill in the art, and many are commercially available. For example, suitable expression vectors for use in eukaryotic host cells include, but are not limited to, pXT1, pSG5 (Stratagene), pSVK3, pBPV, pMSG, and pSVLSV40 (Pharmacia). However, any other vector may be used so long as it is compatible with the host cell.

Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

Generally, an expression vector will include origins of replication. In addition, the expression vectors include one or more selectable marker genes to provide a phenotypic trait for selection of transformed (genetically modified) host cells such as dihydrofolate reductase or neomycin resistance for eukaryotic cell culture.

Detection Methods

The present invention provides detection methods, e.g., diagnostic methods. In some embodiments, a subject detection method provides for detecting, in a biological sample obtained from an individual, the presence and/or level of an antibody specific for $Lys^{51}$ methylated Tat polypeptide. In other embodiments, a subject detection method provides for detecting, in a biological sample obtained from an individual, the presence and/or level of a $Lys^{51}$ methylated Tat polypeptide.

Detecting Antibody Specific for $Lys^{51}$-Methylated Tat Polypeptide

The present invention provides methods of detecting, in a biological sample obtained from an individual, the presence and/or level of an antibody specific for $Lys^{51}$ methylated Tat polypeptide. The methods are useful for diagnostic purposes, e.g., to determine whether an individual is infected with an immunodeficiency virus, to monitor the progress of an immunodeficiency virus infection, or to assess the efficacy of a treatment for an immunodeficiency virus infection.

The methods generally involve contacting a biological sample obtained from an individual being tested with a subject $Lys^{51}$-methylated Tat polypeptide; and detecting binding between molecules (e.g., antibodies) in the biological sample and the Tat polypeptide, e.g., detecting a complex formed between an antibody in the biological sample and the Tat polypeptide. Detection can be carried out using any of a variety of methods. For example, the $Lys^{51}$-methylated Tat polypeptide can be detectably labeled, and an antibody-Tat polypeptide complex can be detected by detecting the label in the antibody-Tat polypeptide complex. As another example, an immunological assay can be used, whereby an antibody specific for an antibody isotype, e.g., a detectably labeled antibody specific for a human antibody isotype, is used to detect an antibody-Tat polypeptide complex. As another example, an antibody specific for a Tat polypeptide can be used, e.g., a detectably labeled antibody specific for a Tat polypeptide, to detect antibody-Tat polypeptide complex. Any of a variety of assay formats can be used, e.g., where the Lys methylated Tat polypeptide is immobilized on a solid support (e.g., a membrane, e.g., in the form of a test strip, etc., as described above); where an antibody specific for a Tat polypeptide is immobilized on a solid support (e.g., a membrane, e.g., in the form of a test strip, etc.); and the like.

Detecting $Lys^{51}$-Methylated Tat Polypeptide

The present invention provides methods of detecting, in a biological sample obtained from an individual, the presence and/or level of a $Lys^{51}$ methylated Tat polypeptide. The methods are useful for diagnostic purposes, e.g., to determine whether an individual is infected with an immunodeficiency virus, to monitor the progress of an immunodeficiency virus infection, or to assess the efficacy of a treatment for an immunodeficiency virus infection.

The methods generally involve contacting a biological sample obtained from an individual being tested with a subject antibody specific for a $Lys^{51}$-methylated Tat polypeptide; and detecting binding between the antibody and a $Lys^{51}$-methylated Tat polypeptide in the biological sample, e.g., detecting a complex formed between an antibody in the biological sample and the $Lys^{51}$-methylated Tat polypeptide. Detection can be carried out using any of a variety of methods. In some embodiments, a subject antibody is immobilized on a solid support (e.g., a membrane, such as a test strip; a bead; and the like, as described above); the biological sample is contacted with the immobilized antibody; and formation of a complex between a $Lys^{51}$-methylated Tat polypeptide and the immobilized antibody is detected, e.g., using a detectably labeled antibody specific for Tat.

Treatment Methods

The present invention provides methods of treating an immunodeficiency virus infection in an individual, the methods comprising administering to an individual in need thereof an effective amount of an agent that inhibits Set9-mediated methylation of an immunodeficiency virus Tat polypeptide in a cell in the individual.

In some embodiments, the Set9 inhibitor specifically inhibits Set9-mediated methylation of Lys-51 of a Tat polypeptide, e.g., the Set9 inhibitor does not substantially inhibit Set9-mediated histone methylation.

In some embodiments, the Set9 inhibitor (also referred to herein as an "active agent") is a small molecule. In other embodiments, the active agent is a Tat peptide having a length of from about 5 amino acids to about 50 amino acids.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Methylation of Lysine 51 Activates HIV-1 Tat Transcriptional Activity

Materials and Methods
Cells and Plasmids

HeLa and HEK293 cells (obtained from the American Type Culture Collection), and the Jurkat clones A72 and A2 (2) (Jordan et al. (2003) *EMBO J.* 22:1868-77) were maintained under standard cell culture conditions. The HIV LTR luciferase construct (3) (Van Lint et al. (1997) *J Virol* 71:6113-27), pGST-p300 HAT (4) (Ott et al. (1999) *Curr Biol* 9:1489-92), Set9 expression vector and Set9H297A (5) (Nishioka et al. (2002) *Genes Dev* 16:479-89) were previously described.

The Tat cDNA from CMV-Tat/FLAG expression vector (4) (Ott et al. (1999) supra) was subcloned into the pEF-BOS plasmid, which drives expression under the EF1α promoter (6) (Mizushima and Nagata (1990) *Nucleic Acids Res* 18:5322) to generate a EF1α-Tat/FLAG fusion by standard polymerase chain reaction (PCR)-based strategies. The mutants TatK51A and TatK51R were generated by site-directed mutagenesis. The TatK51A mutant was generated with the following primers: Forward, 5'-CCTATGGCAGGAAG-GCGCGGAGACAGCG-3' (SEQ ID NO:69) and reverse, 5'-CGCTGTCTCCGCGCCTTCCTGCCATAGG-3' (SEQ ID NO:70). The TatK51R mutant was generated with the following primers: Forward, 5'-CCTATGGCAGGAAGAG-GCGGAGACAGCG-3' (SEQ ID NO:71) and reverse, 5'-CGCTGTCTCCGCCTCTTCCTGCCATAGG-3' (SEQ ID NO:72).

Synthetic Tat peptides and recombinant proteins

Synthesis of 72-amino acid Tat proteins was as described (1, 7). Dorr et al. (2002) *EMBO J.* 21:2715-23; and Kaehlcke et al. (2003) *Mol Cell* 12:167-76. The Tat peptides spanning the Tat sequence and the modified versions of the ARM peptides (K50A, K51A, K50, K51AA, K50Ac, K51me) were synthesized by Hans-Richard Rackwitz (Peptide Specialty Laboratories GmbH, Heidelberg, Germany).

Recombinant GST-p300 HAT was expressed in the BL21 strain of *Escherichia coli* and purified on glutathione-Sepharose beads (Amersham Pharmacia Biotech) following manufacturer's protocol.

In Vitro Methylation and Acetylation Assays

Methylation assays were performed as described. (Nishioka et al. (2002) supra. In brief, 2 μg of calf thymus histones (Sigma), synthetic Tat protein or recombinant GST-IκBα were incubated with 0, 0.5, 1 or 2 μg of recombinant Set9 (specific activity 182 mU/mg, Upstate) or 0, 1 and 2 μg of G9a (specific activity 98 mU/mg, Upstate) in a buffer containing 50 mM TrisHCl pH 8.5, 5 mM $MgCl_2$, 4 mM DTT and 1.1 μCi of $^3H$-labeled S-adenosyl methionine (SAM) (Perkin Elmer) 30 min at 30° C. Reactions were stopped with sodium dodecyl sulfate (SDS) sample buffer and fractionated in a 15% SDS-polyacrylamide gel electrophoresis (SDS-PAGE) gel. After Coomassie staining and destaining, gels were treated with Amplify (Amersham Biosciences) for 30 min, dried and exposed to hyper-film (Kodak) overnight. The reactions performed with Tat peptides contained 100 μM of the different peptides and 1 µg of Set9 enzyme and were fractionated in a 10-20% Tris-Tricine gel (BioRad). For mass-spectrometry analysis, reactions were performed in the presence of 2 mM SAM (New England Biolabs) and analyzed in a MALDI-TOF instrument. In vitro acetylation assays were performed as described. Ott et al. (1999) supra.

Co-Immunoprecipitation Experiments

HEK293 cells were transfected either with empty vector or a Tat-FLAG expressing vector using lipofectamine reagent (Invitrogen). Cells were lysed after 24 hr in 250 mM NaCl, 0.1% NP40, 20 mM NaH$_2$PO4 [pH 7.5], 5 mM EDTA, 30 mM sodium pyrophosphate, 10 mM NaF and protease inhibitors (Roche Molecular Biochemicals). Duplicates were pooled and 1 mg of lysate was immunoprecipitated either with α-Set9 antibody (Upstate) coupled to Protein A agarose beads (Invitrogen) or beads alone for 2 hr at 4° C. Beads were washed 5 times in lysis buffer, boiled in SDS loading buffer and analyzed by western blotting with polyclonal α-Set9 (Upstate) or monoclonal α-Flag (Sigma) antibodies.

For the immunoprecipitation (IP) studies in Jurkat clones, A72 and A2 cells were either non-stimulated or stimulated with 10 ng/ml TNFα (Biosource) for 18 h and immunoprecipitated as described above.

Immunofluorescence Studies

HeLa cells were plated into chamber slides (Nunc-lab Tek permanox slide chamber) and transfected with a Tat/FLAG expression vector with lipofectamine. After 24 h, cells were washed with phosphate buffered saline (PBS), heat fixed at 37° C. 5 min in a CO$_2$ incubator and perm/fixed in 3.9% paraformaldehyde, 1×PBS, and 0.01% Triton X100 for 10 min at room temperature (RT). Cells were then incubated in the blocking solution (1% goat serum, 1% horse serum, 0.1% cold fish skin gelatin, 0.01% TritonX100, 0.02% sodium azide in phosphate buffered saline (PBS)/0.01% Tween 20) overnight at 4° C. Polyclonal anti-Set9 antibody ("α-Set9") (Upstate) was used at a 1:200 dilution overnight at 4° C. followed with secondary goat-rabbit antibody Alexa 488 1:1000 1 hour at room temperature. Cells were then incubated with M2 monoclonal anti-FLAG ("α-FLAG") (Sigma) diluted 1:200 during 2 h at room temperature followed with the incubation of the goat anti-mouse antibody ("α-mouse") Alexa 568 diluted 1:2000 1 hour at room temperature (dark). The preparations were mounted with Biomeda Gel Mount, and slides visualized using a Zeiss Meta 510 Confocal Microscope (63× oil immersion).

Preparation and Use of Polyclonal α-meARM Antibodies

Chemically synthesized K51-methylated ARM peptides were conjugated to keyhole limpet hemocyanin (KLH, Pierce), mixed with complete Freund's adjuvant (FCA, Sigma), and injected into rabbits rabbit in a 118-day rabbit peptide protocol (performed by Covance, Denver, Pa.). The IgG fractions were isolated on affinity columns loaded with the same immunogens (Affi-Gel Hz Immunoaffinity Kit, Bio-Rad). For the Dot-Blot experiments, 0.1, 1, 10 and 100 ng of ARM peptides were spotted onto a nitrocellulose membrane, let dry and incubate with the anti-meARM ("α-meARM") antibodies or SA-HRP (streptavidin-horse radish peroxidase).

For the Western Blot of synthetic proteins, 12.5, 25, 50 and 100 ng of synthetic biotinylated Tat protein were incubated in a methylation reaction in the presence or absence of Set9 enzyme and loaded in a gel. For the detection of methylated Tat in cells, HEK293 cells were transfected with the Tat-expressing vectors with lipofectamine. Cells were lysed in IP buffer, and 5 mg of lysates immunoprecipitated with anti-Flag M2-agarose ("α-Flag M2-agarose"; anti-FLAG antibody coupled to agarose) (Sigma). For the blocking experiments, a 10× molar excess of the ARM wildtype or methylated at K51 were preincubated with the α-meARM antibody for 1 hour at room temperature.

RNAi and Transfection Experiments

In co-transfection experiments, human Set9 or Set9H297A (150 ng) were cotransfected in HeLa cells with the HIV LTR luciferase reporter (200 ng) and increasing amounts of EF1α-Tat expression vector (0, 2, 20, 200 ng) using lipofectamine reagent (Invitrogen). In the control experiment, EF1α-Tat was replaced by EF1α-RL. Cells were harvested 24 hr later and processed for luciferase or renilla assays (Promega).

Pre-designed Dharmacon siRNA pools targeting transcripts of the human Set9 gene as well as a control siRNA pool were transfected in HeLa cells using oligofectamine reagent (Invitrogen). After 48 hr, cells were retransfected with the HIV LTR luciferase construct (200 ng) together with increasing amounts of the EF1α-Tat expressing vectors (0, 2, 20, 200 ng) using lipofectamine (Invitrogen) and corresponding amounts of the empty pcDNA3.1 vector (Invitrogen). Cells were harvested 24 hr later and either processed by luciferase assays (Promega) or for Western Blot of total extracts with the α-Set9 antibody, α-actin (MP Biochemicals) or anti-FLAG (Sigma).

Chromatin Immunoprecipitation Experiments

Jurkat cells A2 were treated for 4 h with PMA (Sigma; 100 ng/ml) or dimethylsulfoxide (DMSO). Chromatin immunoprecipitation (ChIP) assays were performed using the ChIP assay kit (Upstate) with slight modifications. Briefly, cells were fixed with 1% formaldehyde (v/v) and fixation was stopped after 30 min by addition of glycine to 0.125M. Cells were lysed and sonicated (Model 500 Ultrasonic Dismembranator, Fisher Scientific) to generate DNA fragments 200-1000 bp in size. Lysates were incubated overnight with 5 µg of Set9 antibody. Immune complexes were recovered by incubation with protein A agarose beads for 1 h. After extensive washing, chromatin was eluted. Crosslinks were reversed, chromatin was treated with proteinase K, and DNA was isolated by phenol:chloroform:isoamyl alcohol (25:24:1) extraction. Immunoprecipitated chromatin was quantified by real-time PCR using the ABI 7700 Sequence Detection System (Applied Biosystems) and the 2× Hot Sybr real time PCR kit (McLab).

Primer sequences were as follows:

| | | |
|---|---|---|
| HIV LTR upstream: | 5'GAGCCCTCAGATCCTGCATA3', | (SEQ ID NO:73) |
| HIV LTR downstream: | 5'AGCTCCTCTGGTTTCCCTTT3', | (SEQ ID NO:74) |
| β-actin upstream: | 5'GCCAGCTGCAAGCCTTGG3', | (SEQ ID NO:75) |
| β-actin downstream: | 5'GCCACTGGGCCTCCATTC3', | (SEQ ID NO:76) |
| GFP upstream: | 5'ATGGTGAGCAAGGGCGAGGAG3', | (SEQ ID NO:77) |
| GFP downstream: | 5'GTGGTGCAGATGAACTTCAG3'. | (SEQ ID NO:78) |

The SDS 1.9.1 software (Applied Biosystems) was used for analysis, and the relative quantity of DNA in each ChIP sample was determined by comparison to the standard curve. The specificity of each PCR reaction was confirmed by melting curve analysis using the Dissociation Curve 1.0 software (Applied Biosystems).

AMAXA Nucleofection and Flow Cytometry

SiRNA-nucleofection of Jurkat A2 cells was performed as previously described. Mahmoudi et al. (2006) *J. Biol. Chem.* 281:19960. Cells were spun at 1000 rpm for 10 min, resuspended in solution R (Amaxa) and nucleofected with 2 µg of siRNA pools directed against Set9 gene or with a control siRNA pool (both Dharmacon) using program O-28. 72 h after nucleofection, cells were treated with PMA (0.4 or 2 ng/ml) or DMSO for 12 h. GFP expression was analyzed on a Calibur FACScan (Beckton Dickinson).

Results

Set9 is a Tat Methyltransferase.

To examine whether Tat is a substrate of the Set9 methyltransferase activity full-length synthetic Tat protein (72 amino acids) was incubated with recombinant Set9 and radiolabeled S-adenosyl-L-methionine (SAM). The Tat protein was methylated in response to increasing amounts of Set9 enzyme (FIG. 1A). No spontaneous methylation was observed in the presence of SAM alone. As expected, Set9 also methylated purified histones, predominantly histone H3, a known substrate of Set9. In contrast, methylation by Set9 was not observed with another recombinant protein, GST-IκBα. Incubation with the lysine methyltransferase G9a did not result in methylation of Tat, but led to the successful methylation of histones as expected (FIG. 1B). These results indicate that Tat is a specific in vitro substrate of Set9.

FIGS. 1A and 1B. Tat is a specific in vitro substrate of the lysine methyltransferase activity of Set9. A., Synthetic Tat (72 amino acids), histones purified from calf thymus or recombinant GST-IκBα were incubated in the presence of recombinant Set9 (0, 1 and 2 µg) in a reaction containing radiolabeled S-Adenosyl-methionine (SAM), a universal methyl donor. Tat methylation is visualized by autoradiography (top panels). Coomassie staining of the same gels are shown below. B. In vitro methylation reactions with synthetic Tat or histones using recombinant G9a enzyme (0, 1 and 2 µg).

Set9 Monomethylates Lysine 51.

Next, the site of methylation in Tat was mapped. Short synthetic peptides spanning the Tat sequence were generated and subjected to radioactive in vitro methylation assays with Set9. Methylation was observed with one peptide (45-58 amino acids) corresponding to the arginine-rich motif (ARM) of Tat (FIG. 2A). This result was confirmed by matrix-assisted laser desorption ionization time-of-flight (MALDI-TOF) mass spectrometry of the same reactions performed in the presence of nonradioactive SAM (FIG. 3). In this analysis a shift of 14 Da was detected in the methylated ARM peptide, corresponding to the addition of a single methyl group (FIG. 3). These results demonstrate that the ARM of Tat is monomethylated by Set9.

The Tat ARM contains two lysines, K50 and K51. Both residues are strictly conserved among HIV-1 viral isolates. To determine which lysine is the target for the Set9 methyltransferase activity, ARM peptides containing alanine substitutions at position K50, K51 or both, were generated. Methylation by Set9 was abrogated when K51 or both lysines were mutated, while mutation of K50 alone had no effect (FIG. 2B). The same result was observed in the analysis of the nonradioactive reactions by MALDI-TOF mass spectrometry (FIG. 2C). These data demonstrate that K51 in Tat is monomethylated by Set9.

FIGS. 2A-C. Tat is monomethylated by Set9 at lysine 51. A. In vitro methylation assays performed with short peptides spanning the Tat sequence in the presence of radiolabeled SAM. Peptides were separated on Tris-Tricine gels and visualized by autoradiography. B. ARM peptides (amino acids 45-58) with alanine substitutions for lysine 50 (K50A), lysine 51 (K51A) or both (K50, 51AA) were in vitro methylated by Set9 in the presence of radiolabeled SAM. C. MALDI-TOF mass-spectrometry analysis of nonradioactive methylation reactions performed with the wild type, K50A or K51A ARM peptides. Peptides were incubated with Set9 and SAM, SAM alone or only the reaction buffer. The sequences depicted in FIG. 2A are:

| | |
|---|---|
| ISYGRKKRRQRRRP; | (SEQ ID NO:26) |
| ISYGRAKRRQRRRP; | (SEQ ID NO:41) |
| ISYGRKARRQRRRP; and | (SEQ ID NO:42) |
| ISYGRAARRQRRRP. | (SEQ ID NO:43) |

Figure 3A:
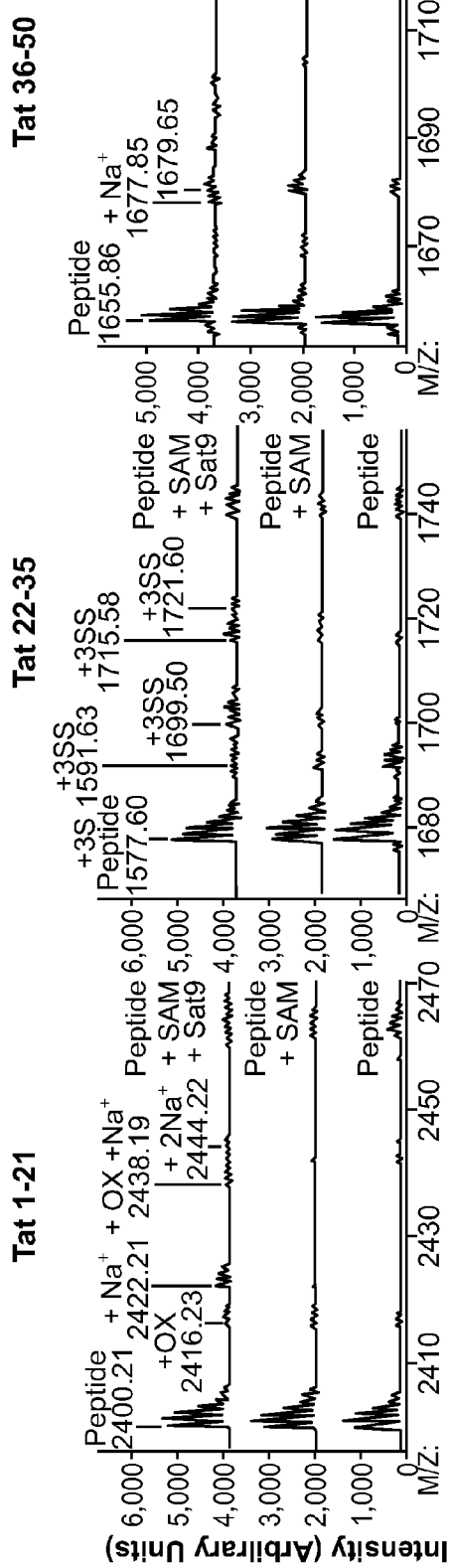
FIGS. 3A and 3B depict Set9 methylation of Tat peptides, as analyzed by MALDI-TOF.
Figure 3B:
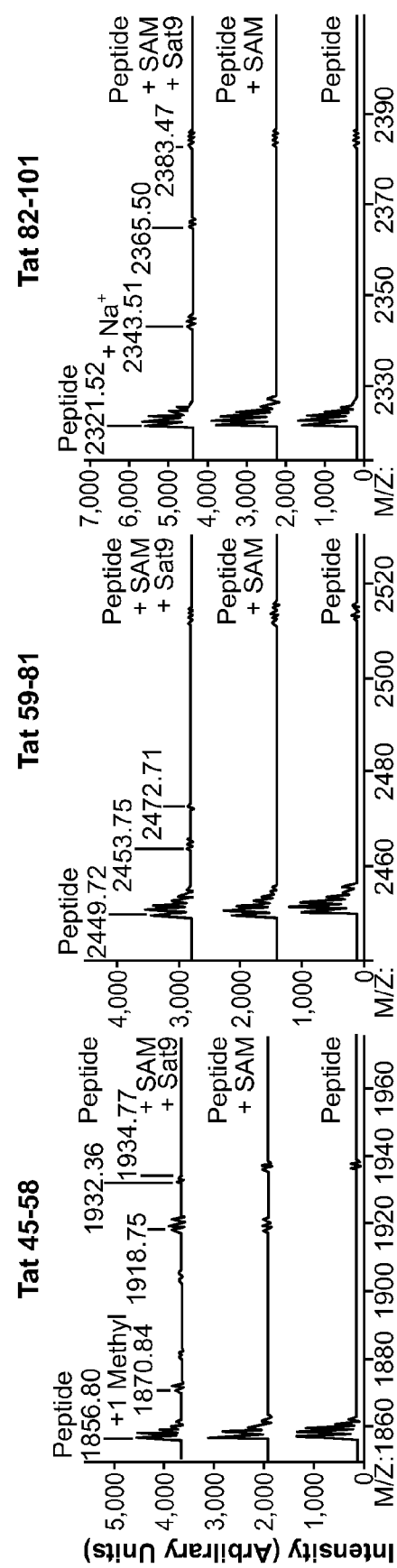

FIGS. 3A and 3B. Set9 methylation of Tat peptides analyzed by MALDI-TOF. The 6 peptides spanning the Tat sequence were subjected to methylation in a reaction containing Set9 and nonradioactive SAM and analyzed by MALDI-TOF mass-spectrometry analysis. FIG. 3A: Tat 1-21; Tat 22-35; and Tat 36-50. FIG. 3B: Tat 45-58; Tat 59-81; and Tat 82-101.

Acetylation of Lysine 50 Inhibits Methylation of Lysine 51.

Figures 4A, 4B:
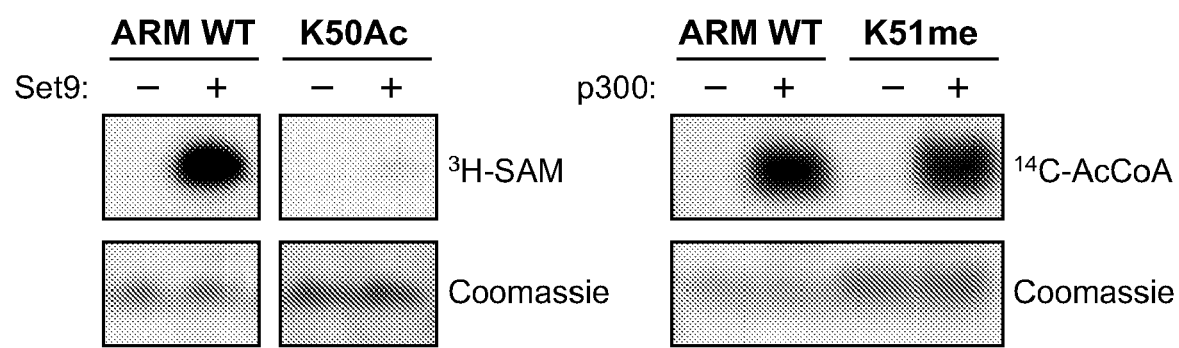
FIGS. 4A and 4B depict cross-regulation of lysine acetylation and methylation in the Tat ARM.

K50, the neighboring residue of K51, is the target of the acetyltransferases p300 and hGCN5. The crossregulation between Tat acetylation and methylation was studied. First, in vitro methylation experiments were performed with a synthetic ARM peptide carrying a single acetyl group at K50. No methylation signal was observed indicating that methylation at K51 cannot occur when K50 is acetylated (FIG. 4A). This result was confirmed when samples were analyzed by MALDI-TOF mass spectrometry.

In the reverse experiment, it was tested whether an ARM peptide carrying a monomethyl group at K51 can be acetylated by p300. Acetylation by p300 occurred regardless of the methylation status of K51 indicating that monomethylation of K51 does not alter the recognition site of the p300 acetyltransferase in Tat (FIG. 4B).

FIGS. 4A-C. Crossregulation of lysine acetylation and methylation in the Tat ARM. A. Radioactive in vitro methylation assay performed with synthetic ARM peptides corresponding to the unmodified Tat ARM (ARM wt) or the ARM peptide carrying an acetyl group at position 50 (K50Ac). No methylation of the acetylated peptide is detected. B. The ARM wt or an ARM peptide monomethylated at K51 (K51me) were in vitro acetylated with recombinant p300 and radiolabeled Acetyl Coenzyme A ($^{14}$C-AcCoA). ARMwt and K51me are both acetylated by p300. For all reactions, autoradiography is shown at the top, and coomassie staining of the peptides at the bottom.

In Vivo Recruitment of Set9 to the HIV Promoter

Figure 5A:
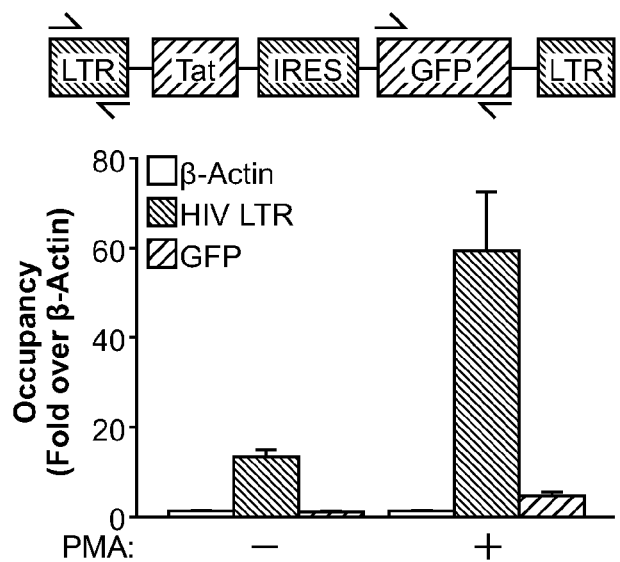
FIGS. 5A-C depict physical interaction of HIV Tat with endogenous Set9.

It was tested whether Set9 is recruited to the HIV LTR in vivo. Chromatin immunoprecipitation experiments were performed in Jurkat T cells latently infected with an HIV-based lentiviral vector (clone A2). Jordan et al. (2003) *EMBO J.* 22:1868. This vector is a minimal non-replicative HIV-1 genome flanked by two LTRs and containing the cDNA for Tat/FLAG and enhanced green fluorescent protein (GFP) expressed under the control of the HIV LTR (FIG. 5a). Gene expression is silenced in Jurkat A2 cells, but HIV transcription and Tat expression is induced after treatment with phorbol 12-myristate-13-acetate (PMA) or tumor necrosis factor α (TNFα). Jordan et al. (2003) supra.

Chromatin was prepared from Jurkat A2 cells treated with PMA or the solvent control and was immunoprecipitated with antibodies directed against endogenous Set9. Real-time PCR analysis of the immunoprecipitated material with primers specific for the HIV promoter showed that Set9, while present at the uninduced HIV LTR at low concentrations, was enriched in response to PMA (FIG. 5a). No association of Set9 with the GFP sequence was observed in uninduced cells; the signal slightly enhanced in response to PMA (FIG. 5a). These data show that Set9 is present at the HIV LTR and is specifically enriched during active transcription when Tat is produced.

Figure 5B:
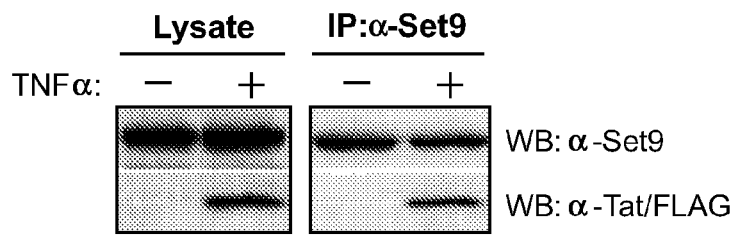

To examine whether Tat binds Set9 and may recruit the enzyme to the HIV promoter coimmunoprecipitation experiments were performed in Jurkat A2 cells. Tat expression was induced after treatment with TNFα, and cellular lysates were subjected to immunoprecipitations with Set9 antibodies. Tat was detected in the immunoprecipitated material by western blotting with α-FLAG antibodies demonstrating that Tat and Set9 interact in cells (FIG. 5b). This interaction was independent from the methylation status of K51 since the K51A mutant of Tat that cannot become methylated coimmunoprecipitated with endogenous Set9 as efficiently as wild type Tat (FIG. 5c).

Figure 5C:
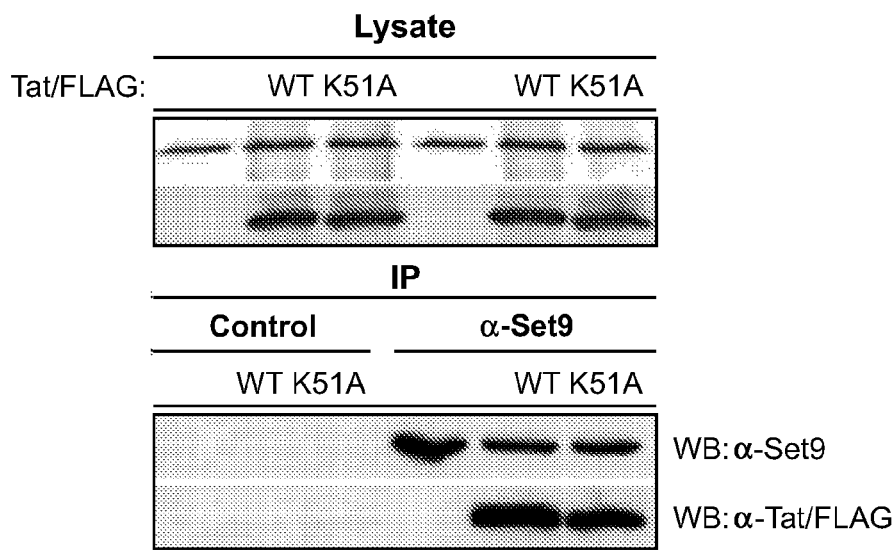

FIGS. 5A-C. HIV Tat interacts with endogenous Set9 and recruits Set9 to the HIV promoter. (a) Chromatin immunoprecipitation analysis of Set9 binding to the HIV LTR in Jurkat A2 cells treated with PMA for 4 h or left unstimulated. Real-time PCR was used to quantify the enrichment of indicated DNA regions after immunoprecipitation with α-Set9 antibodies. Quantities of immunoprecipitated DNA were normalized to input DNA and were expressed relative to the β-actin control. Average (mean±SD) of three PCR experiments are shown. (b) Coimmunoprecipitation of Tat and endogenous Set9 in Jurkat A2 cells treated with TNFα. Cellular lysates were immunoprecipitated with α-Set9 antibodies followed by western blotting with α-Set9 and α-FLAG antibodies. (c) Coimmunoprecipitations of Tat and endogenous Set9 in 293 cells transfected with Tat/FLAG (Tat WT), TatK51A/FLAG or the empty vector control. Equal amounts of protein were immunoprecipitated with α-Set9 antibodies or agarose beads alone and analyzed by western blotting with α-Set9 or α-FLAG antibodies.

Tat is Methylated at Lysine 51 in Cells.

To study Tat methylation in cells, rabbits were immunized with synthetic peptides corresponding to the methylated Tat ARM. The resulting antiserum (α-meARM) specifically recognized the monomethylated Tat ARM, but did not crossreact with unmodified, di- or trimethylated ARM peptides in dot blot experiments (FIG. 6).

Figure 6:
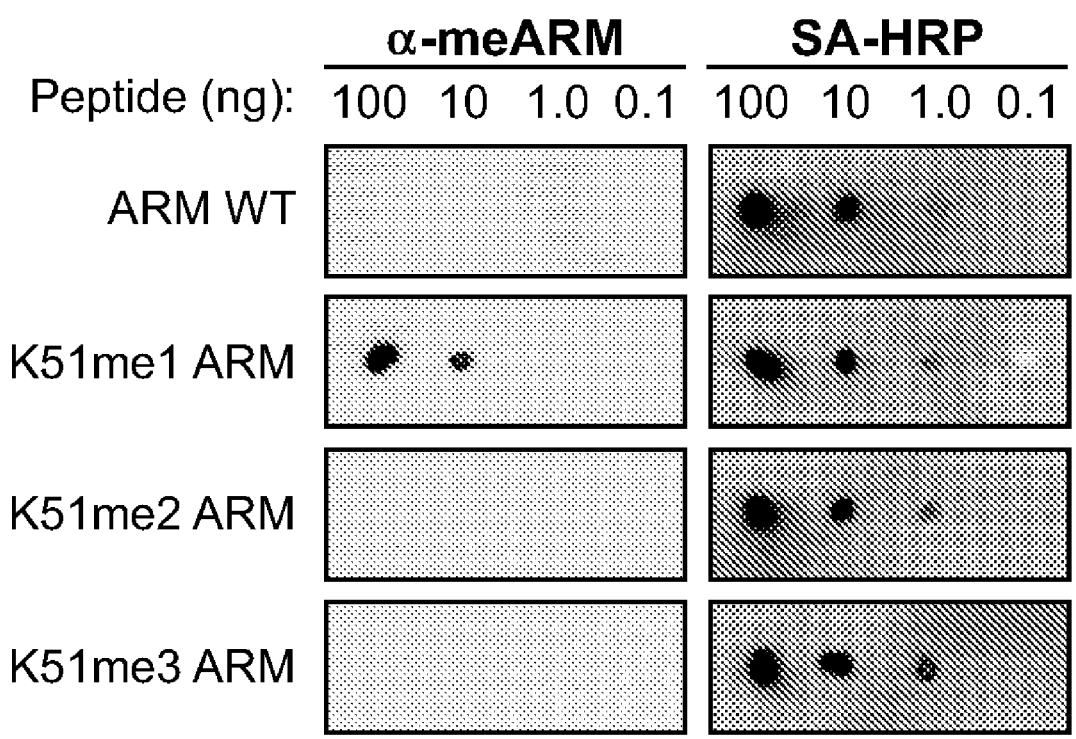
FIG. 6 depict dot-blot analysis of polyclonal antibodies specific for K51-monomethylated Tat.

FIG. 6. Dot-Blot analysis of the polyclonal antibodies specific for K51-monomethylated Tat. The specificity of the antibody was assessed by Dot Blot experiments. Serial dilutions of biotinylated ARM peptides, either nonmodified, mono-, di- or tri-methylated at K51 were spotted on a membrane (and blotted with the α-K51 methylated antibody). The antibody specifically detected the ARM peptide monomethylated at K51, and showed no reactivity against nonmodified ARM or ARM peptide di- or trimethylated.

The antiserum recognized the full-length Tat protein only after methylation by Set9 (FIG. 7A). No reactivity was observed with unmodified Tat even at high Tat concentrations (up to 0.1 μg). Total Tat levels in the reactions were visualized by immunoblotting with streptavidin-horseradish peroxidase conjugate (SA-HRP) that recognized the biotin label attached to the N terminus of Tat (FIG. 7A).

Next, the reactivity of affinity-purified anti-meARM immunoglobulins with cellular Tat was tested. HEK293 cells were transfected with the expression vector for Tat/FLAG or the empty vector control. Vectors expressing epitope-tagged versions of mutant Tat, where K51 had been changed to alanine (K51A) or arginine (K51R), were also included. Cell lysates were immunoprecipitated with α-FLAG agarose to isolate Tat followed by western blot analysis with α-meARM. A Tat-specific signal was only detected in samples expressing wild type Tat, but not in samples transfected with expression vectors for mutant Tat or the empty vector control (FIG. 7B). Wild type and mutant Tat proteins were expressed at similar levels as confirmed by western blot analysis with the M2 α-FLAG antibody (FIG. 7B).

When Tat/FLAG and Set9 were coexpressed in cells, Tat methylation levels were enhanced (FIG. 7C). Recognition of methylated Tat was blocked when α-meARM was preincubated with the methylated ARM peptide, while preincubation with the unmodified peptide had no effect (FIG. 7C). These data confirm the specificity of the antiserum for methylated Tat and demonstrate that Set9 is a Tat methyltransferase in cells.

FIGS. 7A-C. Generation of polyclonal antibodies specific for K51-monomethylated Tat. A. In vitro methylation reactions of biotinylated synthetic Tat (12.5, 25, 50 and 100 ng) with recombinant Set9 and nonlabeled SAM were analyzed by western blotting with α-meARM antibodies or horseradish peroxidase-coupled streptavidin (SA-HRP). B. Immunoprecipiations of Tat/FLAG or Tat/FLAG mutants (K51A/R) in transfected HEK293 cells followed by western blotting with α-meARM and α-FLAG antibodies. C. Immunoprecipitation/western blot analysis of Tat coexpressed with Set9 in HEK293 cells. The α-meARM antibodies were preincubated with milk (left panel), a 10× molar excess of K51-methylated ARM peptide (middle) or an unmodified peptide (right panel).

Methylation by Set9 Activates Tat Transcriptional Activity

Figure 9:
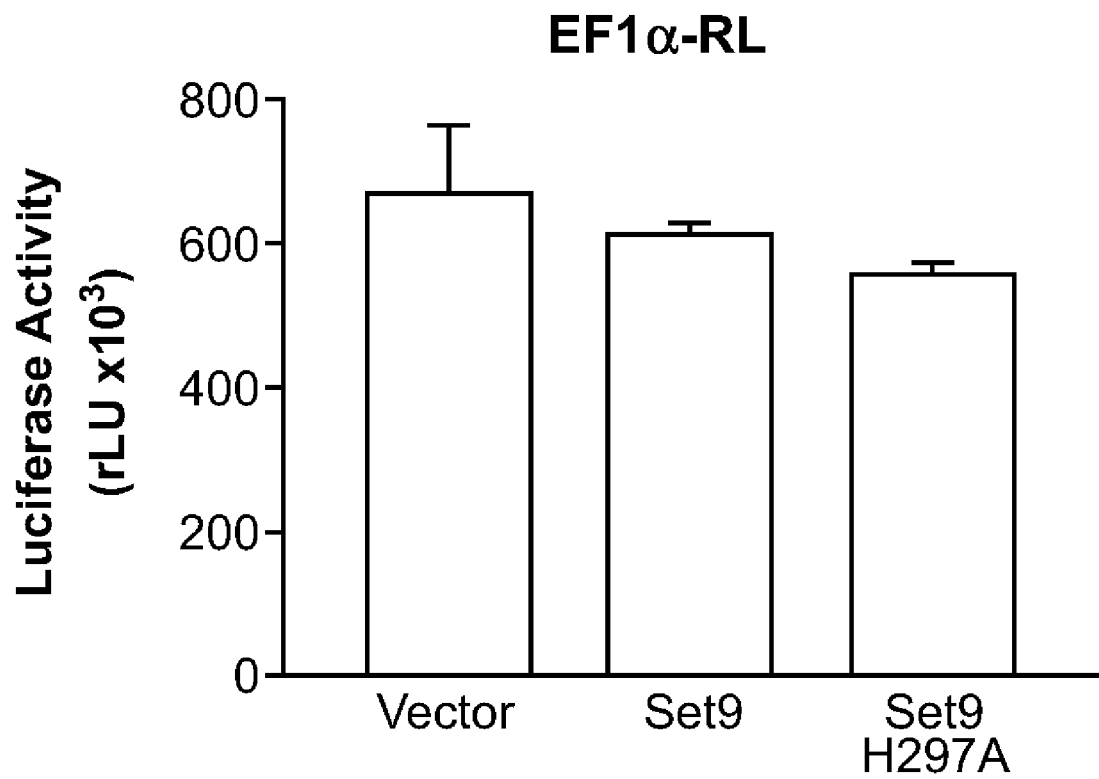
FIG. 9 depicts lack of an effect on the EF1-α promoter by Set9 or Set9H297A.
Figure 11A:
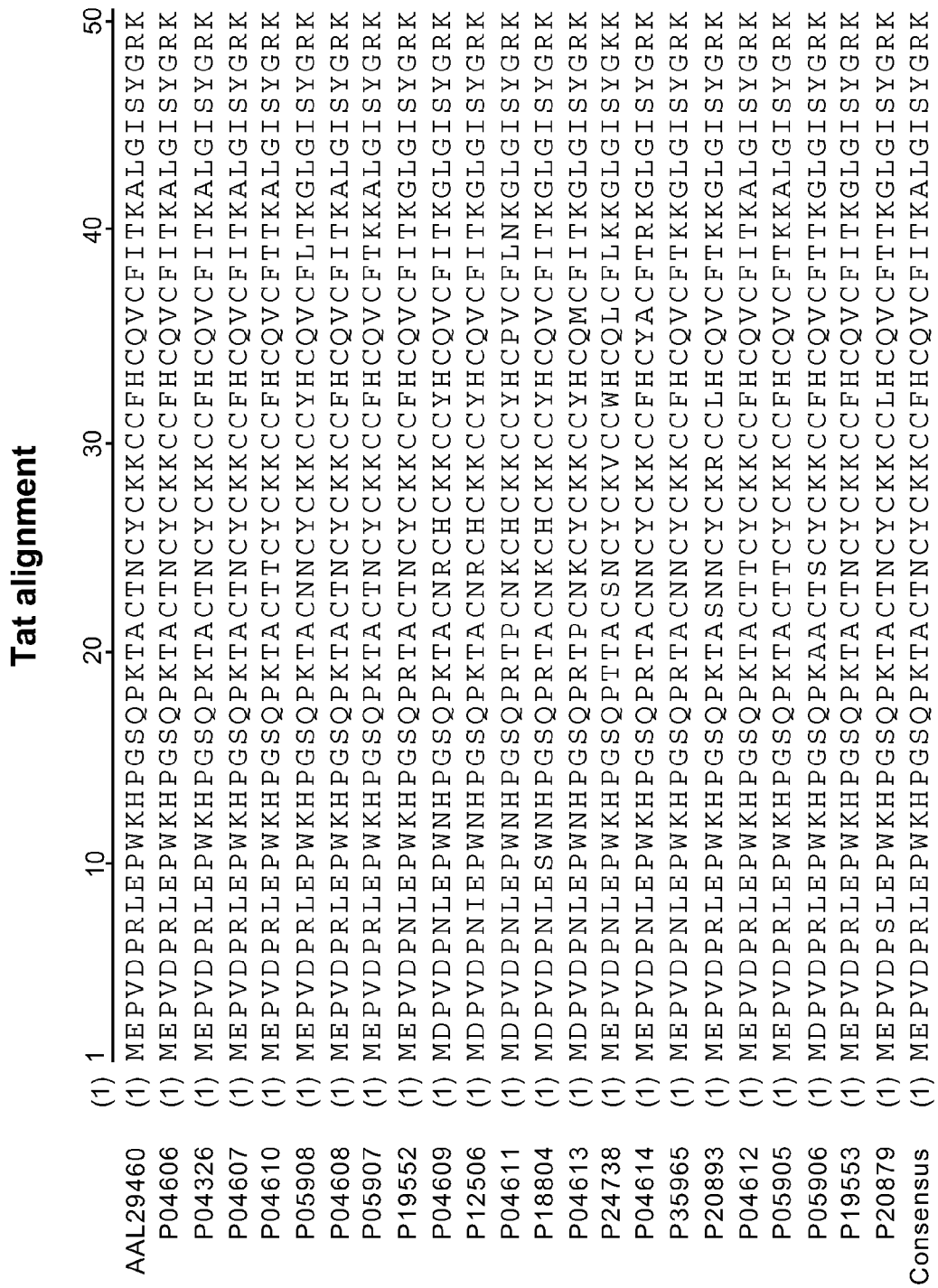

To investigate the biological role of Set9 during HIV transcription HeLa cells were transfected with an HIV LTR luciferase construct and expression vectors for Tat and Set9. Wild type, but not catalytically inactive Set9 (H297A) synergized with Tat in the transactivation of the HIV LTR demonstrating that Set9 functions as a coactivator of HIV transcription and that its methyltransferase activity is necessary for this coactivator function (FIG. 8a, left panel). No effect of Set9 was observed on the transcriptional activity of the TatK51A mutant indicating that Set9 primarily activates HIV transcription through methylation of Tat (FIG. 8a, right panel). In parallel, reporter assays were performed with a luciferase construct containing the elongation factor 1 α (EF-1α) promoter, which was driving Tat expression in these experiments (FIG. 9). No effect of Set9 was observed on the transcriptional activity of the EF-1a promoter excluding the possibility that Set9 activated Tat expression rather than Tat function in these experiments.

siRNAs specific for Set9 were introduced into HeLa cells to downregulate Set9 expression before transfection of the HIV LTR luciferase reporter and Tat. Set9 expression was efficiently downregulated 72 hours after siRNA transfections (FIG. 8b). At this time, Tat transactivation of the HIV LTR was reduced by 50 percent demonstrating that Set9 expression is necessary for full Tat function (FIG. 8b). No effect of the siRNAs was observed when the HIV LTR reporter was expressed in the absence of Tat or together with the TatK51A mutant indicating that the coactivator function of Set9 is dependent on K51 methylation in Tat (FIG. 8b). It was verified by western blotting that wild type and mutant Tat proteins were equally expressed, and that no difference in Tat expression was observed when Set9 was downregulated (FIG. 8b).

Finally, siRNAs specific for Set9 were introduced into Jurkat A2 cells using Amaxa nucleofection and confirmed by western blotting that Set9 expression was effectively downregulated (FIG. 8c). Following treatment with increasing amounts of PMA, activation of HIV gene expression was decreased in the absence of Set9 as measured by flow cytometry of GFP (FIG. 8c). These results show that Set9 is required for full Tat transactivation in the context of lentiviral infection.

FIGS. 8A-C. Set9 is a positive cofactor for Tat transactivation. (a) Expression vectors for wild type or catalytically inactive Set9 (H297A; 150 ng) were cotransfected with indicated amounts of wild type Tat or TatK51A expression vectors and the HIV LTR luciferase reporter (200 ng) into HeLa cells. Luciferase values were analyzed 24 hours after transfections. The average of three independent experiments (mean±SEM) is shown. (b) Western blot analysis of endogenous Set9 and Tat/FLAG in HeLa cells transfected with siRNAs directed against Set9 or nonrelevant control siRNAs and expression vectors for Tat/FLAG and Tat/FLAGK51A. Cells were cotransfected with the HIV LTR luciferase construct (200 ng) and increasing amounts of expression vectors for Tat/FLAG and Tat/FLAGK51A (0, 2, 20, 200 ng). Measurements of luciferase activity and western blotting were performed 24 h after plasmid transfections and 72 h after siRNA transfection. Luciferase values represent the average (mean±SEM) of three experiments while one representative experiment is shown for the western blot. (c) Western blotting of endogenous Set9 in Jurkat A2 cells 72 h after nucleofection of Set9 or control siRNAs using AMAXA nucleofection. A2 cells nucleofected with Set9 or control siRNAs were stimulated with increasing amounts of PMA for 12 h or were left unstimulated. GFP expression was measured by flow cytometry. The average (mean±SEM) of three independent experiments is shown.

FIG. 9. The EF1-α promoter is not affected by overexpression of Set9 or Set9H297A. The EF1α-RL reporter (20 ng) was cotransfected together with Set9 or Set9H297A (150 ng) in HeLa cells. Cells were harvested after 24 h, and *Renilla* activity was measured.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated peptide of from 10 amino acids to 50 amino acids in length, wherein the peptide comprises an amino acid sequence having at least 90% amino acid sequence identity to amino acids 42 through 60 of SEQ ID NO:1, wherein the amino acid sequence comprises a methylated lysine at a position corresponding to Lys-51 of the amino acid sequence set forth in SEQ ID NO:1.

2. The peptide of claim 1, wherein the amino acid sequence further comprises an acetylated lysine immediately amino-terminal to the methylated lysine.

3. The peptide of claim 1, wherein the peptide comprises the amino acid sequence SYGRKK$^{Me}$RRQR (SEQ ID NO:2).

4. The peptide of claim 1, wherein the methylated lysine is mono-methylated.

5. The peptide of claim 1, wherein the methylated lysine is di-methylated.

6. The peptide of claim 1, wherein the methylated lysine is tri-methylated.

7. The peptide of claim 1, wherein said peptide further comprises a heterologous amino acid sequence.

8. A composition comprising:
a) a peptide according to claim 1; and
b) a buffer.

9. The composition of claim 8, further comprising one or more of a salt, a solubilizing agent, a non-ionic detergent, and a protease inhibitor.

10. The composition of claim 8, further comprising a pharmaceutically acceptable excipient.

11. The composition of claim 8, further comprising an adjuvant.

12. The peptide of claim 1, wherein the peptide comprises an amino acid sequence having at least 95% amino acid sequence identity to amino acids 42 through 60 of SEQ ID NO:1.

13. The peptide of claim 1, wherein the peptide comprises an amino acid sequence having at least 99% amino acid sequence identity to amino acids 42 through 60 of SEQ ID NO:1.

14. The peptide of claim 1, wherein the peptide comprises an amino acid sequence selected from:
SYGRK$^{Ac}$K$^{Me}$RRQR (SEQ ID NO:3);
SYGRKK$^{Me}$R$^{Me}$RQR (SEQ ID NO:33);
SYGRK$^{Ac}$K$^{Me}$R$^{Me}$RQR (SEQ ID NO:34);

SYGRKK$^{Me}$R$^{Me}$R$^{Me}$QR (SEQ ID NO:35);
SYGRK$^{Ac}$K$^{Me}$R$^{Me}$R$^{Me}$QR (SEQ ID NO:36);
ISYGRKK$^{Me}$RRQR (SEQ ID NO:4);
ISYGRK$^{Ac}$K$^{Me}$RRQR (SEQ ID NO:5);
SYGRKK$^{Me}$RRQRR (SEQ ID NO:6);
SYGRK$^{Ac}$K$^{Me}$RRQRR (SEQ ID NO:7);
SYGRKK$^{Me}$RRQRQ (SEQ ID NO:8);
SYGRK$^{Ac}$K$^{Me}$RRQRQ (SEQ ID NO:9);
ISYGRKK$^{Me}$RRQRR (SEQ ID NO:10);
ISYGRK$^{Ac}$K$^{Me}$RRQRR (SEQ ID NO:11);
ISYGRKK$^{Me}$RRQRQ (SEQ ID NO:12);
ISYGRK$^{Ac}$K$^{Me}$RRQRQ (SEQ ID NO:13);
ISYGRKK$^{Me}$RRQRRR (SEQ ID NO:14);
ISYGRK$^{Ac}$K$^{Me}$RRQRRR (SEQ ID NO:15);
ISYGRKK$^{Me}$RRQRRG (SEQ ID NO:16);
ISYGRK$^{Ac}$K$^{Me}$RRQRRG (SEQ ID NO:17);
ISYGRKK$^{Me}$RRQRRK (SEQ ID NO:18);
ISYGRK$^{Ac}$K$^{Me}$RRQRRK (SEQ ID NO:19);
GISYGRKK$^{Me}$RRQRRRP (SEQ ID NO:20);
GISYGRK$^{Ac}$K$^{Me}$RRQRRRP (SEQ ID NO:21);
KGISYGRKK$^{Me}$RRQRRRPP (SEQ ID NO:22);
KGISYGRK$^{Ac}$K$^{Me}$RRQRRRPP (SEQ ID NO:23);
(A/G)KGISYGRKK$^{Me}$RRQRRRPPQ (SEQ ID NO:24); and
(A/G)KGISYGRK$^{Ac}$K$^{Me}$RRQRRRPPQ (SEQ ID NO:25).

* * * * *

SEQUENCE LISTING

<160> NUMBER OF SEQ ID NOS: 83

<210> SEQ ID NO 1
<211> LENGTH: 101
<212> TYPE: PRT
<213> ORGANISM: Artificial Sequence
<220> FEATURE:
<223> OTHER INFORMATION: consensus sequence

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu Ser Lys Lys Lys Val Glu Arg Glu Thr Glu
                85                  90                  95

Thr Asp Pro Phe Asp
            100

<210> SEQ ID NO 2
<211> LENGTH: 10
<212> TYPE: PRT
<213> ORGANISM: Artificial Sequence
<220> FEATURE:
<223> OTHER INFORMATION: synthetic peptide
<220> FEATURE:

```
<221> NAME/KEY: METHYLATION
<222> LOCATION: (6)...(6)

<400> SEQUENCE: 2

Ser Tyr Gly Arg Lys Lys Arg Arg Gln Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (5)...(5)
<220> FEATURE:
<221> NAME/KEY: METHYLATION
<222> LOCATION: (6)...(6)

<400> SEQUENCE: 3

Ser Tyr Gly Arg Lys Lys Arg Arg Gln Arg
1               5                   10

<210> SEQ ID NO 4
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (7)...(7)

<400> SEQUENCE: 4

Ile Ser Tyr Gly Arg Lys Lys Arg Arg Gln Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (6)...(6)
<220> FEATURE:
<221> NAME/KEY: METHYLATION
<222> LOCATION: (7)...(7)

<400> SEQUENCE: 5

Ile Ser Tyr Gly Arg Lys Lys Arg Arg Gln Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (6)...(6)

<400> SEQUENCE: 6

Ser Tyr Gly Arg Lys Lys Arg Arg Gln Arg Arg
1               5                   10

<210> SEQ ID NO 7
```

```
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (5)...(5)
<220> FEATURE:
<221> NAME/KEY: METHYLATION
<222> LOCATION: (6)...(6)

<400> SEQUENCE: 7

Ser Tyr Gly Arg Lys Lys Arg Arg Gln Arg Arg
1               5                   10

<210> SEQ ID NO 8
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (6)...(6)

<400> SEQUENCE: 8

Ser Tyr Gly Arg Lys Lys Arg Arg Gln Arg Gln
1               5                   10

<210> SEQ ID NO 9
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (5)...(5)
<220> FEATURE:
<221> NAME/KEY: METHYLATION
<222> LOCATION: (6)...(6)

<400> SEQUENCE: 9

Ser Tyr Gly Arg Lys Lys Arg Arg Gln Arg Gln
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (7)...(7)

<400> SEQUENCE: 10

Ile Ser Tyr Gly Arg Lys Lys Arg Arg Gln Arg Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (6)...(6)
<220> FEATURE:
<221> NAME/KEY: METHYLATION
```

```
<222> LOCATION: (7)...(6)

<400> SEQUENCE: 11

Ile Ser Tyr Gly Arg Lys Lys Arg Arg Gln Arg Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (7)...(7)

<400> SEQUENCE: 12

Ile Ser Thr Gly Arg Lys Lys Arg Arg Gln Arg Gln
1               5                   10

<210> SEQ ID NO 13
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (6)...(6)
<220> FEATURE:
<221> NAME/KEY: METHYLATION
<222> LOCATION: (7)...(7)

<400> SEQUENCE: 13

Ile Ser Tyr Gly Arg Lys Lys Arg Arg Gln Arg Gln
1               5                   10

<210> SEQ ID NO 14
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (7)...(7)

<400> SEQUENCE: 14

Ile Ser Tyr Gly Arg Lys Lys Arg Arg Gln Arg Arg Arg
1               5                   10

<210> SEQ ID NO 15
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (6)...(6)
<220> FEATURE:
<221> NAME/KEY: METHYLATION
<222> LOCATION: (7)...(7)

<400> SEQUENCE: 15

Ile Ser Tyr Gly Arg Lys Lys Arg Arg Gln Arg Arg Arg
1               5                   10

<210> SEQ ID NO 16
<211> LENGTH: 13
```

```
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (7)...(7)

<400> SEQUENCE: 16

Ile Ser Tyr Gly Arg Lys Lys Arg Arg Gln Arg Arg Gly
 1               5                  10

<210> SEQ ID NO 17
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (6)...(6)
<220> FEATURE:
<221> NAME/KEY: METHYLATION
<222> LOCATION: (7)...(7)

<400> SEQUENCE: 17

Ile Ser Tyr Gly Arg Lys Lys Arg Arg Gln Arg Arg Gly
 1               5                  10

<210> SEQ ID NO 18
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (7)...(7)

<400> SEQUENCE: 18

Ile Ser Tyr Gly Arg Lys Lys Arg Arg Gln Arg Arg Lys
 1               5                  10

<210> SEQ ID NO 19
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (6)...(6)
<220> FEATURE:
<221> NAME/KEY: METHYLATION
<222> LOCATION: (7)...(7)

<400> SEQUENCE: 19

Ile Ser Tyr Gly Arg Lys Lys Arg Arg Gln Arg Arg Lys
 1               5                  10

<210> SEQ ID NO 20
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (8)...(8)

<400> SEQUENCE: 20
```

```
Gly Ile Ser Tyr Gly Arg Lys Lys Arg Arg Gln Arg Arg Pro
1               5                   10                  15
```

<210> SEQ ID NO 21
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (7)...(7)
<220> FEATURE:
<221> NAME/KEY: METHYLATION
<222> LOCATION: (8)...(8)

<400> SEQUENCE: 21

```
Gly Ile Ser Tyr Gly Arg Lys Lys Arg Arg Gln Arg Arg Pro
1               5                   10                  15
```

<210> SEQ ID NO 22
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (9)...(9)

<400> SEQUENCE: 22

```
Lys Gly Ile Ser Tyr Gly Arg Lys Lys Arg Arg Gln Arg Arg Pro
1               5                   10                  15

Pro
```

<210> SEQ ID NO 23
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (8)...(8)
<220> FEATURE:
<221> NAME/KEY: METHYLATION
<222> LOCATION: (9)...(9)

<400> SEQUENCE: 23

```
Lys Gly Ile Ser Tyr Gly Arg Lys Lys Arg Arg Gln Arg Arg Pro
1               5                   10                  15

Pro
```

<210> SEQ ID NO 24
<211> LENGTH: 19
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1
<223> OTHER INFORMATION: Xaa is ala or gly
<220> FEATURE:
<221> NAME/KEY: METHYLATION
<222> LOCATION: (10)...(10)

<400> SEQUENCE: 24

```
Xaa Lys Gly Ile Ser Tyr Gly Arg Lys Lys Arg Arg Gln Arg Arg
1               5                   10                  15
```

Pro Pro Gln

<210> SEQ ID NO 25
<211> LENGTH: 19
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1
<223> OTHER INFORMATION: Xaa is ala or gly
<220> FEATURE:
<221> NAME/KEY: ACETYLATION
<222> LOCATION: (9)...(9)
<220> FEATURE:
<221> NAME/KEY: METHYLATION
<222> LOCATION: (10)...(10)

<400> SEQUENCE: 25

Xaa Lys Gly Ile Ser Tyr Gly Arg Lys Lys Arg Arg Gln Arg Arg
 1               5                  10                  15

Pro Pro Gln

<210> SEQ ID NO 26
<211> LENGTH: 14
<212> TYPE: PRT
<213> ORGANISM: Artificial Sequence
<220> FEATURE:
<223> OTHER INFORMATION: synthetic peptide

<400> SEQUENCE: 26

Ile Ser Tyr Gly Arg Lys Lys Arg Arg Gln Arg Arg Arg Pro
 1               5                  10

<210> SEQ ID NO 27
<211> LENGTH: 10
<212> TYPE: PRT
<213> ORGANISM: Artificial Sequence
<220> FEATURE:
<223> OTHER INFORMATION: synthetic peptide

<400> SEQUENCE: 27

Ser Tyr Gly Arg Lys Lys Arg Arg Gln Arg
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: synthetic peptide

<400> SEQUENCE: 28

Ile Ser Tyr Gly Arg Lys Lys Arg Arg Gln Arg Arg
 1               5                  10

<210> SEQ ID NO 29
<211> LENGTH: 306
<212> TYPE: DNA
<213> ORGANISM: human immunodeficiency virus

<400> SEQUENCE: 29
atggagccag tagatcctag actagagccc tggaagcatc caggaagtca gcctaaaact      60
gcttgtacca attgctattg taaaaagtgt tgctttcatt gccaagtttg tttcataaca     120
aaagccttag gcatctccta tggcaggaag aagcggagac agcgacgaag acctcctcaa     180

```
ggcagtcaga ctcatcaagt ttctctatca aagcaaccca cctcccaatc ccgaggggac    240
ccgacaggcc cgaaggaatc gaagaagaag gtggagagag agacagagac agatccattc    300
gattag                                                               306

<210> SEQ ID NO 30
<211> LENGTH: 30
<212> TYPE: DNA
<213> ORGANISM: human immunodeficiency virus

<400> SEQUENCE: 30
tcctatggca ggaagaagcg gagacagcga                                      30

<210> SEQ ID NO 31
<211> LENGTH: 366
<212> TYPE: PRT
<213> ORGANISM: Homo sapiens

<400> SEQUENCE: 31
```

Met Asp Ser Asp Asp Glu Met Val Glu Glu Ala Val Glu Gly His Leu
 1               5                  10                  15

Asp Asp Asp Gly Leu Pro His Gly Phe Cys Thr Val Thr Tyr Ser Ser
             20                  25                  30

Thr Asp Arg Phe Glu Gly Asn Phe Val His Gly Glu Lys Asn Gly Arg
         35                  40                  45

Gly Lys Phe Phe Phe Phe Asp Gly Ser Thr Leu Glu Gly Tyr Tyr Val
     50                  55                  60

Asp Asp Ala Leu Gln Gly Gln Gly Val Tyr Thr Tyr Glu Asp Gly Gly
 65                  70                  75                  80

Val Leu Gln Gly Thr Tyr Val Asp Gly Glu Leu Asn Gly Pro Ala Gln
                 85                  90                  95

Glu Tyr Asp Thr Asp Gly Arg Leu Ile Phe Lys Gly Gln Tyr Lys Asp
            100                 105                 110

Asn Ile Arg His Gly Val Cys Trp Ile Tyr Tyr Pro Asp Gly Gly Ser
        115                 120                 125

Leu Val Gly Glu Val Asn Glu Asp Gly Glu Met Thr Gly Glu Lys Ile
    130                 135                 140

Ala Tyr Val Tyr Pro Asp Glu Arg Thr Ala Leu Tyr Gly Lys Phe Ile
145                 150                 155                 160

Asp Gly Glu Met Ile Glu Gly Lys Leu Ala Thr Leu Met Ser Thr Glu
                165                 170                 175

Glu Gly Arg Pro His Phe Glu Leu Met Pro Gly Asn Ser Val Tyr His
            180                 185                 190

Phe Asp Lys Ser Thr Ser Ser Cys Ile Ser Thr Asn Ala Leu Leu Pro
        195                 200                 205

Asp Pro Tyr Glu Ser Glu Arg Val Tyr Val Ala Glu Ser Leu Ile Ser
    210                 215                 220

Ser Ala Gly Glu Gly Leu Phe Ser Lys Val Ala Val Gly Pro Asn Thr
225                 230                 235                 240

Val Met Ser Phe Tyr Asn Gly Val Arg Ile Thr His Gln Glu Val Asp
                245                 250                 255

Ser Arg Asp Trp Ala Leu Asn Gly Asn Thr Leu Ser Leu Asp Glu Glu
            260                 265                 270

Thr Val Ile Asp Val Pro Glu Pro Tyr Asn His Val Ser Lys Tyr Cys
        275                 280                 285

Ala Ser Leu Gly His Lys Ala Asn His Ser Phe Thr Pro Asn Cys Ile

```
                290                 295                 300
Tyr Asp Met Phe Val His Pro Arg Phe Gly Pro Ile Lys Cys Ile Arg
305                 310                 315                 320

Thr Leu Arg Ala Val Glu Ala Asp Glu Glu Leu Thr Val Ala Tyr Gly
                325                 330                 335

Tyr Asp His Ser Pro Pro Gly Lys Ser Gly Pro Glu Ala Pro Glu Trp
                340                 345                 350

Tyr Gln Val Glu Leu Lys Ala Phe Gln Ala Thr Gln Gln Lys
                355                 360                 365

<210> SEQ ID NO 32
<211> LENGTH: 1101
<212> TYPE: DNA
<213> ORGANISM: Homo sapiens

<400> SEQUENCE: 32
atggatagcg acgacgagat ggtggaggag gcggtggaag ggcacctgga cgatgacgga      60
ttaccgcacg ggttctgcac agtcacctac tcctccacag acagatttga ggggaacttt    120
gttcacggag aaaagaacgg acgggggaag ttcttcttct ttgatggcag caccctggag    180
gggtattatg tggatgatgc cttgcagggc cagggagttt acacttacga agatggggga    240
gttctccagg gcacgtatgt agacggagag ctgaacggtc cagcccagga atatgacaca    300
gatgggagac tgatcttcaa ggggcagtat aaagataaca ttcgtcatgg agtgtgctgg    360
atatattacc cagatggagg aagccttgta ggagaagtaa atgaagatgg ggagatgact    420
ggagagaaga tagcctatgt gtaccctgat gagaggaccg cactttatgg gaaatttatt    480
gatggagaga tgatagaagg caaactggct acccttatgt ccactgaaga agggaggcct    540
cactttgaac tgatgcctgg aaattcagtg taccactttg ataagtcgac ttcatcttgc    600
atttctacca atgctcttct tccagatcct tatgaatcag aaagggttta tgttgctgaa    660
tctcttattt ccagtgctgg agaaggactt ttttcaaagg tagctgtggg acctaatact    720
gttatgtctt tttataatgg agttcgaatt acacaccaag aggttgacag cagggactgg    780
gcccttaatg ggaacaccct ctcccttgat gaagaaacgg tcattgatgt gcctgagccc    840
tataaccacg tatccaagta ctgtgcctcc ttgggacaca aggcaaatca ctccttcact    900
ccaaactgca tctacgatat gtttgtccac cccgttttg ggcccatcaa atgcatccgc    960 acccctgagag cagtggaggc cgatgaagag ctcaccgttg cctatggcta tgaccacagc   1020
ccccccggga gagtgggcc tgaagcccct gagtggtacc aggtggagct gaaggccttc   1080
caggccaccc agcaaaagtg a                                             1101

<210> SEQ ID NO 33
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (6)...(6)
<220> FEATURE:
<221> NAME/KEY: METHYLATION
<222> LOCATION: (7)...(7)

<400> SEQUENCE: 33

Ser Tyr Gly Arg Lys Lys Arg Arg Gln Arg
1               5                   10
```

```
<210> SEQ ID NO 34
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (5)...(5)
<220> FEATURE:
<221> NAME/KEY: METHYLATION
<222> LOCATION: (6)...(6)
<220> FEATURE:
<221> NAME/KEY: METHYLATION
<222> LOCATION: (7)...(7)

<400> SEQUENCE: 34

Ser Tyr Gly Arg Lys Lys Arg Arg Gln Arg
1               5                   10

<210> SEQ ID NO 35
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: (6)...(6)
<220> FEATURE:
<221> NAME/KEY: METHYLATION
<222> LOCATION: (7)...(7)
<220> FEATURE:
<221> NAME/KEY: METHYLATION
<222> LOCATION: (8)...(8)

<400> SEQUENCE: 35

Ser Tyr Gly Arg Lys Lys Arg Arg Gln Ala Arg
1               5                   10

<210> SEQ ID NO 36
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: ACETYLATION
<222> LOCATION: (5)...(5)
<220> FEATURE:
<221> NAME/KEY: METHYLATION
<222> LOCATION: (6)...(6)
<220> FEATURE:
<221> NAME/KEY: METHYLATION
<222> LOCATION: (7)...(7)
<220> FEATURE:
<221> NAME/KEY: METHYLATION
<222> LOCATION: (8)...(8)

<400> SEQUENCE: 36

Ser Tyr Gly Arg Lys Lys Arg Arg Gln Arg
1               5                   10

<210> SEQ ID NO 37
<211> LENGTH: 10
<212> TYPE: PRT
<213> ORGANISM: Artificial Sequence
<220> FEATURE:
<223> OTHER INFORMATION: synthetic epitope tag

<400> SEQUENCE: 37

Cys Tyr Pro Tyr Asp Val Pro Asp Tyr Ala
1               5                   10
```

```
<210> SEQ ID NO 38
<211> LENGTH: 8
<212> TYPE: PRT
<213> ORGANISM: Artificial Sequence
<220> FEATURE:
<223> OTHER INFORMATION: synthetic epitope tag

<400> SEQUENCE: 38

Asp Tyr Lys Asp Asp Asp Asp Lys
 1               5

<210> SEQ ID NO 39
<211> LENGTH: 10
<212> TYPE: PRT
<213> ORGANISM: Artificial Sequence
<220> FEATURE:
<223> OTHER INFORMATION: synthetic epitope tag

<400> SEQUENCE: 39

Glu Gln Lys Leu Ile Ser Glu Glu Asp Leu
 1               5                  10

<210> SEQ ID NO 40
<211> LENGTH: 6
<212> TYPE: PRT
<213> ORGANISM: Artificial Sequence
<220> FEATURE:
<223> OTHER INFORMATION: synthetic linker

<400> SEQUENCE: 40

Gly Gly Gly Ser Gly Gly
 1               5

<210> SEQ ID NO 41
<211> LENGTH: 14
<212> TYPE: PRT
<213> ORGANISM: Artificial Sequence
<220> FEATURE:
<223> OTHER INFORMATION: synthetic peptide

<400> SEQUENCE: 41

Ile Ser Tyr Gly Arg Ala Lys Arg Arg Gln Arg Arg Arg Pro
 1               5                  10

<210> SEQ ID NO 42
<211> LENGTH: 14
<212> TYPE: PRT
<213> ORGANISM: Artificial Sequence
<220> FEATURE:
<223> OTHER INFORMATION: synthetic peptide

<400> SEQUENCE: 42

Ile Ser Tyr Gly Arg Lys Ala Arg Arg Gln Arg Arg Arg Pro
 1               5                  10

<210> SEQ ID NO 43
<211> LENGTH: 14
<212> TYPE: PRT
<213> ORGANISM: Artificial Sequence
<220> FEATURE:
<223> OTHER INFORMATION: synthetic peptide

<400> SEQUENCE: 43

Ile Ser Tyr Gly Arg Ala Ala Arg Arg Gln Arg Arg Arg Pro
 1               5                  10
```

-continued

```
<210> SEQ ID NO 44
<211> LENGTH: 101
<212> TYPE: PRT
<213> ORGANISM: human immunodeficiency virus

<400> SEQUENCE: 44

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu Ser Lys Lys Lys Val Glu Arg Glu Thr Glu
                85                  90                  95

Thr Asp Pro Phe Asp
            100

<210> SEQ ID NO 45
<211> LENGTH: 86
<212> TYPE: PRT
<213> ORGANISM: human immunodeficiency virus

<400> SEQUENCE: 45

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 46
<211> LENGTH: 86
<212> TYPE: PRT
<213> ORGANISM: human immunodeficiency virus

<400> SEQUENCE: 46

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85
```

```
<210> SEQ ID NO 47
<211> LENGTH: 86
<212> TYPE: PRT
<213> ORGANISM: human immunodeficiency virus

<400> SEQUENCE: 47

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Gly Pro Lys Glu
                85

<210> SEQ ID NO 48
<211> LENGTH: 86
<212> TYPE: PRT
<213> ORGANISM: human immunodeficiency virus

<400> SEQUENCE: 48

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
            20                  25                  30

His Cys Gln Val Cys Phe Thr Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Gly Pro Lys Glu
                85

<210> SEQ ID NO 49
<211> LENGTH: 101
<212> TYPE: PRT
<213> ORGANISM: human immunodeficiency virus

<400> SEQUENCE: 49

Met Glu Pro Val Asp Pro Arg Leu Glu Pro Trp Lys His Pro Gly Ser
1               5                   10                  15

Gln Pro Lys Thr Ala Cys Asn Asn Cys Tyr Cys Lys Lys Cys Cys Tyr
            20                  25                  30

His Cys Gln Val Cys Phe Leu Thr Lys Gly Leu Gly Ile Ser Tyr Gly
        35                  40                  45

Arg Lys Lys Arg Arg Gln Arg Arg Gly Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Pro Lys Glu Ser Lys Glu Lys Val Glu Arg Glu Thr Glu Thr
                85                  90                  95

Asp Pro Ala Val Gln
            100
```

-continued

```
<210> SEQ ID NO 50
<211> LENGTH: 86
<212> TYPE: PRT
<213> ORGANISM: human immunodeficiency virus

<400> SEQUENCE: 50

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85

<210> SEQ ID NO 51
<211> LENGTH: 101
<212> TYPE: PRT
<213> ORGANISM: human immunodeficiency virus

<400> SEQUENCE: 51

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Thr Lys Lys Ala Leu Gly Ile Ser Tyr Gly
        35                  40                  45

Arg Lys Lys Arg Arg Gln Arg Arg Ala His Gln Asp Ser Gln Asn
    50                  55                  60

His Gln Ala Ser Leu Ser Lys Gln Pro Ser Ser Gln Thr Arg Gly Asp
65                  70                  75                  80

Pro Thr Gly Pro Lys Glu Pro Lys Lys Glu Val Glu Arg Glu Ala Glu
                85                  90                  95

Thr Asp Pro Leu Asp
                100

<210> SEQ ID NO 52
<211> LENGTH: 101
<212> TYPE: PRT
<213> ORGANISM: human immunodeficiency virus

<400> SEQUENCE: 52

Met Glu Pro Val Asp Pro Asn Leu Glu Pro Trp Lys His Pro Gly Ser
1               5                   10                  15

Gln Pro Arg Thr Ala Cys Thr Asn Cys Tyr Cys Lys Lys Cys Cys Phe
            20                  25                  30

His Cys Gln Val Cys Phe Ile Thr Lys Gly Leu Gly Ile Ser Tyr Gly
        35                  40                  45

Arg Lys Lys Arg Arg Gln Arg Gln Arg Ala Pro Asp Ser Ser Gln Asn
    50                  55                  60

His Gln Asp Ser Leu Ser Lys Gln Pro Ser Ser Gln Pro Arg Gly Asp
65                  70                  75                  80

Pro Thr Gly Pro Lys Glu Ser Lys Lys Glu Val Glu Arg Glu Thr Glu
                85                  90                  95
```

Thr Asp Pro Leu Asp
            100

<210> SEQ ID NO 53
<211> LENGTH: 86
<212> TYPE: PRT
<213> ORGANISM: human immunodeficiency virus

<400> SEQUENCE: 53

Met Asp Pro Val Asp Pro Asn Leu Glu Pro Trp Asn His Pro Gly Ser
1               5                   10                  15

Gln Pro Lys Thr Ala Cys Asn Arg Cys His Cys Lys Lys Cys Cys Tyr
            20                  25                  30

His Cys Gln Val Cys Phe Ile Thr Lys Gly Leu Gly Ile Ser Tyr Gly
        35                  40                  45

Arg Lys Lys Arg Arg Gln Arg Arg Pro Ser Gln Gly Gly Gln Thr
    50                  55                  60

His Gln Asp Pro Ile Pro Lys Gln Pro Ser Ser Gln Pro Arg Gly Asn
65                  70                  75                  80

Pro Thr Gly Pro Lys Glu
            85

<210> SEQ ID NO 54
<211> LENGTH: 86
<212> TYPE: PRT
<213> ORGANISM: human immunodeficiency virus

<400> SEQUENCE: 54

Met Asp Pro Val Asp Pro Asn Ile Glu Pro Trp Asn His Pro Gly Ser
1               5                   10                  15

Gln Pro Lys Thr Ala Cys Asn Arg Cys His Cys Lys Lys Cys Cys Tyr
            20                  25                  30

His Cys Gln Val Cys Phe Ile Thr Lys Gly Leu Gly Ile Ser Tyr Gly
        35                  40                  45

Arg Lys Lys Arg Arg Gln Arg Arg Pro Ser Gln Gly Gly Gln Thr
    50                  55                  60

His Gln Asp Pro Ile Pro Lys Gln Pro Ser Ser Gln Pro Arg Gly Asp
65                  70                  75                  80

Pro Thr Gly Pro Lys Glu
            85

<210> SEQ ID NO 55
<211> LENGTH: 99
<212> TYPE: PRT
<213> ORGANISM: human immunodeficiency virus

<400> SEQUENCE: 55

Met Asp Pro Val Asp Pro Asn Leu Glu Pro Trp Asn His Pro Gly Ser
1               5                   10                  15

Gln Pro Arg Thr Pro Cys Asn Lys Cys His Cys Lys Lys Cys Cys Tyr
            20                  25                  30

His Cys Pro Val Cys Phe Leu Asn Lys Gly Leu Gly Ile Ser Tyr Gly
        35                  40                  45

Arg Lys Lys Arg Arg Gln Arg Arg Gly Pro Pro Gln Gly Gly Gln Ala
    50                  55                  60

His Gln Val Pro Ile Pro Lys Gln Pro Ser Ser Gln Pro Arg Gly Asp
65                  70                  75                  80

Pro Thr Gly Pro Lys Glu Gln Lys Lys Lys Val Glu Ser Glu Ala Glu

```
                        85                  90                  95

Thr Asp Pro

<210> SEQ ID NO 56
<211> LENGTH: 86
<212> TYPE: PRT
<213> ORGANISM: human immunodeficiency virus

<400> SEQUENCE: 56

Met Asp Pro Val Asp Pro Asn Leu Glu Ser Trp Asn His Pro Gly Ser
1               5                   10                  15

Gln Pro Arg Thr Ala Cys Asn Lys Cys His Cys Lys Lys Cys Cys Tyr
            20                  25                  30

His Cys Gln Val Cys Phe Ile Thr Lys Gly Leu Gly Ile Ser Tyr Gly
        35                  40                  45

Arg Lys Lys Arg Arg Gln Arg Arg Lys Pro Pro Gln Gly Asp Gln Ala
    50                  55                  60

His Gln Val Pro Ile Pro Glu Gln Pro Ser Ser Gln Ser Arg Gly Asp
65                  70                  75                  80

Pro Thr Gly Pro Lys Lys
                85

<210> SEQ ID NO 57
<211> LENGTH: 87
<212> TYPE: PRT
<213> ORGANISM: human immunodeficiency virus

<400> SEQUENCE: 57

Met Asp Pro Val Asp Pro Asn Leu Glu Pro Trp Asn His Pro Gly Ser
1               5                   10                  15

Gln Pro Arg Thr Pro Cys Asn Lys Cys Tyr Cys Lys Lys Cys Cys Tyr
            20                  25                  30

His Cys Gln Met Cys Phe Ile Thr Lys Gly Leu Gly Ile Ser Tyr Gly
        35                  40                  45

Arg Lys Lys Arg Arg Gln Arg Arg Pro Pro Gln Gly Asn Gln Ala
    50                  55                  60

His Gln Asp Pro Leu Pro Glu Gln Pro Ser Ser Gln His Arg Gly Asp
65                  70                  75                  80

His Pro Thr Gly Pro Lys Glu
                85

<210> SEQ ID NO 58
<211> LENGTH: 101
<212> TYPE: PRT
<213> ORGANISM: human immunodeficiency virus

<400> SEQUENCE: 58

Met Glu Pro Val Asp Pro Asn Leu Glu Pro Trp Lys His Pro Gly Ser
1               5                   10                  15

Gln Pro Thr Thr Ala Cys Ser Asn Cys Tyr Cys Lys Val Cys Cys Trp
            20                  25                  30

His Cys Gln Leu Cys Phe Leu Lys Lys Gly Leu Gly Ile Ser Tyr Gly
        35                  40                  45

Lys Lys Lys Arg Lys Pro Arg Arg Gly Pro Pro Gln Gly Ser Lys Asp
    50                  55                  60

His Gln Thr Leu Ile Pro Lys Gln Pro Leu Pro Gln Ser Gln Arg Val
65                  70                  75                  80

Ser Ala Gly Gln Glu Glu Ser Lys Lys Lys Val Glu Ser Lys Ala Lys
```

```
                 85                  90                  95

Thr Asp Arg Phe Ala
                100

<210> SEQ ID NO 59
<211> LENGTH: 101
<212> TYPE: PRT
<213> ORGANISM: human immundeficiency virus

<400> SEQUENCE: 59

Met Glu Pro Val Asp Pro Asn Leu Glu Pro Trp Lys His Pro Gly Ser
1               5                   10                  15

Gln Pro Arg Thr Ala Cys Asn Asn Cys Tyr Cys Lys Lys Cys Cys Phe
            20                  25                  30

His Cys Tyr Ala Cys Phe Thr Arg Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Ala Ser Leu Ser Lys Gln Pro Ala Ser Gln Ser Arg Gly Asp
65                  70                  75                  80

Pro Thr Gly Pro Thr Glu Ser Lys Lys Lys Val Glu Arg Glu Thr Glu
                85                  90                  95

Thr Asp Pro Phe Asp
                100

<210> SEQ ID NO 60
<211> LENGTH: 101
<212> TYPE: PRT
<213> ORGANISM: human immunodeficiency virus

<400> SEQUENCE: 60

Met Glu Pro Val Asp Pro Asn Leu Glu Pro Trp Lys His Pro Gly Ser
1               5                   10                  15

Gln Pro Arg Thr Ala Cys Asn Asn Cys Tyr Cys Lys Lys Cys Cys Phe
            20                  25                  30

His Cys Gln Val Cys Phe Thr Lys Lys Gly Leu Gly Ile Ser Tyr Gly
        35                  40                  45

Arg Lys Lys Arg Arg Gln Arg Arg Pro Pro Gln Asp Ser Gln Thr
    50                  55                  60

His Gln Ser Ser Leu Ser Lys Gln Pro Thr Ser Gln Leu Arg Gly Asp
65                  70                  75                  80

Pro Thr Gly Pro Thr Glu Ser Lys Lys Lys Val Glu Arg Glu Thr Glu
                85                  90                  95

Thr Asp Pro Val His
                100

<210> SEQ ID NO 61
<211> LENGTH: 101
<212> TYPE: PRT
<213> ORGANISM: human immunodeficiency virus

<400> SEQUENCE: 61

Met Glu Pro Val Asp Pro Arg Leu Glu Pro Trp Lys His Pro Gly Ser
1               5                   10                  15

Gln Pro Lys Thr Ala Ser Asn Asn Cys Tyr Cys Lys Arg Cys Cys Leu
            20                  25                  30

His Cys Gln Val Cys Phe Thr Lys Lys Gly Leu Gly Ile Ser Tyr Gly
        35                  40                  45
```

```
Arg Lys Lys Arg Arg Gln Arg Arg Ala Pro Gln Asp Ser Lys Thr
    50                  55                  60

His Gln Val Ser Leu Ser Lys Gln Pro Ala Ser Gln Pro Arg Gly Asp
 65                  70                  75                  80

Pro Thr Gly Pro Lys Glu Ser Lys Lys Val Glu Arg Glu Thr Glu
                85                  90                  95

Thr Asp Pro Glu Asp
            100
```

```
<210> SEQ ID NO 62
<211> LENGTH: 58
<212> TYPE: PRT
<213> ORGANISM: human immunodeficiency virus

<400> SEQUENCE: 62

Met Glu Pro Val Asp Pro Arg Leu Glu Pro Trp Lys His Pro Gly Ser
  1               5                  10                  15

Gln Pro Lys Thr Ala Cys Thr Thr Cys Tyr Cys Lys Lys Cys Cys Phe
                20                  25                  30

His Cys Gln Val Cys Phe Ile Thr Lys Ala Leu Gly Ile Ser Tyr Gly
            35                  40                  45

Arg Lys Lys Arg Arg Gln Arg Arg Ala
    50                  55
```

```
<210> SEQ ID NO 63
<211> LENGTH: 101
<212> TYPE: PRT
<213> ORGANISM: human immunodeficiency virus

<400> SEQUENCE: 63

Met Glu Pro Val Asp Pro Arg Leu Glu Pro Trp Lys His Pro Gly Ser
  1               5                  10                  15

Gln Pro Lys Thr Ala Cys Thr Thr Cys Tyr Cys Lys Lys Cys Cys Phe
                20                  25                  30

His Cys Gln Val Cys Phe Thr Lys Lys Ala Leu Gly Ile Ser Tyr Gly
            35                  40                  45

Arg Lys Lys Arg Arg Gln Arg Arg Ala Pro Glu Asp Ser Gln Thr
    50                  55                  60

His Gln Val Ser Leu Pro Lys Gln Pro Ala Pro Gln Phe Arg Gly Asp
 65                  70                  75                  80

Pro Thr Gly Pro Lys Glu Ser Lys Lys Val Glu Arg Glu Thr Glu
                85                  90                  95

Thr His Pro Val Asp
            100
```

```
<210> SEQ ID NO 64
<211> LENGTH: 101
<212> TYPE: PRT
<213> ORGANISM: human immunodeficiency virus

<400> SEQUENCE: 64

Met Asp Pro Val Asp Pro Arg Leu Glu Pro Trp Lys His Pro Gly Ser
  1               5                  10                  15

Gln Pro Lys Ala Ala Cys Thr Ser Cys Tyr Cys Lys Lys Cys Cys Phe
                20                  25                  30

His Cys Gln Val Cys Phe Thr Thr Lys Gly Leu Gly Ile Ser Tyr Gly
            35                  40                  45

Arg Lys Lys Arg Arg Gln Arg Arg Ala Pro Gln Asp Ser Gln Thr
    50                  55                  60
```

His Gln Val Ser Leu Pro Lys Gln Pro Ala Ser Gln Ala Arg Gly Asp
65                  70                  75                  80

Pro Thr Gly Pro Lys Glu Ser Lys Lys Val Glu Arg Glu Thr Glu
                85                  90                  95

Thr Asp Pro Val Asp
            100

<210> SEQ ID NO 65
<211> LENGTH: 101
<212> TYPE: PRT
<213> ORGANISM: human immunodeficiency virus

<400> SEQUENCE: 65

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Gly Leu Gly Ile Ser Tyr Gly
            35                  40                  45

Arg Lys Lys Arg Arg Gln Arg Arg Ala Pro Pro Asp Ser Glu Val
50                  55                  60

His Gln Val Ser Leu Pro Lys Gln Pro Ala Ser Gln Pro Gly Asp
65                  70                  75                  80

Pro Thr Gly Pro Lys Glu Ser Lys Lys Val Glu Arg Glu Thr Glu
                85                  90                  95

Thr Asp Pro Val His
            100

<210> SEQ ID NO 66
<211> LENGTH: 101
<212> TYPE: PRT
<213> ORGANISM: human immundeficiency virus

<400> SEQUENCE: 66

Met Glu Pro Val Asp Pro Ser Leu Glu Pro Trp Lys His Pro Gly Ser
1               5                   10                  15

Gln Pro Lys Thr Ala Cys Thr Asn Cys Tyr Cys Lys Lys Cys Cys Leu
                20                  25                  30

His Cys Gln Val Cys Phe Thr Thr Lys Gly Leu Gly Ile Ser Tyr Gly
            35                  40                  45

Arg Lys Lys Arg Arg Gln Arg Arg Pro Pro Gln Asp Ser Gln Thr
50                  55                  60

His Gln Val Ser Leu Pro Lys Gln Pro Ser Ser Gln Gln Arg Gly Asp
65                  70                  75                  80

Pro Thr Gly Pro Lys Glu Ser Lys Lys Val Glu Arg Glu Thr Glu
                85                  90                  95

Thr Asp Pro Asp Asn
            100

<210> SEQ ID NO 67
<211> LENGTH: 1101
<212> TYPE: DNA
<213> ORGANISM: Homo sapiens

<400> SEQUENCE: 67
atggatagcg acgacgagat ggtggaggag gcggtggaag ggcacctgga cgatgacgga      60
ttaccgcacg ggttctgcac agtcacctac tcctccacag acagatttga ggggaacttt    120

```
gttcacggag aaaagaacgg acgggggaag ttcttcttct tgatggcag caccctggag      180 gggtattatg tggatgatgc cttgcagggc cagggagttt acacttacga agatggggga    240
gttctccagg gcacgtatgt agacggagag ctgaacggtc cagcccagga atatgacaca    300
gatgggagac tgatcttcaa ggggcagtat aaagataaca ttcgtcatgg agtgtgctgg    360
atatattacc cagatggagg aagccttgta ggagaagtaa atgaagatgg ggagatgact    420
ggagagaaga tagcctatgt gtaccctgat gagaggaccg cactttatgg gaaatttatt    480
gatggagaga tgatagaagg caaactggct acccttatgt ccactgaaga agggaggcct    540
cactttgaac tgatgcctgg aaattcagtg taccactttg ataagtcgac ttcatcttgc    600
atttctacca atgctcttct tccagatcct tatgaatcag aaagggttta tgttgctgaa    660
tctcttattt ccagtgctgg agaaggactt ttttcaaagg tagctgtggg acctaatact    720
gttatgtctt tttataatgg agttcgaatt acacaccaag aggttgacag cagggactgg    780
gcccttaatg gaacaccct ctcccttgat gaagaaacgg tcattgatgt gcctgagccc      840
tataaccacg tatccaagta ctgtgcctcc ttgggacaca aggcaaatca ctccttcact    900
ccaaactgca tctacgatat gtttgtccac ccccgttttg ggcccatcaa atgcatccgc    960
accctgagag cagtggaggc cgatgaagag ctcaccgttg cctatggcta tgaccacagc   1020 cccccccggga agagtgggcc tgaagcccct gagtggtacc aggtggagct gaaggccttc   1080
caggccaccc agcaaaagtg a                                              1101

<210> SEQ ID NO 68
<211> LENGTH: 7012
<212> TYPE: DNA
<213> ORGANISM: Homo sapiens

<400> SEQUENCE: 68
ggagaaagtt gcagcagcgg cagcggccaa ggcggcacac cggagcctcc gaggcgaggg      60
gcaagtgggc gaagggaggg gggacgacgg ctgctgccgc agcagctgaa ggccaaggaa    120
ttgaaagggc tgtaggggga ggcagtgcga gccagccccg actgctcctc ctcttcctcc    180
tcctcctcca aactcgcgag ccccagagct cgctcagccg ccgggagcac ccagagggac    240
gggaggcagc cgcgcagccc cgagctgggc agtgtcccca gccgccatgg atagcgacga    300
cgagatggtg gaggaggcgg tggaagggca cctggacgat gacggattac gcacgggtt     360 ctgcacagtc acctactcct ccacagacag atttgagggg aactttgttc acggagaaaa    420
gaacggacgg gggaagttct tcttctttga tggcagcacc ctggagggggt attatgtgga    480 tgatgccttg cagggccagg gagtttacac ttacgaagat gggggagttc tccagggcac    540
gtatgtagac ggagagctga acggtccagc ccaggaatat gacacagatg ggagactgat    600
cttcaagggg cagtataaag ataacattcg tcatggagtg tgctggatat attacccaga    660
tggaggaagc cttgtaggag aagtaaatga agatggggag atgactggag agaagatagc    720
ctatgtgtac cctgatgaga ggaccgcact ttatgggaaa tttattgatg gagagatgat    780
agaaggcaaa ctggctaccc ttatgtccac tgaagaaggg aggcctcact ttgaactgat    840
gcctggaaat tcagtgtacc actttgataa gtcgacttca tcttgcattt ctaccaatgc    900
tcttcttcca gatccttatg aatcagaaag ggtttatgtt gctgaatctc ttatttccag    960
tgctggagaa ggactttttt caaaggtagc tgtgggacct aatactgtta tgtcttttta   1020
taatggagtt cgaattacac accaagaggt tgacagcagg gactgggccc ttaatgggaa   1080 cacccctctcc cttgatgaag aaacggtcat tgatgtgcct gagccctata accacgtatc   1140
```

```
caagtactgt gcctccttgg gacacaaggc aaatcactcc ttcactccaa actgcatcta    1200
cgatatgttt gtccaccccc gttttgggcc catcaaatgc atccgcaccc tgagagcagt    1260
ggaggccgat gaagagctca ccgttgccta tggctatgac cacagccccc ccgggaagag    1320
tgggcctgaa gccccctgagt ggtaccaggt ggagctgaag gccttccagg ccacccagca    1380
aaagtgaaag gcctggcttt ggggttcaga gacctggaat agaaacttgg atctatgcac    1440
tacgtttatc tgacaatggg acaaccaggg actgctcatg ctgtgacgtc acatcctctc    1500
accatgcgtt agcaacgact ttctcgcata ctaactaggt ttgactgtat tactcatacc    1560
agatttaaaa ttagctagcc ttgcaacaac gtcctactga gaggtattgt cgagcatttg    1620
acataagaca gcgtgatgtt ctttggtggt tcaagtctaa atctgtacca cattcggaga    1680
tgccaaatga ttagactgaa acagggaaac ggggttttttc agtcattttt agtcagtggt    1740
ttttccatag tgcttttttc ctatggccag tgcaaattgt gttagcacac ttgcatatgt    1800
gccgtattaa ggggttgacaa ttactacatc tttattctct aaatgtagta taatttgcct    1860
tttaaccttt gatctgtatc ttgcaataga atggctttgg ttttttttctt agtaaatagg    1920 agcccacttc taaagtcatt tcaccccctca gccctattct ctttcttaga tacccttttac   1980 aagagaaaac ttccaaatgg attttttgcat caatagcagt gtgtaggtct ctctggttct    2040
ttctatatca tcattttatt attatgtcct aatataaagt actggctcat agggccaggg    2100
tattattata gaatattatt ctcgcatgta aacaaagata tctttgcttt aagatgtgag    2160
aagaaatgaa tttactttgt ttgcattaag ttatggaaga gttgtaatat atactttaag    2220
aaagaagaga agaaaactag tatctctaag cggtaactat ggcaattttg caatattttc    2280
agtagtgcta gtaattttttt cctccttgag tacacattaa atgtacataa catagcgcgg    2340
tcaggcttgt ggcacagtgc attgaattca aaagtcaaac agcaaatttg aattctaaca    2400
gaattcaaaa aaaatttttt ttagtcagta ctactaaggc agacacactg attactaggt    2460
acaaatcaaa ccttgatgct aaaactcttc atcattgtaa tttcaaagca cttacctgct    2520
tcaaaacatt gtaaactaag actgaacacc tgtatagttt aaaagcaaca ctatcaatag    2580
catttcagcc atttttgccag ccatgtgtaa tcacaactgc agaaataagg agaaaaccccc    2640 tgttttttta gtttagctaa ttagatctgt aacatcactg ggattgctct gaatgaatcc    2700
tgagagtttt gttttttata agcaccctca ccacatgcca tagctttgtc tcttttagac    2760
acctcgatgc agcggctgga aggactggag agcagctgtt gtgctgatct gtagctgtca    2820
gctgtgattc ctgtcacctg agtcagtttg gtctggaaag cgaaggcctt ccaagctgta    2880
gcagatagtg agctccagct gatgagagaa ggcttcagtg gaagaagagt gaggacatag    2940
gcagaaggaa gtttgctatt tcttgtcagt tgcacattgc tttatgaaga ctacaacaaa    3000
agtgcttaat cccaggctgc tcatgacttt catttcaggt ggcccttggg cacattgaca    3060
gagttgccct tcccttcttt gcaacaccag gcttcctaga gcacccggtt gcatgctttg    3120
cagctaggtg gcagtggttt cagggagatc cagttggatc cctgcttgaa agcttaagcc    3180
aatggttcac ccatgagagg aagttgtcag tgcttccagg aagattgccc accaaaggaa    3240
ctgaatagtt tttagattta aaggcaccag gatagggtca ctcttactct gtagaaagag    3300
accgttctat acactgtgac ggatgggcca gggcctctgg acttgcattc tgataggtgc    3360
tttaatttaa atgtgcccaa agggagtgac tgtcttcagg agaaagatgg cttgcattaa    3420
cctcgatcaa gtgggttgtg cagccaggtc agggaatgcg gtcagggaga ggatagtgct    3480
ggtcatgccc ccgatgcagc tatgctctga atgatttcat tcctgagagt gatagcattc    3540
```

```
tggtcctggc tgcagtgggg tacaatttac gtcctaagtg ggggctactc taattatccc    3600
attcaaatgg aatttttttc aaaattggat agaaggaatt gaagagttgt aagtagtgat    3660
tagtctgcta atcagttctt cagatgagat attgaatggt aacactctga gcttaaaact    3720
cagcagtgtg tctgtgacct ccacgcaaat cagaggaagc aatgcatcca cgctgagcct    3780
caccatgtct tcctcccaac tctcttcata ctctctgtgt cttccagctc ttctttctct    3840
ggccggctct ctttcctctt ctctctgcat atgtgagaac gcctgggcat cctgggtaac    3900
agcagcccca gctgccctct cctgttccct gttccaagtc ccctgcactg acctttcttg    3960
agtctctctg gctctgtgca tgtctttggg actctgctca tctggctttt cctctgtgtg    4020
tgcctctctg tttgcttatg tctctggctc tgtcttcccc acccctcccc tcacacacac    4080
acatactccc aaatgtaagg ctctgtggca ggttggaatc ggagtaaggc ttgagattca    4140
ctgagttctg taggtaggga agaagtcaa gggagtggag gttctataag gaattaacag     4200
ctgaggacgg aagggtttgt ttcccgtttg aacctaaacg caagtggaaa agaatactca    4260
gaatgtattt ttctacttta catctgctgg ggaaggaaat gtgtcaggaa gccgctgcat    4320
ctggtcattt catcgcatca gaatcacagc agacgtggaa gattccatgt ggtggggaat    4380
aaagaaataa ctttatgctc tcctgaaaaa cagcgggagc ctatgtgtgt gtgcgacact    4440
gtaatctcaa ggagattcac tcagagctgt ctccagtccaa ctcctgcatg accagatctt   4500
cccttagcat cttttctgtg atgaaatatt atcttgtgtt agagttagga ataggaacta    4560
acctgtagga gcatgtcccc aaatggacat ttgaatggac taacaaaaac aactggaaag    4620
actgaatttc cgacacaaag gaatgatggg atcaaaaaga aagcagtgag gagttcttga    4680
gtcttgtagt acctattctt attttaactt gcttcatcct tgatctacct gagacactaa    4740
gaaggaaatt agttttccaa gagctctttg aacctgtcta ggactgtagt taaacctatt    4800
tgccctatgg gggttcttca cactcgaaaa actatttcct tatcaccaac gacccaccca    4860
gaaaggccaa tgaggccaaa tgtaacaatt tttaacattt aaatataact attaaaattg    4920
cattaattgt gaacagtgaa ttaaagggtt gtcttctcca ggagacagta tgtggcactt    4980
ttcgtaaatt tcatttaata tataaaaatt taaatcactc actgcaacat gcatttaaaa    5040
tcttccaaga aggtagaggt atcattttct gttttgcttt gtttttaaaac agttgcctca    5100 agcttctgtc ttaagagtag tgacttagaa tccagatatc ttttgtttta gaaaacaag     5160 caaaactatg ttgcaagact gacagttgta atgtttattt gccacagatc aaaggttcac    5220
aaagtatatc aaatttacat ctacttgggg taccttgata gattattatt gtttttcttt    5280
tatctttccc ttcaggaatt tggaaactcg ttgtcacttt ttttaatttt aaaaatacta    5340
aattgtaata gttttctttt gccaaatgtg tgcgtacata ttcaaagcaa tgaaactatt    5400
tcaagccata caaccacagg ggtgggaacc cttttcacaa attttaatgt gtttgtatgt    5460
aaatagatgt ttgtatgaaa tattttcatg atagaatgaa tatatttaaa tgaagttgaa    5520
ttattccagt gctacttaaa cacattacaa aaattttggt gagaattatc tgagtctatt    5580
gagatgtaat gcagatcaat tttgatttt aaaaatcaaa agcctacaat aactctgact     5640
ctcagcaact tcctcggcgt tgttgcacct gacgtggaga gagctcgtag gcttccccag    5700
tgcctcagcc gcttcctggt ggaagttagg tgctaatgga ggtgtgttca ccttttagtg    5760
atatcactgc aggcctttga ggggcctgag agtgaatcag aggcattaga gacaccggtg    5820
cagttatctg gagcacaatt tctttgcagg gcagcagaat cagaagccag acttggccat    5880
gtgaacctcg aaactcggtt tccggccgc catcaaccgc caccccttact gcctagtcac    5940
```

```
acacgtcagg gaggctgccc tcagtggagt tggggttgag accccagggt gggacttcac    6000
agttttgcca gcaatctcta ccttctgact tctgcctcgc agagaggaag gagagggag     6060 catctggcaa ggggcccatt tctcagcaca gtacatttcc tgtctcagct ctggaagact    6120
atgcacccaa gcaccaaact tccaaccaga gagagagacg tcctccgata acaaaaatcc    6180
ttgcttcctc tgtctgtgac tttacacaca gttgttcaaa gttgttaaat gtcaagagtc    6240
aatcacatcc ctaggacata cctcccaact ctcctgactc ttatgttatt gaaaaacaa     6300 acaaacaaaa actcctttat gatgatattc aacttgagtg gggttttttt tccactttgg    6360
tcctggatat aatgaaatga tacatattag gataaatttt cactgtgtat agtagcaata    6420
cgaacacaca tgccaatgta tcaacatatc tacttggtta cattttggtt tatgataatt    6480
aaccttgatt catgtattgg gaagctacag ggactacgta atacctgctt atcacatagg    6540
aaaattatgt ccatgattct gagctccctt cttcaaaagt ttcctcctgg gtgttctatg    6600
ttctctcttt atcctgaaat acatttatta ggttgtgagg tatgttgaag aagtagaagc    6660
caggggtatg ctttcagcat ttattgcaac caaaagttaa ccccatcacg gttaacgagc    6720
atctttggtc tcttgtggaa tttgaactaa aactatgagc cttattcaat atctataatt    6780
ctatgatttt tttaaattat gggaaattaa tgaaagatgt ttacatgaat aatgtttgcc    6840
cttactgtgt tatgaatgag ttttttgtag tgtgtctggg tgcatgatgc aagagagtag    6900
gaaaaatgtt tctgaaacaa aacttgacaa atatttgtaa tgaaagtaaa tttaaagatt    6960
gctataattg cgctatagaa acaatgcaag tattaaacaa aatatacaat ca            7012
```

<210> SEQ ID NO 69
<211> LENGTH: 28
<212> TYPE: DNA
<213> ORGANISM: Artificial Sequence
<220> FEATURE:
<223> OTHER INFORMATION: primer

<400> SEQUENCE: 69
cctatggcag gaaggcgcgg agacagcg                                        28

<210> SEQ ID NO 70
<211> LENGTH: 28
<212> TYPE: DNA
<213> ORGANISM: Artificial Sequence
<220> FEATURE:
<223> OTHER INFORMATION: primer

<400> SEQUENCE: 70
cgctgtctcc gcgccttcct gccatagg                                        28

<210> SEQ ID NO 71
<211> LENGTH: 28
<212> TYPE: DNA
<213> ORGANISM: Artificial Sequence
<220> FEATURE:
<223> OTHER INFORMATION: primer

<400> SEQUENCE: 71
cctatggcag gaagaggcgg agacagcg                                        28

<210> SEQ ID NO 72
<211> LENGTH: 28
<212> TYPE: DNA
<213> ORGANISM: Artificial Sequence
<220> FEATURE:
<223> OTHER INFORMATION: primer

```
<400> SEQUENCE: 72
cgctgtctcc gcctcttcct gccatagg                                    28

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
gagccctcag atcctgcata                                             20

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
agctcctctg gtttcccttt                                             20

<210> SEQ ID NO 75
<211> LENGTH: 18
<212> TYPE: DNA
<213> ORGANISM: Artificial Sequence
<220> FEATURE:
<223> OTHER INFORMATION: primer

<400> SEQUENCE: 75
gccagctgca agccttgg                                               18

<210> SEQ ID NO 76
<211> LENGTH: 18
<212> TYPE: DNA
<213> ORGANISM: Artificial Sequence
<220> FEATURE:
<223> OTHER INFORMATION: primer

<400> SEQUENCE: 76
gccactgggc ctccattc                                               18

<210> SEQ ID NO 77
<211> LENGTH: 21
<212> TYPE: DNA
<213> ORGANISM: Artificial Sequence
<220> FEATURE:
<223> OTHER INFORMATION: primer

<400> SEQUENCE: 77
atggtgagca agggcgagga g                                           21

<210> SEQ ID NO 78
<211> LENGTH: 20
<212> TYPE: DNA
<213> ORGANISM: Artificial Sequence
<220> FEATURE:
<223> OTHER INFORMATION: primer

<400> SEQUENCE: 78
gtggtgcaga tgaacttcag                                             20

<210> SEQ ID NO 79
<211> LENGTH: 397
<212> TYPE: PRT
```

<213> ORGANISM: Homo sapiens

<400> SEQUENCE: 79

| | | | | | | | | | | | | | | |
|---|---|---|---|---|---|---|---|---|---|---|---|---|---|---|
| Met | Ser | Ser | Leu | Pro | Gly | Cys | Ile | Gly | Leu | Asp | Ala | Ala | Thr | Ala | Thr |
| 1 | | | | 5 | | | | | 10 | | | | | 15 | |
| Val | Glu | Ser | Glu | Glu | Ile | Ala | Glu | Leu | Gln | Gln | Ala | Val | Val | Glu | Glu |
| | | | 20 | | | | | 25 | | | | | 30 | | |
| Leu | Gly | Ile | Ser | Met | Glu | Glu | Leu | Arg | His | Phe | Ile | Asp | Glu | Glu | Leu |
| | | 35 | | | | | 40 | | | | | 45 | | | |
| Glu | Lys | Met | Asp | Cys | Val | Gln | Gln | Arg | Lys | Lys | Gln | Leu | Ala | Glu | Leu |
| | 50 | | | | | 55 | | | | | 60 | | | | |
| Glu | Thr | Trp | Val | Ile | Gln | Lys | Glu | Ser | Glu | Val | Ala | His | Val | Asp | Gln |
| 65 | | | | | 70 | | | | | 75 | | | | | 80 |
| Leu | Phe | Asp | Asp | Ala | Ser | Arg | Ala | Val | Thr | Asn | Cys | Glu | Ser | Leu | Val |
| | | | | 85 | | | | | 90 | | | | | 95 | |
| Lys | Asp | Phe | Tyr | Ser | Lys | Leu | Gly | Leu | Gln | Tyr | Arg | Asp | Ser | Ser | Ser |
| | | | 100 | | | | | 105 | | | | | 110 | | |
| Glu | Asp | Glu | Ser | Ser | Arg | Pro | Thr | Glu | Ile | Ile | Glu | Ile | Pro | Asp | Glu |
| | | 115 | | | | | 120 | | | | | 125 | | | |
| Asp | Asp | Asp | Val | Leu | Ser | Ile | Asp | Ser | Gly | Asp | Ala | Gly | Ser | Arg | Thr |
| | 130 | | | | | 135 | | | | | 140 | | | | |
| Pro | Lys | Asp | Gln | Lys | Leu | Arg | Glu | Ala | Met | Ala | Ala | Leu | Arg | Lys | Ser |
| 145 | | | | | 150 | | | | | 155 | | | | | 160 |
| Ala | Gln | Asp | Val | Gln | Lys | Phe | Met | Asp | Ala | Val | Asn | Lys | Lys | Ser | Ser |
| | | | | 165 | | | | | 170 | | | | | 175 | |
| Ser | Gln | Asp | Leu | His | Lys | Gly | Thr | Leu | Ser | Gln | Met | Ser | Gly | Glu | Leu |
| | | | 180 | | | | | 185 | | | | | 190 | | |
| Ser | Lys | Asp | Gly | Asp | Leu | Ile | Val | Ser | Met | Arg | Ile | Leu | Gly | Lys | Lys |
| | | 195 | | | | | 200 | | | | | 205 | | | |
| Arg | Thr | Lys | Thr | Trp | His | Lys | Gly | Thr | Leu | Ile | Ala | Ile | Gln | Thr | Val |
| | 210 | | | | | 215 | | | | | 220 | | | | |
| Gly | Pro | Gly | Lys | Lys | Tyr | Lys | Val | Lys | Phe | Asp | Asn | Lys | Gly | Lys | Ser |
| 225 | | | | | 230 | | | | | 235 | | | | | 240 |
| Leu | Leu | Ser | Gly | Asn | His | Ile | Ala | Tyr | Asp | Tyr | His | Pro | Pro | Ala | Asp |
| | | | | 245 | | | | | 250 | | | | | 255 | |
| Lys | Leu | Tyr | Val | Gly | Ser | Arg | Val | Val | Ala | Lys | Tyr | Lys | Asp | Gly | Asn |
| | | | 260 | | | | | 265 | | | | | 270 | | |
| Gln | Val | Trp | Leu | Tyr | Ala | Gly | Ile | Val | Ala | Glu | Thr | Pro | Asn | Val | Lys |
| | | 275 | | | | | 280 | | | | | 285 | | | |
| Asn | Lys | Leu | Arg | Phe | Leu | Ile | Phe | Phe | Asp | Asp | Gly | Tyr | Ala | Ser | Tyr |
| | 290 | | | | | 295 | | | | | 300 | | | | |
| Val | Thr | Gln | Ser | Glu | Leu | Tyr | Pro | Ile | Cys | Arg | Pro | Leu | Lys | Lys | Thr |
| 305 | | | | | 310 | | | | | 315 | | | | | 320 |
| Trp | Glu | Asp | Ile | Glu | Asp | Ile | Ser | Cys | Arg | Asp | Phe | Ile | Glu | Glu | Tyr |
| | | | | 325 | | | | | 330 | | | | | 335 | |
| Val | Thr | Ala | Tyr | Pro | Asn | Arg | Pro | Met | Val | Leu | Leu | Lys | Ser | Gly | Gln |
| | | | 340 | | | | | 345 | | | | | 350 | | |
| Leu | Ile | Lys | Thr | Glu | Trp | Glu | Gly | Thr | Trp | Trp | Lys | Ser | Arg | Val | Glu |
| | | 355 | | | | | 360 | | | | | 365 | | | |
| Glu | Val | Asp | Gly | Ser | Leu | Val | Arg | Ile | Leu | Phe | Leu | Val | Leu | Phe | Phe |
| | 370 | | | | | 375 | | | | | 380 | | | | |
| Ser | Thr | Ile | Leu | Glu | Ala | Glu | Val | Gly | Gly | Gly | Thr | | | | |
| 385 | | | | | 390 | | | | | 395 | | | | | |

```
<210> SEQ ID NO 80
<211> LENGTH: 707
<212> TYPE: PRT
<213> ORGANISM: Homo sapiens

<400> SEQUENCE: 80

Met Gly Glu Lys Asn Gly Asp Ala Lys Thr Phe Trp Met Glu Leu Glu
  1               5                  10                  15

Asp Asp Gly Lys Val Asp Phe Ile Phe Glu Gln Val Gln Asn Val Leu
             20                  25                  30

Gln Ser Leu Lys Gln Lys Ile Lys Asp Gly Ser Ala Thr Asn Lys Glu
         35                  40                  45

Tyr Ile Gln Ala Met Ile Leu Val Asn Glu Ala Thr Ile Ile Asn Ser
     50                  55                  60

Ser Thr Ser Ile Lys Asp Pro Met Pro Val Thr Gln Lys Glu Gln Glu
 65                  70                  75                  80

Asn Lys Ser Asn Ala Phe Pro Ser Thr Ser Cys Glu Asn Ser Phe Pro
                 85                  90                  95

Glu Asp Cys Thr Phe Leu Thr Thr Gly Asn Lys Glu Ile Leu Ser Leu
            100                 105                 110

Glu Asp Lys Val Val Asp Phe Arg Glu Lys Asp Ser Ser Ser Asn Leu
        115                 120                 125

Ser Tyr Gln Ser His Asp Cys Ser Gly Ala Cys Leu Met Lys Met Pro
    130                 135                 140

Leu Asn Leu Lys Gly Glu Asn Pro Leu Gln Leu Pro Ile Lys Cys His
145                 150                 155                 160

Phe Gln Arg Arg His Ala Lys Thr Asn Ser His Ser Ser Ala Leu His
                165                 170                 175

Val Ser Tyr Lys Thr Pro Cys Gly Arg Ser Leu Arg Asn Val Glu Glu
            180                 185                 190

Val Phe Arg Tyr Leu Leu Glu Thr Glu Cys Asn Phe Leu Phe Thr Asp
        195                 200                 205

Asn Phe Ser Phe Asn Thr Tyr Val Gln Leu Ala Arg Asn Tyr Pro Lys
    210                 215                 220

Gln Lys Glu Val Val Ser Asp Val Asp Ile Ser Asn Gly Val Glu Ser
225                 230                 235                 240

Val Pro Ile Ser Phe Cys Asn Glu Ile Asp Ser Arg Lys Leu Pro Gln
                245                 250                 255

Phe Lys Tyr Arg Lys Thr Val Trp Pro Arg Ala Tyr Asn Leu Thr Asn
            260                 265                 270

Phe Ser Ser Met Phe Thr Asp Ser Cys Asp Cys Ser Glu Gly Cys Ile
        275                 280                 285

Asp Ile Thr Lys Cys Ala Cys Leu Gln Leu Thr Ala Arg Asn Ala Lys
    290                 295                 300

Thr Ser Pro Leu Ser Ser Asp Lys Ile Thr Thr Gly Tyr Lys Tyr Lys
305                 310                 315                 320

Arg Leu Gln Arg Gln Ile Pro Thr Gly Ile Tyr Glu Cys Ser Leu Leu
                325                 330                 335

Cys Lys Cys Asn Arg Gln Leu Cys Gln Asn Arg Val Val Gln His Gly
            340                 345                 350

Pro Gln Val Arg Leu Gln Val Phe Lys Thr Glu Gln Lys Gly Trp Gly
        355                 360                 365

Val Arg Cys Leu Asp Asp Ile Asp Arg Gly Thr Phe Val Cys Ile Tyr
    370                 375                 380

Ser Gly Arg Leu Leu Ser Arg Ala Asn Thr Glu Lys Ser Tyr Gly Ile
```

```
            385                 390                 395                 400
Asp Glu Asn Gly Arg Asp Glu Asn Thr Met Lys Asn Ile Phe Ser Lys
                    405                 410                 415

Lys Arg Lys Leu Glu Val Ala Cys Ser Asp Cys Glu Val Glu Val Leu
                420                 425                 430

Pro Leu Gly Leu Glu Thr His Pro Arg Thr Ala Lys Thr Glu Lys Cys
            435                 440                 445

Pro Pro Lys Phe Ser Asn Asn Pro Lys Glu Leu Thr Met Glu Thr Lys
        450                 455                 460

Tyr Asp Asn Ile Ser Arg Ile Gln Tyr His Ser Val Ile Arg Asp Pro
465                 470                 475                 480

Glu Ser Lys Thr Ala Ile Phe Gln His Asn Gly Lys Lys Met Glu Phe
                485                 490                 495

Val Ser Ser Glu Ser Val Thr Pro Glu Asp Asn Asp Gly Phe Lys Pro
            500                 505                 510

Pro Arg Glu His Leu Asn Ser Lys Thr Lys Gly Ala Gln Lys Asp Ser
        515                 520                 525

Ser Ser Asn His Val Asp Glu Phe Glu Asp Asn Leu Leu Ile Glu Ser
    530                 535                 540

Asp Val Ile Asp Ile Thr Lys Tyr Arg Glu Glu Thr Pro Pro Arg Ser
545                 550                 555                 560

Arg Cys Asn Gln Ala Thr Thr Leu Asp Asn Gln Asn Ile Lys Lys Ala
                565                 570                 575

Ile Glu Val Gln Ile Gln Lys Pro Gln Glu Gly Arg Ser Thr Ala Cys
            580                 585                 590

Gln Arg Gln Gln Val Phe Cys Asp Glu Glu Leu Leu Ser Glu Thr Lys
        595                 600                 605

Asn Thr Ser Ser Asp Ser Leu Thr Lys Phe Asn Lys Gly Asn Val Phe
    610                 615                 620

Leu Leu Asp Ala Thr Lys Glu Gly Asn Val Gly Arg Phe Leu Asn His
625                 630                 635                 640

Ser Cys Cys Pro Asn Leu Leu Val Gln Asn Val Phe Val Glu Thr His
                645                 650                 655

Asn Arg Asn Phe Pro Leu Val Ala Phe Phe Thr Asn Arg Tyr Val Lys
            660                 665                 670

Ala Arg Thr Glu Leu Thr Trp Asp Tyr Gly Tyr Glu Ala Gly Thr Val
        675                 680                 685

Pro Glu Lys Glu Ile Phe Cys Gln Cys Gly Val Asn Lys Cys Arg Lys
    690                 695                 700

Lys Ile Leu
705

<210> SEQ ID NO 81
<211> LENGTH: 288
<212> TYPE: PRT
<213> ORGANISM: Homo sapiens

<400> SEQUENCE: 81

Leu Glu Val Ala Cys Ser Asp Cys Glu Val Glu Val Leu Pro Leu Gly
1               5                   10                  15

Leu Glu Thr His Pro Arg Thr Ala Lys Thr Glu Lys Cys Pro Pro Lys
            20                  25                  30

Phe Ser Asn Asn Pro Lys Glu Leu Thr Val Glu Thr Lys Tyr Asp Asn
        35                  40                  45

Ile Ser Arg Ile Gln Tyr His Ser Val Ile Arg Asp Pro Glu Ser Lys
```

```
                50                  55                  60
Thr Ala Ile Phe Gln His Asn Gly Lys Lys Met Glu Phe Val Ser Ser
 65                  70                  75                  80

Glu Ser Val Thr Pro Glu Asp Asn Asp Gly Phe Lys Pro Pro Arg Glu
                 85                  90                  95

His Leu Asn Ser Lys Thr Lys Gly Ala Gln Lys Asp Ser Ser Ser Asn
                100                 105                 110

His Val Asp Glu Phe Glu Asp Asn Leu Leu Ile Glu Ser Asp Val Ile
                115                 120                 125

Asp Ile Thr Lys Tyr Arg Glu Glu Thr Pro Pro Arg Ser Arg Cys Asn
            130                 135                 140

Gln Ala Thr Thr Leu Asp Asn Gln Asn Ile Lys Lys Ala Ile Glu Val
145                 150                 155                 160

Gln Ile Gln Lys Pro Gln Glu Gly Arg Ser Thr Ala Cys Gln Arg Gln
                165                 170                 175

Gln Val Phe Cys Asp Glu Glu Leu Leu Ser Glu Thr Lys Asn Thr Ser
                180                 185                 190

Ser Asp Ser Leu Thr Lys Phe Asn Lys Gly Asn Val Phe Leu Leu Asp
            195                 200                 205

Ala Thr Lys Glu Gly Asn Val Gly Arg Phe Leu Asn His Ser Cys Cys
210                 215                 220

Pro Asn Leu Leu Val Gln Asn Val Phe Val Glu Thr His Asn Arg Asn
225                 230                 235                 240

Phe Pro Leu Val Ala Phe Phe Thr Asn Arg Tyr Val Lys Ala Arg Thr
                245                 250                 255

Glu Leu Thr Trp Asp Tyr Gly Tyr Glu Ala Gly Thr Val Pro Glu Lys
                260                 265                 270

Glu Ile Phe Cys Gln Cys Gly Val Asn Lys Cys Arg Lys Lys Ile Leu
                275                 280                 285

<210> SEQ ID NO 82
<211> LENGTH: 1194
<212> TYPE: DNA
<213> ORGANISM: Homo sapiens

<400> SEQUENCE: 82
atgtcttccc ttcctgggtg cattggtttg gatgcagcaa cagctacagt ggagtctgaa      60
gagattgcag agctgcaaca ggcagtggtt gaggaactgg gtatctctat ggaggaactt     120
cggcatttca tcgatgagga actggagaag atggattgtg tacagcaacg caagaagcag     180
ctagcagagt tagagacatg gtaatacag aaagaatctg aggtggctca cgttgaccaa     240
ctctttgatg atgcatccag ggcagtgact aattgtgagt cttttggtgaa ggacttctac     300 tccaagctgg gactacaata ccgggacagt agctctgagg acgaatcttc ccggcctaca     360
gaaataattg agattcctga tgaagatgat gatgtcctca gtattgattc aggtgatgct     420
gggagcagaa ctccaaaaga ccagaagctc cgtgaagcta tggctgcctt aagaaagtca     480
gctcaagatg ttcagaagtt catggatgct gtcaacaaga gagcagttc ccaggatctg     540 cataaaggaa ccttgagtca gatgtctgga gaactaagca aagatggtga cctgatagtc     600
agcatgcgaa ttctgggcaa gagagaact aagacttggc acaaaggcac cttattgcc     660 atccagacag ttgggccagg gaagaatac aaggtgaaat ttgacaacaa aggaaagagt     720
ctactgtcgg ggaaccatat tgcctatgat taccaccctc ctgctgacaa gctgtatgtg     780
ggcagtcggg tggtcgccaa atacaaagat gggaatcagg tctggctcta tgctggcatt     840
```

-continued

```
gtagctgaga caccaaacgt caaaaacaag ctcaggtttc tcattttctt tgatgatggc      900
tatgcttcct atgtcacaca gtcggaactg tatcccattt gccggccact gaaaaagact      960
tgggaggaca tagaagacat ctcctgccgt gacttcatag aggagtatgt cactgcctac     1020
cccaaccgcc ccatggtact gctcaagagt ggccagctta tcaagactga gtgggaaggc     1080
acgtggtgga agtcccgagt tgaggaggtg gatggcagcc tagtcaggat cctcttcctg     1140
gtactgttct tctctacaat tttggaggca gaggttggtg ggggggaac ttaa            1194

<210> SEQ ID NO 83
<211> LENGTH: 868
<212> TYPE: DNA
<213> ORGANISM: Homo sapiens

<400> SEQUENCE: 83
attagaagtt gcatgttcag attgtgaagt tgaagttctc ccattaggat tggaaacaca       60
tcctagaact gctaaaactg agaaatgtcc accaaagttc agtaataatc ccaaggagct      120
tactgtggaa acgaaatatg ataatatttc aagaattcaa tatcattcag ttattagaga      180
tcctgaatcc aagacagcca tttttcaaca caatgggaaa aaaatggaat ttgtttcctc      240
ggagtctgtc actccagaag ataatgatgg atttaaacca ccccgagagc atctgaactc      300
taaaaccaag ggagcacaaa aggactcaag ttcaaaccat gttgatgagt ttgaagataa      360
tctgctgatt gaatcagatg tgatagatat aactaaatat agagaagaaa ctccaccaag      420
gagcagatgt aaccaggcga ccacattgga taatcagaat attaaaaagg caattgaggt      480
tcaaattcag aaaccccaag agggacgatc tacagcatgt caaagacagc aggtattttg      540
tgatgaagag ttgctaagtg aaaccaagaa tacttcatct gattctctaa caaagttcaa      600
taaagggaat gtgtttttat tggatgccac aaaagaagga aatgtcggcc gcttccttaa      660
tcatagttgt tgcccaaatc tcttggtaca gaatgttttt gtagaaacac acaacaggaa      720
ttttccattg gtggcattct tcaccaacag gtatgtgaaa gcaagaacag agctaacatg      780
ggattatggc tatgaagctg ggactgtgcc tgagaaggaa atcttctgcc aatgtggggt      840
taataaatgt agaaaaaaaa tattataa                                         868
```